(12) United States Patent
Fischer et al.

(10) Patent No.: US 6,229,064 B1
(45) Date of Patent: May 8, 2001

(54) NUCLEIC ACIDS THAT CONTROL ENDOSPERM DEVELOPMENT IN PLANTS

(75) Inventors: Robert L. Fischer, El Cerrito, CA (US); Nir Ohad, Jerusalem (IL); Tomohiro Kiyosue, Okazaki (JP); Ramin Yadegari, San Jose, CA (US); Linda Margossian, El Cerrito, CA (US); John Harada, Davis, CA (US); Robert B. Goldberg, Topanga, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/177,249

(22) Filed: Oct. 22, 1998

Related U.S. Application Data

(63) Continuation-in-part of application No. 09/071,838, filed on May 1, 1998.
(51) Int. Cl.[7] .......................... C12N 15/29; C12N 15/82; C12N 15/90; A01H 5/00; A01H 5/10
(52) U.S. Cl. .................. 800/278; 435/69.1; 435/320.1; 435/468; 536/23.6; 800/286; 800/287; 800/298
(58) Field of Search .......................... 435/69.1, 320.1, 435/410, 419, 468; 536/23.6, 24.1; 800/278, 285, 286, 287, 290, 295, 298

(56) References Cited

PUBLICATIONS

Ohad et al, Proc. Natl. Acad. Sci. USA, vol. 93, pp. 5319–5324, 1996.*
Grossniklaus et al, Science, vol. 280, pp. 446–450, 1998.*
van der Krol et al, Gene, vol. 72, pp. 45–50, 1988.*
Holtorf et al, Plant Mol. Biol., vol. 29, pp. 637–646, 1995.*
V. Pirrotta, "PcG complexes and chromatin silencing"; *Current Opinion in Genetics & Development*, 7:249–258, (1997).
Goodrich, et al., "A Polycomb–group gene regulates homeotic gene expression in *Arabidopsis*"; *Nature*, vol. 38616, pp 44–51, (Mar. 1997).
Gutjahr, et al., "The Polycomb–group gene, *extra sex combs*, encodes a nuclear member of the WD–40 repeat family"; *The EMBO Journal*, vol. 14, No. 17, pp. 4296–4306, (1995).
Jenuwein, et al., "SET domain proteins modulate chromatin domains in eu– and heterochromatin", *CMLS, Cell. Mol. Life Sci.*, 54: 80–93 (1998).
Grossniklaus, et al., "Maternal Control of Embryongenesis by *MEDEA*, A *Polycomb* Group Gene in *Arabidopsis*"; *Science*, vol. 280, pp 446–450, (Apr. 1998).
Ohad, et al., "A mutation that allows endosperm development without fertilization"; *Proc. Natl. Acad. Sci.* vol. 93, pp. 5319–5324 (May 1996).
Chaudhury, et al., "Fertilization–independent seed development in *Arabidopsis thaliana*"; *Proc. Natl. Acad. Sci.*, vol. 94, pp. 4223–4228 (Apr. 1997).
Miki, et al., "Procedures for Introducing Foreign DNA into Plants"; *Methods in Plant Molecular Biology and Biotechnology*, pp. 67–88 (1993).

\* cited by examiner

*Primary Examiner*—Paula Hutzell
*Assistant Examiner*—Ashwin D. Mehta
(74) *Attorney, Agent, or Firm*—Townsend and Townsend and Crew LLP

(57) ABSTRACT

The invention provides methods of controlling endosperm development in plants.

22 Claims, 5 Drawing Sheets

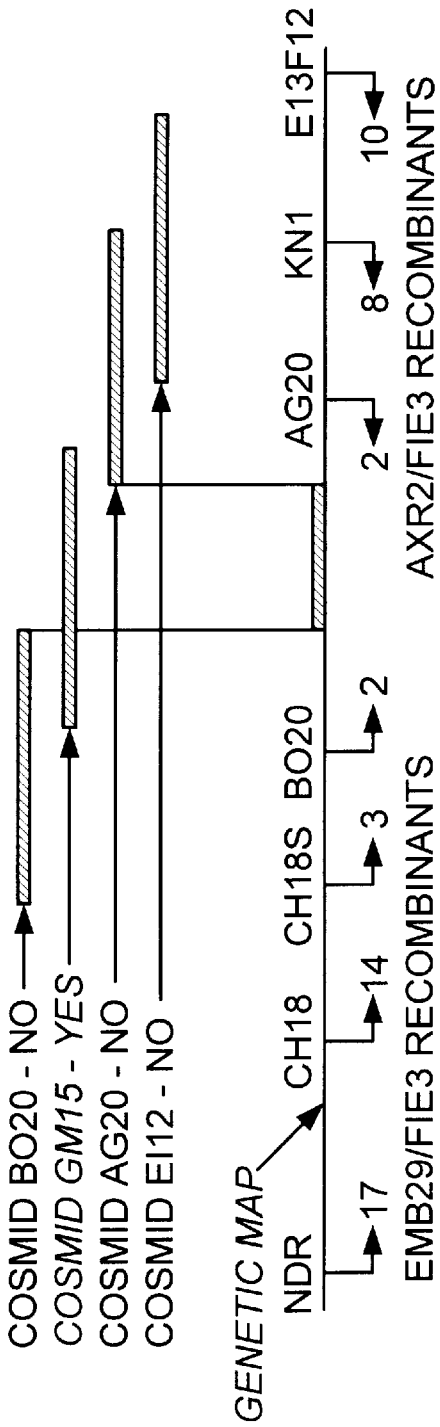
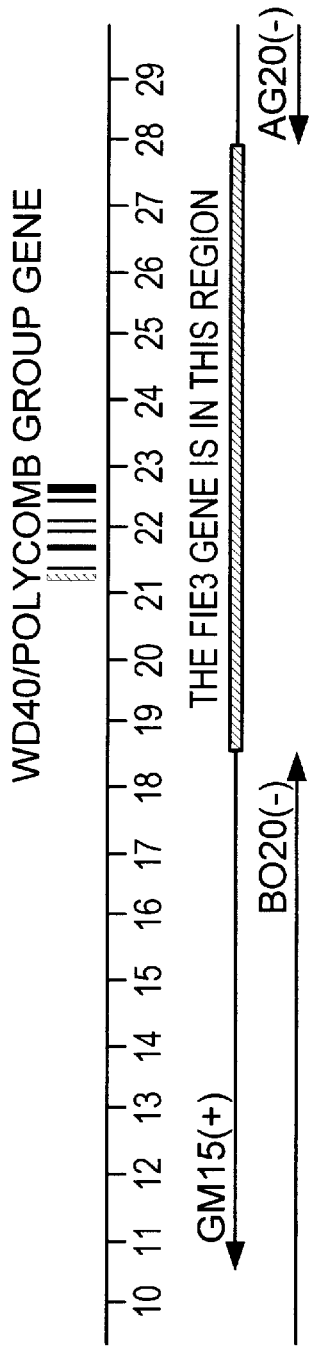
FIG. 1A.
FIG. 1B.

SEQUENCE LISTING

<160> NUMBER OF SEQ ID NOS: 324

<210> SEQ ID NO: 1
<211> LENGTH: 2136
<212> TYPE: DNA
<213> ORGANISM: Arabidopsis sp.
<220> FEATURE:
<221> NAME/KEY: CDS
<222> LOCATION: (43)..(2112)
<223> OTHER INFORMATION: fertilization-independent endosperm 1 (FIE1) cDNA

<400> SEQUENCE: 1

```
aacatcagag aagacgagaa aaaagaaga ggcgagtggt ta atg gag aag gaa            54
                                              Met Glu Lys Glu
                                                1 aac cat gag gac gat ggt gag ggt ttg cca ccc gaa cta aat cag ata         102
Asn His Glu Asp Asp Gly Glu Gly Leu Pro Pro Glu Leu Asn Gln Ile
  5                  10                  15                  20 aaa gag caa atc gaa aag gag aga ttt ctg cat atc aag aga aaa ttc         150
Lys Glu Gln Ile Glu Lys Glu Arg Phe Leu His Ile Lys Arg Lys Phe
             25                  30                  35 gag ctg aga tac att cca agt gtg gct act cat gct tca cac cat caa         198
Glu Leu Arg Tyr Ile Pro Ser Val Ala Thr His Ala Ser His His Gln
         40                  45                  50 tcg ttt gac tta aac cag ccc gct gca gag gat gat aat gga gga gac         246
Ser Phe Asp Leu Asn Gln Pro Ala Ala Glu Asp Asp Asn Gly Gly Asp
     55                  60                  65 aac aaa tca ctt ttg tcg aga atg caa aac cca ctt cgt cat ttc agt         294
Asn Lys Ser Leu Leu Ser Arg Met Gln Asn Pro Leu Arg His Phe Ser
 70                  75                  80 gcc tca tct gat tat aat tct tac gaa gat caa ggt tat gtt ctt gat         342
Ala Ser Ser Asp Tyr Asn Ser Tyr Glu Asp Gln Gly Tyr Val Leu Asp
 85                  90                  95                 100 gag gat caa gat tat gct ctt gaa gaa gat gta cca tta ttt ctt gat         390
Glu Asp Gln Asp Tyr Ala Leu Glu Glu Asp Val Pro Leu Phe Leu Asp
                105                 110                 115 gaa gat gta cca tta tta cca agt gtc aag ctt cca att gtt gag aag         438
Glu Asp Val Pro Leu Leu Pro Ser Val Lys Leu Pro Ile Val Glu Lys
            120                 125                 130 cta cca cga tcc att aca tgg gtc ttc acc aaa agt agc cag ctg atg         486
Leu Pro Arg Ser Ile Thr Trp Val Phe Thr Lys Ser Ser Gln Leu Met
        135                 140                 145 gct gaa agt gat tct gtg att ggt aag aga caa atc tat tat ttg aat         534
Ala Glu Ser Asp Ser Val Ile Gly Lys Arg Gln Ile Tyr Tyr Leu Asn
    150                 155                 160 ggt gag gca cta gaa ttg agc agt gaa gaa gat gag gaa gat gaa gaa         582
Gly Glu Ala Leu Glu Leu Ser Ser Glu Glu Asp Glu Glu Asp Glu Glu
165                 170                 175                 180 gaa gat gag gaa gaa atc aag aaa gaa aaa tgc gaa ttt tct gaa gat         630
Glu Asp Glu Glu Glu Ile Lys Lys Glu Lys Cys Glu Phe Ser Glu Asp
                185                 190                 195 gta gac cga ttt ata tgg acg gtt ggg cag gac tat ggt ttg gat gat         678
Val Asp Arg Phe Ile Trp Thr Val Gly Gln Asp Tyr Gly Leu Asp Asp
            200                 205                 210 ctg gtc gtg cgg cgt gct ctc gcc aag tac ctc gaa gtg gat gtt tcg         726
Leu Val Val Arg Arg Ala Leu Ala Lys Tyr Leu Glu Val Asp Val Ser
        215                 220                 225 gac ata ttg gaa aga tac aat gaa ctc aag ctt aag aat gat gga act         774
Asp Ile Leu Glu Arg Tyr Asn Glu Leu Lys Leu Lys Asn Asp Gly Thr
```

```
            230                 235                 240
gct ggt gag gct tct gat ttg aca tcc aag aca ata act act gct ttc      822
Ala Gly Glu Ala Ser Asp Leu Thr Ser Lys Thr Ile Thr Thr Ala Phe
245                 250                 255                 260 cag gat ttt gct gat aga cgt cat tgc cgt cgt tgc atg ata ttc gat      870
Gln Asp Phe Ala Asp Arg Arg His Cys Arg Arg Cys Met Ile Phe Asp
                    265                 270                 275 tgt cat atg cat gag aag tat gag ccc gag tct aga tcc agc gaa gac      918
Cys His Met His Glu Lys Tyr Glu Pro Glu Ser Arg Ser Ser Glu Asp
                280                 285                 290 aaa tct agt ttg ttt gag gat gaa gat aga caa cca tgc agt gag cat      966
Lys Ser Ser Leu Phe Glu Asp Glu Asp Arg Gln Pro Cys Ser Glu His
            295                 300                 305 tgt tac ctc aag gtg agg agt gtg aca gaa gct gat cat gtg atg gat     1014
Cys Tyr Leu Lys Val Arg Ser Val Thr Glu Ala Asp His Val Met Asp
        310                 315                 320 aat gat aac tct ata tca aac aag att gtg gtc tca gat cca aac aac     1062
Asn Asp Asn Ser Ile Ser Asn Lys Ile Val Val Ser Asp Pro Asn Asn
325                 330                 335                 340 act atg tgg acg cct gta gag aag gat ctt tac ttg aaa gga att gag     1110
Thr Met Trp Thr Pro Val Glu Lys Asp Leu Tyr Leu Lys Gly Ile Glu
                    345                 350                 355 ata ttt ggg aga aac agt tgt gat gtt gca tta aac ata ctt cgg ggg     1158
Ile Phe Gly Arg Asn Ser Cys Asp Val Ala Leu Asn Ile Leu Arg Gly
                360                 365                 370 ctt aag acg tgc cta gag att tac aat tac atg cgc gaa caa gat caa     1206
Leu Lys Thr Cys Leu Glu Ile Tyr Asn Tyr Met Arg Glu Gln Asp Gln
            375                 380                 385 tgt act atg tca tta gac ctt aac aaa act aca caa aga cac aat cag     1254
Cys Thr Met Ser Leu Asp Leu Asn Lys Thr Thr Gln Arg His Asn Gln
        390                 395                 400 gtt acc aaa aaa gta tct cga aaa agt agt agg tcg gtc cgc aaa aaa     1302
Val Thr Lys Lys Val Ser Arg Lys Ser Ser Arg Ser Val Arg Lys Lys
405                 410                 415                 420 tcg aga ctc cga aaa tat gct cgt tat ccg cct gct tta aag aaa aca     1350
Ser Arg Leu Arg Lys Tyr Ala Arg Tyr Pro Pro Ala Leu Lys Lys Thr
                    425                 430                 435 act agt gga gaa gct aag ttt tat aag cac tac aca cca tgc act tgc     1398
Thr Ser Gly Glu Ala Lys Phe Tyr Lys His Tyr Thr Pro Cys Thr Cys
                440                 445                 450 aag tca aaa tgt gga cag caa tgc cct tgt tta act cac gaa aat tgc     1446
Lys Ser Lys Cys Gly Gln Gln Cys Pro Cys Leu Thr His Glu Asn Cys
            455                 460                 465 tgc gag aaa tat tgc ggg tgc tca aag gat tgc aac aat cgc ttt gga     1494
Cys Glu Lys Tyr Cys Gly Cys Ser Lys Asp Cys Asn Asn Arg Phe Gly
        470                 475                 480 gga tgt aat tgt gca att ggc caa tgc aca aat cga caa tgt cct tgt     1542
Gly Cys Asn Cys Ala Ile Gly Gln Cys Thr Asn Arg Gln Cys Pro Cys
485                 490                 495                 500 ttt gct gct aat cgt gaa tgc gat cca gat ctt tgt cgg agt tgt cct     1590
Phe Ala Ala Asn Arg Glu Cys Asp Pro Asp Leu Cys Arg Ser Cys Pro
                    505                 510                 515 ctt agc tgt gga gat ggc act ctt ggt gag aca cca gtg caa atc caa     1638
Leu Ser Cys Gly Asp Gly Thr Leu Gly Glu Thr Pro Val Gln Ile Gln
                520                 525                 530 tgc aag aac atg caa ttc ctc ctt caa acc aat aaa aag att ctc att     1686
Cys Lys Asn Met Gln Phe Leu Leu Gln Thr Asn Lys Lys Ile Leu Ile
            535                 540                 545 gga aag tct gat gtt cat gga tgg ggt gca ttt aca tgg gac tct ctt     1734
```

-continued

```
Gly Lys Ser Asp Val His Gly Trp Gly Ala Phe Thr Trp Asp Ser Leu
            550                 555                 560 aaa aag aat gag tat ctc gga gaa tat act gga gaa ctg atc act cat    1782
Lys Lys Asn Glu Tyr Leu Gly Glu Tyr Thr Gly Glu Leu Ile Thr His
565                 570                 575                 580 gat gaa gct aat gag cgt ggg aga ata gaa gat cgg att ggt tct tcc    1830
Asp Glu Ala Asn Glu Arg Gly Arg Ile Glu Asp Arg Ile Gly Ser Ser
                585                 590                 595 tac ctc ttt acc ttg aat gat cag ctc gaa atc gat gct cgc cgt aaa    1878
Tyr Leu Phe Thr Leu Asn Asp Gln Leu Glu Ile Asp Ala Arg Arg Lys
            600                 605                 610 gga aac gag ttc aaa ttt ctc aat cac tca gca aga cct aac tgc tac    1926
Gly Asn Glu Phe Lys Phe Leu Asn His Ser Ala Arg Pro Asn Cys Tyr
615                 620                 625 gcc aag ttg atg att gtg aga gga gat cag agg att ggt cta ttt gcg    1974
Ala Lys Leu Met Ile Val Arg Gly Asp Gln Arg Ile Gly Leu Phe Ala
            630                 635                 640 gag aga gca atc gaa gaa ggt gag gag ctt ttc ttc gac tac tgc tat    2022
Glu Arg Ala Ile Glu Glu Gly Glu Glu Leu Phe Phe Asp Tyr Cys Tyr
645                 650                 655                 660 gga cca gaa cat gcg gat tgg tcg cgt ggt cga gaa cct aga aag act    2070
Gly Pro Glu His Ala Asp Trp Ser Arg Gly Arg Glu Pro Arg Lys Thr
                665                 670                 675 ggt gct tct aaa agg tct aag gaa gcc cgt cca gct cgt tagttttga      2119
Gly Ala Ser Lys Arg Ser Lys Glu Ala Arg Pro Ala Arg
            680                 685 tctgaggaga agcagca                                                  2136
```

```
<210> SEQ ID NO: 2
<211> LENGTH: 689
<212> TYPE: PRT
<213> ORGANISM: Arabidopsis sp.

<400> SEQUENCE: 2

Met Glu Lys Glu Asn His Glu Asp Asp Gly Glu Gly Leu Pro Pro Glu
1               5                   10                  15

Leu Asn Gln Ile Lys Glu Gln Ile Glu Lys Glu Arg Phe Leu His Ile
            20                  25                  30

Lys Arg Lys Phe Glu Leu Arg Tyr Ile Pro Ser Val Ala Thr His Ala
        35                  40                  45

Ser His His Gln Ser Phe Asp Leu Asn Gln Pro Ala Ala Glu Asp Asp
    50                  55                  60

Asn Gly Gly Asp Asn Lys Ser Leu Leu Ser Arg Met Gln Asn Pro Leu
65                  70                  75                  80

Arg His Phe Ser Ala Ser Ser Asp Tyr Asn Ser Tyr Glu Asp Gln Gly
                85                  90                  95

Tyr Val Leu Asp Glu Asp Gln Asp Tyr Ala Leu Glu Glu Asp Val Pro
            100                 105                 110

Leu Phe Leu Asp Glu Asp Val Pro Leu Leu Pro Ser Val Lys Leu Pro
        115                 120                 125

Ile Val Glu Lys Leu Pro Arg Ser Ile Thr Trp Val Phe Thr Lys Ser
    130                 135                 140

Ser Gln Leu Met Ala Glu Ser Asp Ser Val Ile Gly Lys Arg Gln Ile
145                 150                 155                 160

Tyr Tyr Leu Asn Gly Glu Ala Leu Glu Leu Ser Ser Glu Glu Asp Glu
                165                 170                 175

Glu Asp Glu Glu Glu Asp Glu Glu Glu Ile Lys Lys Glu Lys Cys Glu
```

```
                180             185             190
Phe Ser Glu Asp Val Asp Arg Phe Ile Trp Thr Val Gly Gln Asp Tyr
            195             200             205
Gly Leu Asp Asp Leu Val Val Arg Arg Ala Leu Ala Lys Tyr Leu Glu
        210             215             220
Val Asp Val Ser Asp Ile Leu Glu Arg Tyr Asn Glu Leu Lys Leu Lys
225             230             235             240
Asn Asp Gly Thr Ala Gly Glu Ala Ser Asp Leu Thr Ser Lys Thr Ile
            245             250             255
Thr Thr Ala Phe Gln Asp Phe Ala Asp Arg Arg His Cys Arg Arg Cys
                260             265             270
Met Ile Phe Asp Cys His Met His Glu Lys Tyr Glu Pro Glu Ser Arg
            275             280             285
Ser Ser Glu Asp Lys Ser Ser Leu Phe Glu Asp Glu Asp Arg Gln Pro
        290             295             300
Cys Ser Glu His Cys Tyr Leu Lys Val Arg Ser Val Thr Glu Ala Asp
305             310             315             320
His Val Met Asp Asn Asp Asn Ser Ile Ser Asn Lys Ile Val Val Ser
            325             330             335
Asp Pro Asn Asn Thr Met Trp Thr Pro Val Glu Lys Asp Leu Tyr Leu
            340             345             350
Lys Gly Ile Glu Ile Phe Gly Arg Asn Ser Cys Asp Val Ala Leu Asn
            355             360             365
Ile Leu Arg Gly Leu Lys Thr Cys Leu Glu Ile Tyr Asn Tyr Met Arg
        370             375             380
Glu Gln Asp Gln Cys Thr Met Ser Leu Asp Leu Asn Lys Thr Thr Gln
385             390             395             400
Arg His Asn Gln Val Thr Lys Lys Val Ser Arg Lys Ser Ser Arg Ser
            405             410             415
Val Arg Lys Lys Ser Arg Leu Arg Lys Tyr Ala Arg Tyr Pro Pro Ala
            420             425             430
Leu Lys Lys Thr Thr Ser Gly Glu Ala Lys Phe Tyr Lys His Tyr Thr
            435             440             445
Pro Cys Thr Cys Lys Ser Lys Cys Gly Gln Gln Cys Pro Cys Leu Thr
        450             455             460
His Glu Asn Cys Cys Glu Lys Tyr Cys Gly Cys Ser Lys Asp Cys Asn
465             470             475             480
Asn Arg Phe Gly Gly Cys Asn Cys Ala Ile Gly Gln Cys Thr Asn Arg
            485             490             495
Gln Cys Pro Cys Phe Ala Ala Asn Arg Glu Cys Asp Pro Asp Leu Cys
        500             505             510
Arg Ser Cys Pro Leu Ser Cys Gly Asp Gly Thr Leu Gly Glu Thr Pro
        515             520             525
Val Gln Ile Gln Cys Lys Asn Met Gln Phe Leu Leu Gln Thr Asn Lys
        530             535             540
Lys Ile Leu Ile Gly Lys Ser Asp Val His Gly Trp Gly Ala Phe Thr
545             550             555             560
Trp Asp Ser Leu Lys Lys Asn Glu Tyr Leu Gly Glu Tyr Thr Gly Glu
            565             570             575
Leu Ile Thr His Asp Glu Ala Asn Glu Arg Gly Arg Ile Glu Asp Arg
            580             585             590
Ile Gly Ser Ser Tyr Leu Phe Thr Leu Asn Asp Gln Leu Glu Ile Asp
        595             600             605
```

```
Ala Arg Arg Lys Gly Asn Glu Phe Lys Phe Leu Asn His Ser Ala Arg
        610             615                 620

Pro Asn Cys Tyr Ala Lys Leu Met Ile Val Arg Gly Asp Gln Arg Ile
625             630                 635                 640

Gly Leu Phe Ala Glu Arg Ala Ile Glu Glu Gly Glu Leu Phe Phe
            645                 650                 655

Asp Tyr Cys Tyr Gly Pro Glu His Ala Asp Trp Ser Arg Gly Arg Glu
            660                 665                 670

Pro Arg Lys Thr Gly Ala Ser Leu Arg Ser Lys Glu Ala Arg Pro Ala
        675                 680                 685

Arg

<210> SEQ ID NO: 3
<211> LENGTH: 1563
<212> TYPE: DNA
<213> ORGANISM: Arabidopsis sp.
<220> FEATURE:
<221> NAME/KEY: CDS
<222> LOCATION: (199)..(1308)
<223> OTHER INFORMATION: fertilization-independent endosperm 3 (FIE3)
      cDNA

<400> SEQUENCE: 3
aaaggtgagt tgtgtgttgt gtcaggtcca aaataaaagt ttgtcgtgag gtcaaaatct    60
acggttacag taatttaat aacctgtgaa tctgtgtcta atcgaaaatt acaaaacacc   120
agttgttgtt gcatgagaga cttgtgagct tagattagtg tgcgagagtc agacagagag   180
agagatttcg aatatcga atg tcg aag ata acc tta ggg aac gag tca ata    231
                     Met Ser Lys Ile Thr Leu Gly Asn Glu Ser Ile
                       1               5                      10 gtt ggg tct ttg act cca tcg aat aag aaa tcg tac aaa gtg acg aat    279
Val Gly Ser Leu Thr Pro Ser Asn Lys Lys Ser Tyr Lys Val Thr Asn
             15                  20                  25 agg att cag gaa ggg aag aaa cct ttg tat gct gtt gtt ttc aac ttc    327
Arg Ile Gln Glu Gly Lys Lys Pro Leu Tyr Ala Val Val Phe Asn Phe
         30                  35                  40 ctt gat gct cgt ttc ttc gat gtc ttc gtt acc gct ggt gga aat cgg    375
Leu Asp Ala Arg Phe Phe Asp Val Phe Val Thr Ala Gly Gly Asn Arg
     45                  50                  55 att act ctg tac aat tgt ctc gga gat ggt gcc ata tca gca ttg caa    423
Ile Thr Leu Tyr Asn Cys Leu Gly Asp Gly Ala Ile Ser Ala Leu Gln
 60                  65                  70                  75 tcc tat gct gat gaa gat aag gaa gag tcg ttt tac acg gta agt tgg    471
Ser Tyr Ala Asp Glu Asp Lys Glu Glu Ser Phe Tyr Thr Val Ser Trp
                 80                  85                  90 gcg tgt ggc gtt aat ggg aac cca tat gtt gcg gct gga gga gta aaa    519
Ala Cys Gly Val Asn Gly Asn Pro Tyr Val Ala Ala Gly Gly Val Lys
             95                 100                 105 ggt ata atc cga gtc att gac gtc aac agt gaa acg att cat aag agt    567
Gly Ile Ile Arg Val Ile Asp Val Asn Ser Glu Thr Ile His Lys Ser
         110                 115                 120 ctt gtg ggt cat gga gat tca gtg aac gaa atc agg aca caa cct tta    615
Leu Val Gly His Gly Asp Ser Val Asn Glu Ile Arg Thr Gln Pro Leu
     125                 130                 135 aaa cct caa ctt gtg att act gct agc aag gat gaa tct gtt cgt ttg    663
Lys Pro Gln Leu Val Ile Thr Ala Ser Lys Asp Glu Ser Val Arg Leu
140                 145                 150                 155 tgg aat gtt gaa act ggg ata tgt att ttg ata ttt gct gga gct gga    711
Trp Asn Val Glu Thr Gly Ile Cys Ile Leu Ile Phe Ala Gly Ala Gly
```

-continued

```
                      160                 165                 170
ggt cat cgc tat gaa gtt cta agt gtg gat ttt cat ccg tct gat att       759
Gly His Arg Tyr Glu Val Leu Ser Val Asp Phe His Pro Ser Asp Ile
                175                 180                 185 tac cgc ttt gct agt tgt ggt atg gac acc act att aaa ata tgg tca       807
Tyr Arg Phe Ala Ser Cys Gly Met Asp Thr Thr Ile Lys Ile Trp Ser
            190                 195                 200 atg aaa gag ttt tgg acg tac gtc gag aag tca ttc aca tgg act gat       855
Met Lys Glu Phe Trp Thr Tyr Val Glu Lys Ser Phe Thr Trp Thr Asp
        205                 210                 215 gat cca tca aaa ttc ccc aca aaa ttt gtc caa ttc cct gta ttt aca       903
Asp Pro Ser Lys Phe Pro Thr Lys Phe Val Gln Phe Pro Val Phe Thr
220                 225                 230                 235 gct tcc att cat aca aat tat gta gat tgt aac cgt tgg ttt ggt gat       951
Ala Ser Ile His Thr Asn Tyr Val Asp Cys Asn Arg Trp Phe Gly Asp
                240                 245                 250 ttt atc ctc tca aag agt gtg gac aac gag atc ctg ttg tgg gaa cca       999
Phe Ile Leu Ser Lys Ser Val Asp Asn Glu Ile Leu Leu Trp Glu Pro
            255                 260                 265 caa ctg aaa gag aat tct cct ggc gag gga gct tca gat gtt cta tta      1047
Gln Leu Lys Glu Asn Ser Pro Gly Glu Gly Ala Ser Asp Val Leu Leu
        270                 275                 280 aga tac ccg gtt cca atg tgt gat att tgg ttt atc aag ttt tct tgt      1095
Arg Tyr Pro Val Pro Met Cys Asp Ile Trp Phe Ile Lys Phe Ser Cys
285                 290                 295 gac ctc cat tta agt tct gtt gcg ata ggt aat cag gaa gga aag gtt      1143
Asp Leu His Leu Ser Ser Val Ala Ile Gly Asn Gln Glu Gly Lys Val
300                 305                 310                 315 tat gtc tgg gat ttg aaa agt tgc cct cct gtt ttg att aca aag tta      1191
Tyr Val Trp Asp Leu Lys Ser Cys Pro Pro Val Leu Ile Thr Lys Leu
                320                 325                 330 tca cac aat caa tca aag tct gta atc agg caa aca gcc atg tct gtc      1239
Ser His Asn Gln Ser Lys Ser Val Ile Arg Gln Thr Ala Met Ser Val
            335                 340                 345 gat gga agc acg att ctt gct tgc tgc gag gac ggg act ata tgg cgc      1287
Asp Gly Ser Thr Ile Leu Ala Cys Cys Glu Asp Gly Thr Ile Trp Arg
        350                 355                 360 tgg gac gtg att acc aag tagcggtctg agtcttgtag gaattgatga            1335
Trp Asp Val Ile Thr Lys
            365 attaggagtg cgaagaaatg agatatccat tcttttattg taattctgat catgttgcta    1395 ctccctgaga ccttgagatg ctctttgtag ccttgttaac gtccaccctt gtaccacagt    1455 gtataccctt tctggagatt ttgtcttatt ctcttagttc aatacacaag gctgtatcct    1515 ggagctttat tgcaggaacc actctctttc ataagctttc tagtattc                 1563
```

<210> SEQ ID NO: 4
<211> LENGTH: 369
<212> TYPE: PRT
<213> ORGANISM: Arabidopsis sp.

<400> SEQUENCE: 4

```
Met Ser Lys Ile Thr Leu Gly Asn Glu Ser Ile Val Gly Ser Leu Thr
 1               5                  10                  15

Pro Ser Asn Lys Lys Ser Tyr Lys Val Thr Asn Arg Ile Gln Glu Gly
            20                  25                  30

Lys Lys Pro Leu Tyr Ala Val Val Phe Asn Phe Leu Asp Ala Arg Phe
        35                  40                  45
```

-continued

```
Phe Asp Val Phe Val Thr Ala Gly Gly Asn Arg Ile Thr Leu Tyr Asn
     50                  55                  60

Cys Leu Gly Asp Gly Ala Ile Ser Ala Leu Gln Ser Tyr Ala Asp Glu
 65                  70                  75                  80

Asp Lys Glu Glu Ser Phe Tyr Thr Val Ser Trp Ala Cys Gly Val Asn
                 85                  90                  95

Gly Asn Pro Tyr Val Ala Ala Gly Val Lys Gly Ile Ile Arg Val
                100                 105                 110

Ile Asp Val Asn Ser Glu Thr Ile His Lys Ser Leu Val Gly His Gly
            115                 120                 125

Asp Ser Val Asn Glu Ile Arg Thr Gln Pro Leu Lys Pro Gln Leu Val
    130                 135                 140

Ile Thr Ala Ser Lys Asp Glu Ser Val Arg Leu Trp Asn Val Glu Thr
145                 150                 155                 160

Gly Ile Cys Ile Leu Ile Phe Ala Gly Ala Gly Gly His Arg Tyr Glu
                165                 170                 175

Val Leu Ser Val Asp Phe His Pro Ser Asp Ile Tyr Arg Phe Ala Ser
            180                 185                 190

Cys Gly Met Asp Thr Thr Ile Lys Ile Trp Ser Met Lys Glu Phe Trp
    195                 200                 205

Thr Tyr Val Glu Lys Ser Phe Thr Trp Thr Asp Pro Ser Lys Phe
210                 215                 220

Pro Thr Lys Phe Val Gln Phe Pro Val Phe Thr Ala Ser Ile His Thr
225                 230                 235                 240

Asn Tyr Val Asp Cys Asn Arg Trp Phe Gly Asp Phe Ile Leu Ser Lys
                245                 250                 255

Ser Val Asp Asn Glu Ile Leu Leu Trp Glu Pro Gln Leu Lys Glu Asn
            260                 265                 270

Ser Pro Gly Glu Gly Ala Ser Asp Val Leu Leu Arg Tyr Pro Val Pro
    275                 280                 285

Met Cys Asp Ile Trp Phe Ile Lys Phe Ser Cys Asp Leu His Leu Ser
290                 295                 300

Ser Val Ala Ile Gly Asn Gln Glu Gly Lys Val Tyr Val Trp Asp Leu
305                 310                 315                 320

Lys Ser Cys Pro Pro Val Leu Ile Thr Lys Leu Ser His Asn Gln Ser
                325                 330                 335

Lys Ser Val Ile Arg Gln Thr Ala Met Ser Val Asp Gly Ser Thr Ile
            340                 345                 350

Leu Ala Cys Cys Glu Asp Gly Thr Ile Trp Arg Trp Asp Val Ile Thr
    355                 360                 365

Lys
```

```
<210> SEQ ID NO: 5
<211> LENGTH: 5801
<212> TYPE: DNA
<213> ORGANISM: Arabidopsis sp.
<220> FEATURE:
<221> NAME/KEY: CDS
<222> LOCATION: (3872)..(5566)
<223> OTHER INFORMATION: fertilization-independent endosperm 3 (FIE3)
      WD40/polycomb gene genomic sequence

<400> SEQUENCE: 5
tctgaagcag ctaatcgatc cactaatctt gtggagatcg tgtgttgctt tggtgcatat      60
atatacaaat agacaaatac atatgcgttt acatatatat gtaagcacgt atttagagag     120
```

-continued

```
caacaataag gcatgagaaa tgtgattatc gtcaaatcat gattgctaca tgacaaatcg      180 atcttaatttt tgaaaaagag acatttaaat attcaaaaaa cggtaaaaat ttctttaaga     240
ccaaccatgg aaataacatg agaagactga gagggagatt agaacttaca acaagagaat     300 cttttcctt caatatttt tttaaacact tttctttgt agggaatttg ataatatgaa        360
atggatagat tttactgctt aattttaat catttttat cagaaactt ttcgttttaa        420 atctacggct agaattttcg gtcggttta tactttatat agatgctaga ttttttttctt     480 ctagtcatcg tttattagta caattttgtt tttatatatt gattacttga atttataata     540
ggattggtac aaaggtggta attataaagt gcattttttt ggatattgtt caattcaaat     600
atttttactt agattctcaa actattgaaa aatatccaaa atatccggaa aatttcaatt     660
taatcgaata aaaaaattag aatggaaaga ataaaaaatt atcgggtaca attagaagag     720
taatgtgttt agtttggttt ttactcggat accagttcag ttttcacgta ttattcgatc     780
ctataggagc aattgtgaat tagttgtgag attttgggag cattcgcttc cagaacttag     840
tgctaggaga aatgctattt tcctataaga gttgtacgag gaagcgagca agtacacaac     900
aaccacaaaa gctttcaata cttgtttact cctagggttt aaaactagag gttctataga     960
tctctaaatt tttttgaaca aatgtgtttt ccacacgtga tattctacaa taccactcga    1020
aaattatcca taattgcttt aaactatttt tttgttttaaa ttatataatt tgtaccgttg    1080
taaactgatt atttcaaatt ataattaaag cactataatt tcatatatta cattcaacat    1140
atattaaaat aaactataac catgtatttt tttgtcttcc tttcctataa acattgattg    1200
gactctatcg taaattttgt cgttatcgca aattttgtcg ttatcgatga gtttctcaaa    1260
gtttggacct tgattatctt gtttggagat gttcaaatcg ttatatccaa atagtgaact    1320
tctaattttc ttttttgata atgtgactta tttggaaaag tattccaaag tattcaaata    1380 aacccttta aaatccatta aatacatttt aaataagtaa aatgctctca acgaagagat    1440
atcatggtaa ataacaacag tgagaggata aaatgttaaa tcaatttatt tacaacttca    1500
aataggcgga catcaaaacct acttagcaca cttttctattt tcaaattggt tatggttttgt   1560 ctattagttg ttgcatctat gtttttttaat tcttatatcg gtgatcttga ttttgtttg    1620 gtgtatctaa aatctatttt agttaaagtg caagaaaata aaataaaaac ttaaggtaag    1680
agatgaaagt aagctttaaa taaaacagag cacttctatg gtcgattata gagccaagtt    1740
cgttcctcca ttttggctta atgcaatatt acaagtaaat cttataaaac tttccataag    1800
tatcgtatta cccatggata ctatgatata taaactctcg gaggtgtagt ccagaagaaa    1860
tgatccatat ttgcatacag taaacttgat ggaaaaaata tgtggtactg ttggaattgt    1920
agctattgag tatcaaattt gagaaaaagg taaaaaaata tgtaaaattt gggtggaaga    1980
aaagaattac ataaaattga gaaatgtatg taattgacaa ataatgtttt tcaaaacata    2040
aaaacgtgat accatttaaa tccaaacctt atatcattta accatttta gtaaaactaa    2100 tagtaatgaa tggtcaataa tataagatta catattaaat aattactact ttcagaaaat    2160
ttcaatcaaa tctataatat tcctttgaaa aaaagaaag acaaataggt aaacttcgat    2220
cgtatcaatc aaagaatata tttattttc atcgtaacgt ttaattctaa gtcctattaa    2280
aaaacgttaa atttgatttt tcttaccatt tttttctaaa aggtgagttg tgtgttgtgt    2340
caggtccaaa ataaaagttt gtcgtgaggt caaaatctac ggttacagta atttttaataa   2400 cctgtgaatc tgtgtctaat cgaaaattac aaaacaccag ttgttgttgc atgagagact    2460
tgtgagctta gattagtgtg cgagagtcag acagagagag agatttcgaa tatcgaatgt    2520
```

```
cgaagataac cttagggaac gagtcaatag ttgggtcttt gactccatcg aataagaaat    2580
cgtacaaagt gacgaatagg attcaggaag ggaagaaacc tttgtatgct gttgttttca    2640
acttccttga tgctcgtttc ttcgatgtct tcgttaccgc tggtggaaat cgggtaaaag    2700
atctcgactt tcaattcgaa atcactgttt tcaattctgg gtctgtttag gttttgattc    2760
agattgattg taacattaag gcctttcctt ttgtgtttga ttttggattc tgatttctag    2820
cctttagtga gattaaaaga ttgaaacttt gcttgatgct atagtctaag attatgtaac    2880
atttagttca aactttctgg ttttggagat tttgtggaag atatggtttt tgttttctaa    2940
tttaaagtga actcattacc ttatacactt gatttgcatt ctgttctaaa aaaaattgaa    3000
actttggttg atgttgttag tctgcttatc taaggaggtc ccttttgaaa cggtcatcaa    3060
gtgagttatg aagcgtttag tttaagcttt cctgtattgg agattttgtg gaagttattt    3120 tttttttctaa ttttgaaact agatagagtg aagtcattac cttatacatt agactgctct    3180
attttgtttt caatgtgggt tccgaatgta cctgatagtg gctctttagg ctcatttgta    3240
ttcgtcgaaa catcgatcgg atacccgttt gggcttagta ggctctgata ccgcgtaaag    3300
ttctcgggtt ccatgaaaaa ccaatcggta atgagtggag ttaatttgta atcgtcttcg    3360
gtcgagcatt tgggattagt gggctttgat accatgtgaa agtccttggg gtccaatcgg    3420
caatgagtag agttaacttg taatcttaca cacttggtta ggtctcattc tctttataat    3480
gttgtgtgcc taacagtttc cgcactaagg ttgtttggtt gctcagtctc aatatactta    3540
tcttaactag ttgtagtttt tttcatcttt cctagtttcc gttggatttt aaattgaatg    3600
atttactagt tagaaatatt tgagtttctc atagaagctt taaccaaggg gttctttcat    3660
ttaaccttta cttagctagt tcatgaatct cattactgcc attggtgtat ctcttattat    3720
gtagattact ctgtacaatt gtctcggaga tggtgccata tcagcattgc aatcctatgc    3780
tgatgaagat gtaaggaagc atacatatta gcttttccat caaattaaag taagtgatgt    3840
ttcactgagg ccatttggtt atattttgtc tatgtcctct ggagagcaga aggaagagtc    3900
gttttacacg gtaagttggg cgtgtggcgt taatgggaac ccatatgttg cggctggagg    3960
agtaaaaggt ataatccgag tcattgacgt caacagtgaa acgattcata aggtattatt    4020 gcattttat ggatgttcta tgtatcctag caaatgattc tatatctttc ttgtataatc    4080
tgtgctcgca aatgtgcaga gtcttgtggg tcatggagat tcagtgaacg aaatcaggac    4140 acaacccttta aaacctcaac ttgtgattac tgctagcaag gtatatctct ggctttctt    4200 ttcttcctaa agtatcctga cttctttttt atttgttggt gattaagagc tgttacgttt    4260
taattgaata aggatgaatc tgttcgtttg tggaatgttg aaactgggat atgtattttg    4320
atatttgctg gagctggagg tcatcgctat gaagttctaa gtgtggtgag ccaatattgt    4380
tttatctaat tcagttagtt ttctacaata atatatagag acaatgttaa ggggaaccat    4440 cttatttttga aaattgtagg attttcatcc gtctgatatt taccgctttg ctagttgtgg    4500
tatggacacc actattaaaa tatggtcaat gaaaggtacg atcgagcaca tattgtaata    4560
aacttccatt ttaaaaaacc ttttgagaaa aatggcttgt ggttcgtttg tatgatcttc    4620
ttattctttg gctgtctata gagttttgga cgtacgtcga gaagtcattc acatggactg    4680
atgatccatc aaaattcccc acaaaatttg tccaattccc tgtaagtatt tgttttagc    4740 cttgtcttgt aacaacaagt gacatacaaa tattggtgat ggcctttgta aataacatta    4800
cttctatatg taggtatttta cagcttccat tcatacaaat tatgtagatt gtaaccgttg    4860
```

-continued

```
gtttggtgat tttatcctct caaaggttag taagtcaatg atggttaaga ttaattcatt    4920
tggtgtactg ttaaaacact ttactcttgt gttgttctat cggattttag agtgtggaca    4980
acgagatcct gttgtgggaa ccacaactga aagagaattc tcctggcgag gttaggatct    5040
cattgttgct ccaaacacaa cataatcatt catttcatca catatattta cagttgaact    5100
ttttgtggtt tgcagggagc ttcagatgtt ctattaagat acccggttcc aatgtgtgat    5160
atttggttta tcaagttttc ttgtgacctc catttaagtt ctgttgcgat aggtaatcag    5220
agagctcgtt agatacaaat ttgcattcta tagatagatt acttcaactt ttcttattca    5280
ttttgtgaca aattactcgc tggtttgtta tcaggtaatc aggaaggaaa ggtttatgtc    5340
tgggatttga aaagttgccc tcctgttttg attacaaagt aagttagttt cggattcaga    5400
tacaatgttt gatctttaag aaatgtttta gtcttgacat gattttctgt tgccatatag    5460
gttatcacac aatcaatcaa agtctgtaat caggcaaaca gccatgtctg tcgatggaag    5520
gtataaatcc atcttctctc tcaccaatgc agtgaaaatt tcttaatgtt atttatgact    5580
caatagttac tgtaaatcaa accaaacttt ggattctgac acactgtttc ttccatggga    5640
ttgtagcacg attcttgctt gctgcgagga cgggactata tggcgctggg acgtgattac    5700
caagtagcgg tctgagtctt gtaggaattg atgaattagg agtgcgaaga aatgagatat    5760
ccattctttt attgtaattc tgatcatgtt gctactccct g                        5801
```

<210> SEQ ID NO: 6
<211> LENGTH: 7015
<212> TYPE: DNA
<213> ORGANISM: Arabidopsis sp.
<220> FEATURE:
<221> NAME/KEY: CDS
<222> LOCATION: (1)..(7014)
<223> OTHER INFORMATION: fertilization-independent endosperm 1 (FIE1) SET/polycomb gene genomic sequence reading frame 1
<220> FEATURE:
<221> NAME/KEY: CDS
<222> LOCATION: (2)..(7015)
<223> OTHER INFORMATION: fertilization-independent endosperm 1 (FIE1) SET/polycomb gene genomic sequence reading frame 2
<220> FEATURE:
<221> NAME/KEY: CDS
<222> LOCATION: (3)..(7013)
<223> OTHER INFORMATION: fertilization-independent endosperm 1 (FIE1) SET/polycomb gene genomic sequence reading frame 3

<400> SEQUENCE: 6

```
gga tcc att att ttt aaa aat caa att ttt tca tat cta tta ttt gtt     48
Gly Ser Ile Ile Phe Lys Asn Gln Ile Phe Ser Tyr Leu Leu Phe Val
 1               5                  10                  15 tca aag aaa aaa aaa aca cac gac gat tat cca tct gcc ggc tgt gtt    96
Ser Lys Lys Lys Lys Thr His Asp Asp Tyr Pro Ser Ala Gly Cys Val
             20                  25                  30 cat cgg taa acc tat att tta aaa ctg gtg ggc ttt tca tta cca taa   144
His Arg     Thr Tyr Ile Leu Lys Leu Val Gly Phe Ser Leu Pro
         35                  40                  45 gtt tgg aca tgt ttt tat aat ttg atg tat agt gta gac caa aaa ata   192
Val Trp Thr Cys Phe Tyr Asn Leu Met Tyr Ser Val Asp Gln Lys Ile
 50                  55                  60 gag aaa taa gaa agg gaa cct ttg tgg tga ttg taa caa aac aga aat   240
Glu Lys     Glu Arg Glu Pro Leu Trp     Leu     Gln Asn Arg Asn
 65                  70                  75                  80 cat tat att gaa tca ttc gaa aag acg aaa aga tca aac ctt tgt agc   288
His Tyr Ile Glu Ser Phe Glu Lys Thr Lys Arg Ser Asn Leu Cys Ser
                 85                  90                  95
```

-continued

```
tag atg acc ata gac gtg gct gcc aat tac agt ctt aat gct ttt ata      336
    Met Thr Ile Asp Val Ala Ala Asn Tyr Ser Leu Asn Ala Phe Ile
        100                 105                 110 tag atc ttt ctt aca tcc tct gtt cct tca cat tca aga aac agt atc      384
    Ile Phe Leu Thr Ser Ser Val Pro Ser His Ser Arg Asn Ser Ile
            115                 120                 125 atc cca ttt tct ttc ttc ttc tca gtg ttt caa tct ttg cga att aag      432
Ile Pro Phe Ser Phe Phe Phe Ser Val Phe Gln Ser Leu Arg Ile Lys
130                 135                 140 atg gaa cat gaa gaa aca caa aag aac aca aga aac agc tgg tcc ctg      480
Met Glu His Glu Glu Thr Gln Lys Asn Thr Arg Asn Ser Trp Ser Leu
145                 150                 155                 160 att cga cca ttt caa atg atc tcc att agc ttt ctt agc ctc ctc ctc      528
Ile Arg Pro Phe Gln Met Ile Ser Ile Ser Phe Leu Ser Leu Leu Leu
                165                 170                 175 cct cta tct ttc ctc ttt ctt tca cgt ctc tct ctc tat acc tcc tca      576
Pro Leu Ser Phe Leu Phe Leu Ser Arg Leu Ser Leu Tyr Thr Ser Ser
            180                 185                 190 act ccg gtc acc gtc tcc ggc gtt tcc tct gtt att cac cag gca gat      624
Thr Pro Val Thr Val Ser Gly Val Ser Ser Val Ile His Gln Ala Asp
        195                 200                 205 gtc gga gtc tta tac acg atc ttg ttt ctc atc atc gtc ttc act tta      672
Val Gly Val Leu Tyr Thr Ile Leu Phe Leu Ile Ile Val Phe Thr Leu
210                 215                 220 atc cac agt ctc tca gga aaa cca gaa tgc tct gtt ctc cat tcc cat      720
Ile His Ser Leu Ser Gly Lys Pro Glu Cys Ser Val Leu His Ser His
225                 230                 235                 240 ctc tac atc tgc tgg atc gtt ctc ttc atc gcc caa gct tgt gcc ttt      768
Leu Tyr Ile Cys Trp Ile Val Leu Phe Ile Ala Gln Ala Cys Ala Phe
                245                 250                 255 ggg atc aaa aga acc atg agc acg acc atg tct ata aat cca gac aaa      816
Gly Ile Lys Arg Thr Met Ser Thr Thr Met Ser Ile Asn Pro Asp Lys
            260                 265                 270 aac ttg ttt ctt gcg aca cat gaa aga tgg atg ttg gtt agg gtt ttg      864
Asn Leu Phe Leu Ala Thr His Glu Arg Trp Met Leu Val Arg Val Leu
        275                 280                 285 ttc ttt ttg ggg cta cac gaa gtg atg ctg atg tgg ttt aga gtc gtg      912
Phe Phe Leu Gly Leu His Glu Val Met Leu Met Trp Phe Arg Val Val
290                 295                 300 gtt aag cct gtg gtt gac aac act ata tat ggg gtc tac gtg gag gag      960
Val Lys Pro Val Val Asp Asn Thr Ile Tyr Gly Val Tyr Val Glu Glu
305                 310                 315                 320 agg tgg tcc gag aga gcc gtt gtg gca gtg acc ttt ggt ata atg tgg     1008
Arg Trp Ser Glu Arg Ala Val Val Ala Val Thr Phe Gly Ile Met Trp
                325                 330                 335 tgg tgg agg cta aga gat gag gta gaa agt ctt gtg gtg gtt acg          1056
Trp Trp Arg Leu Arg Asp Glu Val Glu Ser Leu Val Val Val Thr
            340                 345                 350 gcg gat aga ctt aac ctc ccc att cgt ttg gag ggt ctc aat ttt gtg     1104
Ala Asp Arg Leu Asn Leu Pro Ile Arg Leu Glu Gly Leu Asn Phe Val
        355                 360                 365 aac tgg tgt atg tat tac atc tgt gtt gga att ggt tta atg aag atc     1152
Asn Trp Cys Met Tyr Tyr Ile Cys Val Gly Ile Gly Leu Met Lys Ile
370                 375                 380 ttc aaa ggg ttt ttg gat ttt gtg aat acg ttg act ttg agc att aag     1200
Phe Lys Gly Phe Leu Asp Phe Val Asn Thr Leu Thr Leu Ser Ile Lys
385                 390                 395                 400 agg tcg aga aaa ggc tgt gaa tca tgt gtt ttt gat gat atg tgt aat     1248
Arg Ser Arg Lys Gly Cys Glu Ser Cys Val Phe Asp Asp Met Cys Asn
                405                 410                 415
```

-continued

```
gat gat cat gtg taa gat att tga cat att ata ctc atc tct tga atg    1296
Asp Asp His Val     Asp Ile     His Ile Ile Leu Ile Ser     Met
            420                 425                 430 ttt ttg aga ttt ttt tat ttt tat ttt cta ttt ctt gct agg aat tta    1344
Phe Leu Arg Phe Phe Tyr Phe Tyr Phe Leu Phe Leu Ala Arg Asn Leu
            435                 440                 445 acc cgt ata tat gtc aca aaa ata gta gaa tat cag aaa gca aaa ata    1392
Thr Arg Ile Tyr Val Thr Lys Ile Val Glu Tyr Gln Lys Ala Lys Ile
            450                 455                 460 ttt tat cta aaa ata acc att gaa cat taa ttt aag tct ttt tat aat    1440
Phe Tyr Leu Lys Ile Thr Ile Glu His     Phe Lys Ser Phe Tyr Asn
465                 470                 475                 480 tat att ttt ata aca cac cct ttt taa gaa aaa ctt gga gat tta att    1488
Tyr Ile Phe Ile Thr His Pro Phe     Glu Lys Leu Gly Asp Leu Ile
            485                     490                 495 aac gtt ata aat agt aaa aaa tat cgg att tac gta gaa gtt tta aat    1536
Asn Val Ile Asn Ser Lys Lys Tyr Arg Ile Tyr Val Glu Val Leu Asn
            500                 505                 510 gcg tat aat taa att tac gaa ttg aat aat ata gcc ata tat ata ttt    1584
Ala Tyr Asn     Ile Tyr Glu Leu Asn Asn Ile Ala Ile Tyr Ile Phe
            515                 520                 525 ttg aag att taa act cat ttt gtt tct tcc ata tat gca taa tat ata    1632
Leu Lys Ile     Thr His Phe Val Ser Ser Ile Tyr Ala     Tyr Ile
530                 535                 540 agc tta aat aga aaa cta gct agg aat gaa tac taa tat ata taa tga    1680
Ser Leu Asn Arg Lys Leu Ala Arg Asn Glu Tyr     Tyr Ile
545                 550                 555                     560 cat taa tat aag tct tac cgg aca ctc caa aat gta tat att gat cta    1728
His     Tyr Lys Ser Tyr Arg Thr Leu Gln Asn Val Tyr Ile Asp Leu
            565                 570                 575 tca aca ttt ttt cat tgg ttt act aaa cca agt tgt cac ata aat atg    1776
Ser Thr Phe Phe His Trp Phe Thr Lys Pro Ser Cys His Ile Asn Met
            580                 585                 590 agt taa cgc ctt ttt ttt tat aat att gta tat gaa ttt aaa ctt gag    1824
Ser     Arg Leu Phe Phe Tyr Asn Ile Val Tyr Glu Phe Lys Leu Glu
            595                 600                 605 ctg tca aac gtc aag caa acc caa cat cta cat aca tat agt act ata    1872
Leu Ser Asn Val Lys Gln Thr Gln His Leu His Thr Tyr Ser Thr Ile
610                 615                 620 ttt tga aaa tta aaa ttt tct taa att tcc cat att att ttc ctt tta    1920
Phe     Lys Leu Lys Phe Ser     Ile Ser His Ile Ile Phe Leu Leu
625                 630                 635                 640 aag caa gca agt cca aat acg ttt ctt cca gat tat aat ttt cct taa    1968
Lys Gln Ala Ser Pro Asn Thr Phe Leu Pro Asp Tyr Asn Phe Pro
            645                 650                 655 taa ggt ttt cta caa aaa aaa atc aac ttc tta ttt aaa aaa ccc ttt    2016
    Gly Phe Leu Gln Lys Lys Ile Asn Phe Leu Phe Lys Lys Pro Phe
            660                 665                 670 gca tta tcc ttt tca cca aca tca gag aag acg aga aaa aaa gaa gag    2064
Ala Leu Ser Phe Ser Pro Thr Ser Glu Lys Thr Arg Lys Lys Glu Glu
            675                 680                 685 gcg agt ggt taa tgg aga agg tta gtt tca ctc caa aca tat atg aat    2112
Ala Ser Gly     Trp Arg Arg Leu Val Ser Leu Gln Thr Tyr Met Asn
690                 695                 700 tga cta ggt tat gaa atc cat ata ttt taa ttg tgt gtt tat gat aga    2160
    Leu Gly Tyr Glu Ile His Ile Phe     Leu Cys Val Tyr Asp Arg
    705                 710                 715                 720 tca ata aca ttt agg gtt gaa ttt tct tgt gat cta tta tgt tat tcg    2208
Ser Ile Thr Phe Arg Val Glu Phe Ser Cys Asp Leu Leu Cys Tyr Ser
```

-continued

|     | 725 |     |     |     | 730 |     |     |     | 735 |     |     |     |     |     |      |
|-----|-----|-----|-----|-----|-----|-----|-----|-----|-----|-----|-----|-----|-----|-----|------|
| tcc | cat | gca | tga | tcc | ata | aaa | ctt | tta | ttt | ttg | aat | ttg | tct | agg | aaa  | 2256
| Ser | His | Ala |     | Ser | Ile | Lys | Leu | Leu | Phe | Leu | Asn | Leu | Ser | Arg | Lys  |
|     |     |     | 740 |     |     |     | 745 |     |     |     |     | 750 |     |     |      | acc atg agg acg atg gtg agg gtt tgc cac ccg aac taa atc aga taa     2304
Thr Met Arg Thr Met Val Arg Val Cys His Pro Asn     Ile Arg
        755                 760             765 aag agc aaa tcg aaa agg aga gat ttc tgc ata tca agg taa gag aca     2352
Lys Ser Lys Ser Lys Arg Arg Asp Phe Cys Ile Ser Arg     Glu Thr
    770             775             780 ttt ggt tgc ttt aat att tta ttc tct tct gta tgt ttt tct gaa aat     2400
Phe Gly Cys Phe Asn Ile Leu Phe Ser Ser Val Cys Phe Ser Glu Asn
785             790             795                 800 taa gga gag gag agg act aa  tct cat aac tat acg att cca aag aga     2448
    Gly Glu Glu Arg Thr     Ser His Asn Tyr Thr Ile Pro Lys Arg
                    805         810             815 tgt taa gat aca tct aat aaa cag tta tac att agt cat aat ctt taa     2496
Cys     Asp Thr Ser Asn Lys Gln Leu Tyr Ile Ser His Asn Leu
            820             825             830 aac taa aaa gag aaa ttt cca aac ttt taa att aaa aac aga att tag     2544
Asn     Lys Glu Lys Phe Pro Asn Phe     Ile Lys Asn Arg Ile
        835             840             845 aaa atg cca gcg aat cga taa cga cat cca gat ctg tcg ggt atc caa     2592
Lys Met Pro Ala Asn Arg     Arg His Pro Asp Leu Ser Gly Ile Gln
850             855             860 aac tta gaa taa aaa aat aat taa tat att tat aat ata aag ctg gaa     2640
Asn Leu Glu     Lys Asn Asn     Tyr Ile Tyr Asn Ile Lys Leu Glu
865             870             875             880 ctt agg tta taa aat aaa att gaa aat aat agt aga ttt ttt tgt ttt     2688
Leu Arg Leu     Asn Lys Ile Glu Asn Asn Ser Arg Phe Phe Cys Phe
                885             890             895 tgt caa aca aaa tag taa tac aat ttg ttt ttt tta gta caa aga aac     2736
Cys Gln Thr Lys     Tyr Asn Leu Phe Phe Leu Val Gln Arg Asn
            900             905             910 taa ata ggt cca aat tgt ttt ttt ttt aac att cag cca aaa aag cca     2784
    Ile Gly Pro Asn Cys Phe Phe Phe Asn Ile Gln Pro Lys Lys Pro
    915             920             925 aga ttg atg cat ata tca aga aat cga aat caa aac ttt tgt att caa     2832
Arg Leu Met His Ile Ser Arg Asn Arg Asn Gln Asn Phe Cys Ile Gln
930             935             940 gta ttc tag ttt cac tat ata tag agt cca gtt tct gaa att taa aaa     2880
Val Phe     Phe His Tyr Ile     Ser Pro Val Ser Glu Ile     Lys
945         950             955             960 atc att tac cta tat att act tga tta aca gag aaa att cga gct gag     2928
Ile Ile Tyr Leu Tyr Ile Thr     Leu Thr Glu Lys Ile Arg Ala Glu
            965                 970             975 ata cat tcc aag tgt ggc tac tca tgc ttc aca cca tca atc gtt tga     2976
Ile His Ser Lys Cys Gly Tyr Ser Cys Phe Thr Pro Ser Ile Val
        980             985             990 ctt aaa cca gcc cgc tgc aga gga tga taa tgg agg aga caa caa atc     3024
Leu Lys Pro Ala Arg Cys Arg Gly     Trp Arg Arg Gln Gln Ile
    995             1000                1005 act ttt gtc gag aat gca aaa ccc act tcg tca ttt cag tgc ctc atc     3072
Thr Phe Val Glu Asn Ala Lys Pro Thr Ser Ser Phe Gln Cys Leu Ile
    1010            1015            1020 tga tta taa ttc tta cga aga tca agg tta tgt tct tga tga gga tca     3120
    Leu     Phe Leu Arg Arg Ser Arg Leu Cys Ser     Gly Ser
1025            1030            1035            1040 aga tta tgc tct tga aga aga tgt acc att att tct tga tga aga tgt     3168

```
                                -continued

Arg Leu Cys Ser     Arg Arg Cys Thr Ile Ser         Arg Cys
            1045                1050                    1055 acc att att acc aag tgt caa gct tcc aat tgt tga gaa gct acc acg    3216
Thr Ile Ile Thr Lys Cys Gln Ala Ser Asn Cys     Glu Ala Thr Thr
        1060                1065                1070 atc cat tac atg ggt ctt cac caa aag gca tgt gtg ttt ttt gtt tcg    3264
Ile His Tyr Met Gly Leu His Gln Lys Ala Cys Val Phe Phe Val Ser
        1075                1080                1085 tac tag ttt caa aat att aat cat ata cta tat agt aat cac tca tag    3312
Tyr     Phe Gln Asn Ile Asn His Ile Leu Tyr Ser Asn His Ser
    1090                1095                1100 tgc ata tat aca ttt ctt taa cat tgc agt agc cag ctg atg gct gaa    3360
Cys Ile Tyr Thr Phe Leu     His Cys Ser Ser Gln Leu Met Ala Glu
1105                1110                1115                1120 agt gat tct gtg att ggt aag aga caa atc tat tat ttg aat ggt gag    3408
Ser Asp Ser Val Ile Gly Lys Arg Gln Ile Tyr Tyr Leu Asn Gly Glu
            1125                1130                1135 gca cta gaa ttg agc agt gaa gaa gat gag gaa gat gaa gaa gaa gat    3456
Ala Leu Glu Leu Ser Ser Glu Glu Asp Glu Glu Asp Glu Glu Glu Asp
            1140                1145                1150 gag gaa gaa atc aag aaa gaa aaa tgc gaa ttt tct gaa gat gta gac    3504
Glu Glu Glu Ile Lys Lys Glu Lys Cys Glu Phe Ser Glu Asp Val Asp
        1155                1160                1165 cga ttt ata tgg tta gtt ttt gca tta cat atg ttc ttg att att aat    3552
Arg Phe Ile Trp Leu Val Phe Ala Leu His Met Phe Leu Ile Ile Asn
        1170                1175                1180 ttg tag tcc ata ttt aat aaa ctg ctc aag aaa ttt tca gga cgg ttg    3600
Leu     Ser Ile Phe Asn Lys Leu Leu Lys Lys Phe Ser Gly Arg Leu
1185                1190                1195                1200 ggc agg act atg gtt tgg atg atc tgg tcg tgc ggc gtg ctc tcg cca    3648
Gly Arg Thr Met Val Trp Met Ile Trp Ser Cys Gly Val Leu Ser Pro
            1205                1210                1215 agt acc tcg aag tgg atg ttt cgg aca tat tgg taa caa tat tcg aat    3696
Ser Thr Ser Lys Trp Met Phe Arg Thr Tyr Trp     Gln Tyr Ser Asn
            1220                1225                1230 aaa aac ttc ata cgt cga tca ata act ttc ctg ctt att taa ttt ttg    3744
Lys Asn Phe Ile Arg Arg Ser Ile Thr Phe Leu Leu Ile     Phe Leu
        1235                1240                1245 ttg ttt ttc gtc gtg aga aat gtt tta aat ttt caa atc taa tgt agg    3792
Leu Phe Val Val Arg Asn Val Leu Asn Phe Gln Ile     Cys Arg
        1250                1255                1260 aaa gat aca atg aac tca agc tta aga atg atg gaa ctg ctg gtg agg    3840
Lys Asp Thr Met Asn Ser Ser Leu Arg Met Met Glu Leu Leu Val Arg
1265                1270                1275                1280 ctt ctg att tga cat cca aga caa taa cta ctg ctt tcc agg att ttg    3888
Leu Leu Ile     His Pro Arg Gln     Leu Leu Leu Ser Arg Ile Leu
            1285                1290                1295 ctg ata gac gtc att gcc gtc gtt gca tgg taa ctt tga atc ttt ctt    3936
Leu Ile Asp Val Ile Ala Val Val Ala Trp     Leu     Ile Phe Leu
            1300                1305                1310 ttt taa ttt agc cac aaa aaa ggg aga tga tca tac atg ttt tta ttt    3984
Phe     Phe Ser His Lys Lys Gly Arg     Ser Tyr Met Phe Leu Phe
        1315                1320                1325 tat ttt atc att tgt ttt aca gat att cga ttg tca tat gca tga gaa    4032
Tyr Phe Ile Ile Cys Phe Thr Asp Ile Arg Leu Ser Tyr Ala     Glu
        1330                1335                1340 gta tga gcc cga gtc tag atc cgt aag cat taa att cat tta aat tat    4080
Val     Ala Arg Val     Ile Arg Lys His     Ile His Leu Asn Tyr
1345                1350                1355                1360
```

| | |
|---|---|
| ttt gtt agt ttc aca acc ctt ata tat aag gtt aag tga tta act taa<br>Phe Val Ser Phe Thr Thr Leu Ile Tyr Lys Val Lys      Leu Thr<br>                      1365                 1370               1375 | 4128 |
| tta gat tgc ttt ggc ttg tca gag cga aga caa atc tag ttt gtt tga<br>Leu Asp Cys Phe Gly Leu Ser Glu Arg Arg Gln Ile      Phe Val<br>          1380                 1385                 1390 | 4176 |
| gga tga aga tag aca acc atg cag tga gca ttg tta cct caa ggt ctc<br>Gly     Arg     Thr Thr Met Gln     Ala Leu Leu Pro Gln Gly Leu<br>     1395                   1400                 1405 | 4224 |
| tat ctc tct ccc tct ctc tct caa ttt ttt tgt cta ttc ctt aat tac<br>Tyr Leu Ser Pro Ser Leu Ser Gln Phe Phe Cys Leu Phe Leu Asn Tyr<br>    1410                  1415                 1420 | 4272 |
| gtt tat tag tta ctg gtt taa tat taa ata ggt gag gag tgt gac aga<br>Val Tyr     Leu Leu Val     Tyr        Ile Gly Glu Glu Cys Asp Arg<br>1425              1430                     1435                1440 | 4320 |
| agc tga tca tgt gat gga taa tga taa ctc tat atc aaa caa gat tgt<br>Ser      Ser Cys Asp Gly             Leu Tyr Ile Lys Gln Asp Cys<br>                  1445                     1450              1455 | 4368 |
| ggt ctc aga tcc aaa caa cac tat gtg gac gcc tgt aga gaa gga tct<br>Gly Leu Arg Ser Lys Gln His Tyr Val Asp Ala Cys Arg Glu Gly Ser<br>              1460                  1465                1470 | 4416 |
| tta ctt gaa agg aat tga gat att tgg gag aaa cag gta aaa aaa taa<br>Leu Leu Glu Arg Asn     Asp Ile Trp Glu Lys Gln Val Lys Lys<br>         1475                     1480                 1485 | 4464 |
| aaa tag att taa tgc att aat ata tat act tac act gta ttc ctt gat<br>Lys     Ile      Cys Ile Asn Ile Tyr Thr Tyr Thr Val Phe Leu Asp<br>    1490                   1495                 1500 | 4512 |
| tat gct ggt tcg cag ttg tga tgt tgc att aaa cat act tcg ggg gct<br>Tyr Ala Gly Ser Gln Leu      Cys Cys Ile Lys His Thr Ser Gly Ala<br>1505               1510                  1515                1520 | 4560 |
| taa gac gtg cct aga gat tta caa tta cat gcg cga aca aga tca atg<br>      Asp Val Pro Arg Asp Leu Gln Leu His Ala Arg Thr Arg Ser Met<br>             1525                 1530                 1535 | 4608 |
| tac tat gtc att aga cct taa caa aac tac aca aag aca caa tca ggt<br>Tyr Tyr Val Ile Arg Pro      Gln Asn Tyr Thr Lys Thr Gln Ser Gly<br>            1540                  1545                1550 | 4656 |
| aca cta acc tat gtc gta att att ctc atg aca tgt atg tta aaa aca<br>Thr Leu Thr Tyr Val Val Ile Ile Leu Met Thr Cys Met Leu Lys Thr<br>          1555                  1560                1565 | 4704 |
| cat gaa gtt tcc tat atg tgt tga tgg ttt tat cac agg tta cca aaa<br>His Glu Val Ser Tyr Met Cys      Trp Phe Tyr His Arg Leu Pro Lys<br>    1570                 1575                 1580 | 4752 |
| aag tat ctc gaa aaa gta gta ggt cgg tcc gca aaa aat cga gac tcc<br>Lys Tyr Leu Glu Lys Val Val Gly Arg Ser Ala Lys Asn Arg Asp Ser<br>1585              1590                  1595                1600 | 4800 |
| gaa aat atg ctc gtt atc cgc ctg ctt taa aga aaa caa cta gtg gag<br>Glu Asn Met Leu Val Ile Arg Leu Leu      Arg Lys Gln Leu Val Glu<br>            1605                  1610                 1615 | 4848 |
| aag cta agt ttt ata agc act aca cac cat gca ctt gca agt caa aat<br>Lys Leu Ser Phe Ile Ser Thr Thr His His Ala Leu Ala Ser Gln Asn<br>          1620                  1625                1630 | 4896 |
| gtg gac agc aat gcc ctt gtt taa ctc acg aaa att gct gcg aga aat<br>Val Asp Ser Asn Ala Leu Val      Leu Thr Lys Ile Ala Ala Arg Asn<br>        1635                  1640                 1645 | 4944 |
| att gcg ggt atg tca ttc aat ttt tcc taa gcc gga aga tcc atg aga<br>Ile Ala Gly Met Ser Phe Asn Phe Ser      Ala Gly Arg Ser Met Arg<br>1650              1655                  1660 | 4992 |
| ttt aat ttg aac atg agt ttg tat ttt ttg ttc agg tgc tca aag gat<br>Phe Asn Leu Asn Met Ser Leu Tyr Phe Leu Phe Arg Cys Ser Lys Asp<br>1665              1670                  1675                1680 | 5040 |

| | |
|---|---|
| tgc aac aat cgc ttt gga gga tgt aat tgt gca att ggc caa tgc aca<br>Cys Asn Asn Arg Phe Gly Gly Cys Asn Cys Ala Ile Gly Gln Cys Thr<br>                                      1685                               1690                      1695 | 5088 |
| aat cga caa tgt cct tgt ttt gct gct aat cgt gaa tgc gat cca gat<br>Asn Arg Gln Cys Pro Cys Phe Ala Ala Asn Arg Glu Cys Asp Pro Asp<br>            1700                       1705                       1710 | 5136 |
| ctt tgt cgg agt tgt cct ctt agg taa cac ttt cac ttc aat atc tct<br>Leu Cys Arg Ser Cys Pro Leu Arg     His Phe His Phe Asn Ile Ser<br>      1715                         1720                       1725 | 5184 |
| tta tac aaa ttc tat aat caa agt aat tca aac caa aag tct tat aaa<br>Leu Tyr Lys Phe Tyr Asn Gln Ser Asn Ser Asn Gln Lys Ser Tyr Lys<br>            1730                       1735                       1740 | 5232 |
| aaa aac ttt ata tat agc tgt gga gat ggc act ctt ggt gag aca cca<br>Lys Asn Phe Ile Tyr Ser Cys Gly Asp Gly Thr Leu Gly Glu Thr Pro<br>1745                       1750                       1755                       1760 | 5280 |
| gtg caa atc caa tgc aag aac atg caa ttc ctc ctt caa acc aat aaa<br>Val Gln Ile Gln Cys Lys Asn Met Gln Phe Leu Leu Gln Thr Asn Lys<br>            1765                       1770                       1775 | 5328 |
| aag gta atc aac gtc aaa tcc gta ccg aaa att taa aac taa tta tac<br>Lys Val Ile Asn Val Lys Ser Val Pro Lys Ile     Asn     Leu Tyr<br>            1780                       1785                       1790 | 5376 |
| gaa aga cat tta act atc att tcc cgt att tta cta gat tct cat tgg<br>Glu Arg His Leu Thr Ile Ile Ser Arg Ile Leu Leu Asp Ser His Trp<br>            1795                       1800                       1805 | 5424 |
| aaa gtc tga tgt tca tgg atg ggg tgc att tac atg ggt aag caa tca<br>Lys Val     Cys Ser Trp Met Gly Cys Ile Tyr Met Gly Lys Gln Ser<br>      1810                         1815                       1820 | 5472 |
| tgt aaa tat aag aat aag ttt aat agt tat tgg tgc att cat aac act<br>Cys Lys Tyr Lys Asn Lys Phe Asn Ser Tyr Trp Cys Ile His Asn Thr<br>1825                       1830                       1835                       1840 | 5520 |
| ttt ttt ttt tta ata atg ttt tat act tta gac cat taa ata tat tgt<br>Phe Phe Phe Leu Ile Met Phe Tyr Thr Leu Asp His     Ile Tyr Cys<br>            1845                       1850                       1855 | 5568 |
| gtg ata tgg ttt gac ccg tca gga ctc tct taa aaa gaa tga gta tct<br>Val Ile Trp Phe Asp Pro Ser Gly Leu Ser     Lys Glu     Val Ser<br>            1860                       1865                       1870 | 5616 |
| cgg aga ata tac tgg aga act gat cac tca tga tga agc taa tga gcg<br>Arg Arg Ile Tyr Trp Arg Thr Asp His Ser         Ser     Ala<br>            1875                       1880                       1885 | 5664 |
| tgg gag aat aga aga tcg gat tgg ttc ttc cta cct ctt tac ctt gaa<br>Trp Glu Asn Arg Arg Ser Asp Trp Phe Phe Leu Pro Leu Tyr Leu Glu<br>            1890                       1895                       1900 | 5712 |
| tga tca ggt aac ttc aga ata att ttg aag taa cgt ttt aat cat tcg<br>    Ser Gly Asn Phe Arg Ile Ile Leu Lys     Arg Phe Asn His Ser<br>1905                       1910                       1915                       1920 | 5760 |
| cgg gtt aca cat cta ttc gaa tca aag taa cat tta ttt tac agc tcg<br>Arg Val Thr His Leu Phe Glu Ser Lys     His Leu Phe Tyr Ser Ser<br>            1925                       1930                       1935 | 5808 |
| aaa tcg atg ctc gcc gta aag gaa acg agt tca aat ttc tca atc act<br>Lys Ser Met Leu Ala Val Lys Glu Thr Ser Ser Asn Phe Ser Ile Thr<br>            1940                       1945                       1950 | 5856 |
| cag caa gac cta act gct acg cca agg tac taa gcc gtt ata ctt tat<br>Gln Gln Asp Leu Thr Ala Thr Pro Arg Tyr     Ala Val Ile Leu Tyr<br>            1955                       1960                       1965 | 5904 |
| ctt gaa caa ata cta aca tta tac aaa caa aaa tac tta tgt tag ttt<br>Leu Glu Gln Ile Leu Thr Leu Tyr Lys Gln Lys Tyr Leu Cys     Phe<br>            1970                       1975                       1980 | 5952 |
| ctt tag tta aat cgt gta tca act tta ctc gtc gtt gat tgg ttt tca<br>Leu     Leu Asn Arg Val Ser Thr Leu Leu Val Val Asp Trp Phe Ser | 6000 |

```
1985                1990                1995                2000
tat tga aga tat tcc aag aaa ctc aaa ctc att tta aat gat ttt ttc    6048
Tyr     Arg Tyr Ser Lys Lys Leu Lys Leu Ile Leu Asn Asp Phe Phe
            2005                2010                2015 ttg tcg aga aaa ttt agg tta cga aaa ttt atg gtt tcg tgt gca gtt    6096
Leu Ser Arg Lys Phe Arg Leu Arg Lys Phe Met Val Ser Cys Ala Val
        2020                2025                2030 gat gat tgt gag agg aga tca gag gat tgg tct att tgc gga gag agc    6144
Asp Asp Cys Glu Arg Arg Ser Glu Asp Trp Ser Ile Cys Gly Glu Ser
        2035                2040                2045 aat cga aga agg tga gga gct ttt ctt cga cta ctg cta tgg acc aga    6192
Asn Arg Arg Arg     Gly Ala Phe Leu Arg Leu Leu Leu Trp Thr Arg
        2050                2055                2060 aca tgc gga ttg gtc gcg tgg tcg aga acc tag aaa gac tgg tgc ttc    6240
Thr Cys Gly Leu Val Ala Trp Ser Arg Thr     Lys Asp Trp Cys Phe
2065                2070                2075                2080 taa aag gtc taa gga agc ccg tcc agc tcg tta gtt ttt gat ctg agg    6288
    Lys Val     Gly Ser Pro Ser Ser Ser Leu Val Phe Asp Leu Arg
                2085                2090                2095 aga agc agc aat tca agc agt cct ttt ttt atg tta tgg tat atc aat    6336
Arg Ser Ser Asn Ser Ser Ser Pro Phe Phe Met Leu Trp Tyr Ile Asn
        2100                2105                2110 taa taa tgt aat gct att ttg tgt tac taa acc aaa act taa gtt tct    6384
        Cys Asn Ala Ile Leu Cys Tyr     Thr Lys Thr     Val Ser
            2115                2120                2125 gtt tta ttt gtt tta ggg tgt ttt gtt tgt atc ata tgt gtc tta act    6432
Val Leu Phe Val Leu Gly Cys Phe Val Cys Ile Ile Cys Val Leu Thr
        2130                2135                2140 ttc aaa gtt ttc ttt ttg tat ttc aat tta aaa aca atg ttt atg ttg    6480
Phe Lys Val Phe Phe Leu Tyr Phe Asn Leu Lys Thr Met Phe Met Leu
2145                2150                2155                2160 tta gtt tgc ata gac ctt tgg aaa aaa aaa gct ttg cac aac ttt aca    6528
Leu Val Cys Ile Asp Leu Trp Lys Lys Lys Ala Leu His Asn Phe Thr
                2165                2170                2175 ttt att tag tct tca ttt agc gaa aaa tca cat aac aca agt ctg tgg    6576
Phe Ile     Ser Ser Phe Ser Glu Lys Ser His Asn Thr Ser Leu Trp
        2180                2185                2190 tac gta atg tac aaa aat gtc aaa ata atg ggt ttt atc att aaa aaa    6624
Tyr Val Met Tyr Lys Asn Val Lys Ile Met Gly Phe Ile Ile Lys Lys
        2195                2200                2205 aaa tat tgg tta tga atg aag tat agt tag aat ttt agg tat tag ctc    6672
Lys Tyr Trp Leu     Met Lys Tyr Ser     Asn Phe Arg Tyr     Leu
    2210                2215                2220 gtt tgg ttt taa aac gtt ttt cga gat tta att ttg tag tct att gag    6720
Val Trp Phe     Asn Val Phe Arg Asp Leu Ile Leu     Ser Ile Glu
2225                2230                2235                2240 taa tac atg gaa gaa tca tca aca aag tgg ctg tag ctt acg aaa ggt    6768
    Tyr Met Glu Glu Ser Ser Thr Lys Trp Leu     Leu Thr Lys Gly
            2245                2250                2255 ttt act tta atg taa ata tgt att tga tgc atc taa cat tta gta tct    6816
Phe Thr Leu Met     Ile Cys Ile     Cys Ile     His Leu Val Ser
        2260                2265                2270 aaa caa ata aaa aca aaa aaa aag aaa aaa gct ctt taa aat ccg aaa    6864
Lys Gln Ile Lys Thr Lys Lys Lys Lys Lys Ala Leu     Asn Pro Lys
        2275                2280                2285 gta act att ttc aaa aaa tct aaa tta taa act taa atg ttt gga atc    6912
Val Thr Ile Phe Lys Lys Ser Lys Leu     Thr     Met Phe Gly Ile
    2290                2295                2300 gcg aac gac tat tgc taa ata taa atg cta aat ata cat gaa gat gtg    6960
```

```
Ala Asn Asp Tyr Cys     Ile     Met Leu Asn Ile His Glu Asp Val
2305                2310                2315                2320 aaa aac atg ttg gat ttg tgg aat cgt taa tga cca cgg tta aat ggc    7008
Lys Asn Met Leu Asp Leu Trp Asn Arg             Pro Arg Leu Asn Gly
                2325                2330                2335 ggg atc c                                                          7015
Gly Ile

<210> SEQ ID NO: 7
<211> LENGTH: 34
<212> TYPE: PRT
<213> ORGANISM: Arabidopsis sp.

<400> SEQUENCE: 7

Gly Ser Ile Ile Phe Lys Asn Gln Ile Phe Ser Tyr Leu Leu Phe Val
 1               5                  10                  15

Ser Lys Lys Lys Thr His Asp Asp Tyr Pro Ser Ala Gly Cys Val
            20                  25                  30

His Arg

<210> SEQ ID NO: 8
<211> LENGTH: 12
<212> TYPE: PRT
<213> ORGANISM: Arabidopsis sp.

<400> SEQUENCE: 8

Thr Tyr Ile Leu Lys Leu Val Gly Phe Ser Leu Pro
 1               5                  10

<210> SEQ ID NO: 9
<211> LENGTH: 18
<212> TYPE: PRT
<213> ORGANISM: Arabidopsis sp.

<400> SEQUENCE: 9

Val Trp Thr Cys Phe Tyr Asn Leu Met Tyr Ser Val Asp Gln Lys Ile
 1               5                  10                  15

Glu Lys

<210> SEQ ID NO: 10
<211> LENGTH: 6
<212> TYPE: PRT
<213> ORGANISM: Arabidopsis sp.

<400> SEQUENCE: 10

Glu Arg Glu Pro Leu Trp
 1               5

<210> SEQ ID NO: 11
<211> LENGTH: 20
<212> TYPE: PRT
<213> ORGANISM: Arabidopsis sp.

<400> SEQUENCE: 11

Gln Asn Arg Asn His Tyr Ile Glu Ser Phe Glu Lys Thr Lys Arg Ser
 1               5                  10                  15

Asn Leu Cys Ser
            20

<210> SEQ ID NO: 12
<211> LENGTH: 15
<212> TYPE: PRT
```

<213> ORGANISM: Arabidopsis sp.

<400> SEQUENCE: 12

Met Thr Ile Asp Val Ala Ala Asn Tyr Ser Leu Asn Ala Phe Ile
 1               5                  10                  15

<210> SEQ ID NO: 13
<211> LENGTH: 307
<212> TYPE: PRT
<213> ORGANISM: Arabidopsis sp.

<400> SEQUENCE: 13

Ile Phe Leu Thr Ser Ser Val Pro Ser His Ser Arg Asn Ser Ile Ile
 1               5                  10                  15

Pro Phe Ser Phe Phe Ser Val Phe Gln Ser Leu Arg Ile Lys Met
                20                  25                  30

Glu His Glu Glu Thr Gln Lys Asn Thr Arg Asn Ser Trp Ser Leu Ile
                35                  40                  45

Arg Pro Phe Gln Met Ile Ser Ile Ser Phe Leu Ser Leu Leu Leu Pro
        50                  55                  60

Leu Ser Phe Leu Phe Leu Ser Arg Leu Ser Leu Tyr Thr Ser Ser Thr
65                  70                  75                  80

Pro Val Thr Val Ser Gly Val Ser Val Ile His Gln Ala Asp Val
                85                  90                  95

Gly Val Leu Tyr Thr Ile Leu Phe Leu Ile Ile Val Phe Thr Leu Ile
                100                 105                 110

His Ser Leu Ser Gly Lys Pro Glu Cys Ser Val Leu His Ser His Leu
            115                 120                 125

Tyr Ile Cys Trp Ile Val Leu Phe Ile Ala Gln Ala Cys Ala Phe Gly
        130                 135                 140

Ile Lys Arg Thr Met Ser Thr Thr Met Ser Ile Asn Pro Asp Lys Asn
145                 150                 155                 160

Leu Phe Leu Ala Thr His Glu Arg Trp Met Leu Val Arg Val Leu Phe
                165                 170                 175

Phe Leu Gly Leu His Glu Val Met Leu Met Trp Phe Arg Val Val Val
            180                 185                 190

Lys Pro Val Val Asp Asn Thr Ile Tyr Gly Val Tyr Val Glu Glu Arg
        195                 200                 205

Trp Ser Glu Arg Ala Val Ala Val Thr Phe Gly Ile Met Trp Trp
210                 215                 220

Trp Arg Leu Arg Asp Glu Val Glu Ser Leu Val Val Val Thr Ala
225                 230                 235                 240

Asp Arg Leu Asn Leu Pro Ile Arg Leu Glu Gly Leu Asn Phe Val Asn
                245                 250                 255

Trp Cys Met Tyr Tyr Ile Cys Val Gly Ile Gly Leu Met Lys Ile Phe
            260                 265                 270

Lys Gly Phe Leu Asp Phe Val Asn Thr Leu Thr Leu Ser Ile Lys Arg
        275                 280                 285

Ser Arg Lys Gly Cys Glu Ser Cys Val Phe Asp Asp Met Cys Asn Asp
    290                 295                 300

Asp His Val
305

<210> SEQ ID NO: 14
<211> LENGTH: 6
<212> TYPE: PRT

```
<213> ORGANISM: Arabidopsis sp.

<400> SEQUENCE: 14

His Ile Ile Leu Ile Ser
 1               5

<210> SEQ ID NO: 15
<211> LENGTH: 42
<212> TYPE: PRT
<213> ORGANISM: Arabidopsis sp.

<400> SEQUENCE: 15

Met Phe Leu Arg Phe Phe Tyr Phe Tyr Phe Leu Phe Leu Ala Arg Asn
 1               5                  10                  15

Leu Thr Arg Ile Tyr Val Thr Lys Ile Val Glu Tyr Gln Lys Ala Lys
            20                  25                  30

Ile Phe Tyr Leu Lys Ile Thr Ile Glu His
        35                  40

<210> SEQ ID NO: 16
<211> LENGTH: 14
<212> TYPE: PRT
<213> ORGANISM: Arabidopsis sp.

<400> SEQUENCE: 16

Phe Lys Ser Phe Tyr Asn Tyr Ile Phe Ile Thr His Pro Phe
 1               5                  10

<210> SEQ ID NO: 17
<211> LENGTH: 26
<212> TYPE: PRT
<213> ORGANISM: Arabidopsis sp.

<400> SEQUENCE: 17

Glu Lys Leu Gly Asp Leu Ile Asn Val Ile Asn Ser Lys Lys Tyr Arg
 1               5                  10                  15

Ile Tyr Val Glu Val Leu Asn Ala Tyr Asn
            20                  25

<210> SEQ ID NO: 18
<211> LENGTH: 15
<212> TYPE: PRT
<213> ORGANISM: Arabidopsis sp.

<400> SEQUENCE: 18

Ile Tyr Glu Leu Asn Asn Ile Ala Ile Tyr Ile Phe Leu Lys Ile
 1               5                  10                  15

<210> SEQ ID NO: 19
<211> LENGTH: 9
<212> TYPE: PRT
<213> ORGANISM: Arabidopsis sp.

<400> SEQUENCE: 19

Thr His Phe Val Ser Ser Ile Tyr Ala
 1               5

<210> SEQ ID NO: 20
<211> LENGTH: 13
<212> TYPE: PRT
<213> ORGANISM: Arabidopsis sp.

<400> SEQUENCE: 20
```

Tyr Ile Ser Leu Asn Arg Lys Leu Ala Arg Asn Glu Tyr
 1               5                  10

<210> SEQ ID NO: 21
<211> LENGTH: 31
<212> TYPE: PRT
<213> ORGANISM: Arabidopsis sp.

<400> SEQUENCE: 21

Tyr Lys Ser Tyr Arg Thr Leu Gln Asn Val Tyr Ile Asp Leu Ser Thr
 1               5                  10                  15

Phe Phe His Trp Phe Thr Lys Pro Ser Cys His Ile Asn Met Ser
             20                  25                  30

<210> SEQ ID NO: 22
<211> LENGTH: 31
<212> TYPE: PRT
<213> ORGANISM: Arabidopsis sp.

<400> SEQUENCE: 22

Arg Leu Phe Phe Tyr Asn Ile Val Tyr Glu Phe Lys Leu Glu Leu Ser
 1               5                  10                  15

Asn Val Lys Gln Thr Gln His Leu His Thr Tyr Ser Thr Ile Phe
             20                  25                  30

<210> SEQ ID NO: 23
<211> LENGTH: 5
<212> TYPE: PRT
<213> ORGANISM: Arabidopsis sp.

<400> SEQUENCE: 23

Lys Leu Lys Phe Ser
 1               5

<210> SEQ ID NO: 24
<211> LENGTH: 23
<212> TYPE: PRT
<213> ORGANISM: Arabidopsis sp.

<400> SEQUENCE: 24

Ile Ser His Ile Ile Phe Leu Leu Lys Gln Ala Ser Pro Asn Thr Phe
 1               5                  10                  15

Leu Pro Asp Tyr Asn Phe Pro
             20

<210> SEQ ID NO: 25
<211> LENGTH: 34
<212> TYPE: PRT
<213> ORGANISM: Arabidopsis sp.

<400> SEQUENCE: 25

Gly Phe Leu Gln Lys Lys Ile Asn Phe Leu Phe Lys Lys Pro Phe Ala
 1               5                  10                  15

Leu Ser Phe Ser Pro Thr Ser Glu Lys Thr Arg Lys Lys Glu Glu Ala
             20                  25                  30

Ser Gly

<210> SEQ ID NO: 26
<211> LENGTH: 12
<212> TYPE: PRT
<213> ORGANISM: Arabidopsis sp.

<400> SEQUENCE: 26

```
Trp Arg Arg Leu Val Ser Leu Gln Thr Tyr Met Asn
  1               5                  10
```

<210> SEQ ID NO: 27
<211> LENGTH: 8
<212> TYPE: PRT
<213> ORGANISM: Arabidopsis sp.

<400> SEQUENCE: 27

```
Leu Gly Tyr Glu Ile His Ile Phe
  1               5
```

<210> SEQ ID NO: 28
<211> LENGTH: 25
<212> TYPE: PRT
<213> ORGANISM: Arabidopsis sp.

<400> SEQUENCE: 28

```
Leu Cys Val Tyr Asp Arg Ser Ile Thr Phe Arg Val Glu Phe Ser Cys
  1               5                  10                  15

Asp Leu Leu Cys Tyr Ser Ser His Ala
             20                  25
```

<210> SEQ ID NO: 29
<211> LENGTH: 24
<212> TYPE: PRT
<213> ORGANISM: Arabidopsis sp.

<400> SEQUENCE: 29

```
Ser Ile Lys Leu Leu Phe Leu Asn Leu Ser Arg Lys Thr Met Arg Thr
  1               5                  10                  15

Met Val Arg Val Cys His Pro Asn
             20
```

<210> SEQ ID NO: 30
<211> LENGTH: 13
<212> TYPE: PRT
<213> ORGANISM: Arabidopsis sp.

<400> SEQUENCE: 30

```
Lys Ser Lys Ser Lys Arg Arg Asp Phe Cys Ile Ser Arg
  1               5                  10
```

<210> SEQ ID NO: 31
<211> LENGTH: 18
<212> TYPE: PRT
<213> ORGANISM: Arabidopsis sp.

<400> SEQUENCE: 31

```
Glu Thr Phe Gly Cys Phe Asn Ile Leu Phe Ser Ser Val Cys Phe Ser
  1               5                  10                  15

Glu Asn
```

<210> SEQ ID NO: 32
<211> LENGTH: 5
<212> TYPE: PRT
<213> ORGANISM: Arabidopsis sp.

<400> SEQUENCE: 32

```
Gly Glu Glu Arg Thr
  1               5
```

```
<210> SEQ ID NO: 33
<211> LENGTH: 10
<212> TYPE: PRT
<213> ORGANISM: Arabidopsis sp.

<400> SEQUENCE: 33

Ser His Asn Tyr Thr Ile Pro Lys Arg Cys
 1               5                  10

<210> SEQ ID NO: 34
<211> LENGTH: 13
<212> TYPE: PRT
<213> ORGANISM: Arabidopsis sp.

<400> SEQUENCE: 34

Asp Thr Ser Asn Lys Gln Leu Tyr Ile Ser His Asn Leu
 1               5                  10

<210> SEQ ID NO: 35
<211> LENGTH: 7
<212> TYPE: PRT
<213> ORGANISM: Arabidopsis sp.

<400> SEQUENCE: 35

Lys Glu Lys Phe Pro Asn Phe
 1               5

<210> SEQ ID NO: 36
<211> LENGTH: 5
<212> TYPE: PRT
<213> ORGANISM: Arabidopsis sp.

<400> SEQUENCE: 36

Ile Lys Asn Arg Ile
 1               5

<210> SEQ ID NO: 37
<211> LENGTH: 6
<212> TYPE: PRT
<213> ORGANISM: Arabidopsis sp.

<400> SEQUENCE: 37

Lys Met Pro Ala Asn Arg
 1               5

<210> SEQ ID NO: 38
<211> LENGTH: 12
<212> TYPE: PRT
<213> ORGANISM: Arabidopsis sp.

<400> SEQUENCE: 38

Arg His Pro Asp Leu Ser Gly Ile Gln Asn Leu Glu
 1               5                  10

<210> SEQ ID NO: 39
<211> LENGTH: 11
<212> TYPE: PRT
<213> ORGANISM: Arabidopsis sp.

<400> SEQUENCE: 39

Tyr Ile Tyr Asn Ile Lys Leu Glu Leu Arg Leu
 1               5                  10

<210> SEQ ID NO: 40
<211> LENGTH: 16
```

```
<212> TYPE: PRT
<213> ORGANISM: Arabidopsis sp.

<400> SEQUENCE: 40

Asn Lys Ile Glu Asn Asn Ser Arg Phe Phe Cys Phe Cys Gln Thr Lys
 1               5                  10                  15

<210> SEQ ID NO: 41
<211> LENGTH: 10
<212> TYPE: PRT
<213> ORGANISM: Arabidopsis sp.

<400> SEQUENCE: 41

Tyr Asn Leu Phe Phe Leu Val Gln Arg Asn
 1               5                  10

<210> SEQ ID NO: 42
<211> LENGTH: 33
<212> TYPE: PRT
<213> ORGANISM: Arabidopsis sp.

<400> SEQUENCE: 42

Ile Gly Pro Asn Cys Phe Phe Phe Asn Ile Gln Pro Lys Lys Pro Arg
 1               5                  10                  15

Leu Met His Ile Ser Arg Asn Arg Asn Gln Asn Phe Cys Ile Gln Val
            20                  25                  30

Phe

<210> SEQ ID NO: 43
<211> LENGTH: 4
<212> TYPE: PRT
<213> ORGANISM: Arabidopsis sp.

<400> SEQUENCE: 43

Phe His Tyr Ile
 1

<210> SEQ ID NO: 44
<211> LENGTH: 6
<212> TYPE: PRT
<213> ORGANISM: Arabidopsis sp.

<400> SEQUENCE: 44

Ser Pro Val Ser Glu Ile
 1               5

<210> SEQ ID NO: 45
<211> LENGTH: 8
<212> TYPE: PRT
<213> ORGANISM: Arabidopsis sp.

<400> SEQUENCE: 45

Lys Ile Ile Tyr Leu Tyr Ile Thr
 1               5

<210> SEQ ID NO: 46
<211> LENGTH: 23
<212> TYPE: PRT
<213> ORGANISM: Arabidopsis sp.

<400> SEQUENCE: 46

Leu Thr Glu Lys Ile Arg Ala Glu Ile His Ser Lys Cys Gly Tyr Ser
 1               5                  10                  15
```

```
Cys Phe Thr Pro Ser Ile Val
            20

<210> SEQ ID NO: 47
<211> LENGTH: 8
<212> TYPE: PRT
<213> ORGANISM: Arabidopsis sp.

<400> SEQUENCE: 47

Leu Lys Pro Ala Arg Cys Arg Gly
 1               5

<210> SEQ ID NO: 48
<211> LENGTH: 22
<212> TYPE: PRT
<213> ORGANISM: Arabidopsis sp.

<400> SEQUENCE: 48

Trp Arg Arg Gln Gln Ile Thr Phe Val Glu Asn Ala Lys Pro Thr Ser
 1               5                  10                  15

Ser Phe Gln Cys Leu Ile
            20

<210> SEQ ID NO: 49
<211> LENGTH: 9
<212> TYPE: PRT
<213> ORGANISM: Arabidopsis sp.

<400> SEQUENCE: 49

Phe Leu Arg Arg Ser Arg Leu Cys Ser
 1               5

<210> SEQ ID NO: 50
<211> LENGTH: 6
<212> TYPE: PRT
<213> ORGANISM: Arabidopsis sp.

<400> SEQUENCE: 50

Gly Ser Arg Leu Cys Ser
 1               5

<210> SEQ ID NO: 51
<211> LENGTH: 7
<212> TYPE: PRT
<213> ORGANISM: Arabidopsis sp.

<400> SEQUENCE: 51

Arg Arg Cys Thr Ile Ile Ser
 1               5

<210> SEQ ID NO: 52
<211> LENGTH: 13
<212> TYPE: PRT
<213> ORGANISM: Arabidopsis sp.

<400> SEQUENCE: 52

Arg Cys Thr Ile Ile Thr Lys Cys Gln Ala Ser Asn Cys
 1               5                  10

<210> SEQ ID NO: 53
<211> LENGTH: 21
<212> TYPE: PRT
<213> ORGANISM: Arabidopsis sp.

<400> SEQUENCE: 53
```

```
Glu Ala Thr Thr Ile His Tyr Met Gly Leu His Gln Lys Ala Cys Val
 1               5                  10                  15

Phe Phe Val Ser Tyr
            20
```

<210> SEQ ID NO: 54
<211> LENGTH: 13
<212> TYPE: PRT
<213> ORGANISM: Arabidopsis sp.

<400> SEQUENCE: 54

```
Phe Gln Asn Ile Asn His Ile Leu Tyr Ser Asn His Ser
 1               5                  10
```

<210> SEQ ID NO: 55
<211> LENGTH: 6
<212> TYPE: PRT
<213> ORGANISM: Arabidopsis sp.

<400> SEQUENCE: 55

```
Cys Ile Tyr Thr Phe Leu
 1               5
```

<210> SEQ ID NO: 56
<211> LENGTH: 74
<212> TYPE: PRT
<213> ORGANISM: Arabidopsis sp.

<400> SEQUENCE: 56

```
His Cys Ser Ser Gln Leu Met Ala Glu Ser Asp Ser Val Ile Gly Lys
 1               5                  10                  15

Arg Gln Ile Tyr Tyr Leu Asn Gly Glu Ala Leu Glu Leu Ser Ser Glu
                20                  25                  30

Glu Asp Glu Glu Asp Glu Glu Glu Asp Glu Glu Ile Lys Lys Glu
            35                  40                  45

Lys Cys Glu Phe Ser Glu Asp Val Asp Arg Phe Ile Trp Leu Val Phe
     50                  55                  60

Ala Leu His Met Phe Leu Ile Ile Asn Leu
 65                  70
```

<210> SEQ ID NO: 57
<211> LENGTH: 41
<212> TYPE: PRT
<213> ORGANISM: Arabidopsis sp.

<400> SEQUENCE: 57

```
Ser Ile Phe Asn Lys Leu Leu Lys Lys Phe Ser Gly Arg Leu Gly Arg
 1               5                  10                  15

Thr Met Val Trp Met Ile Trp Ser Cys Gly Val Leu Ser Pro Ser Thr
                20                  25                  30

Ser Lys Trp Met Phe Arg Thr Tyr Trp
            35                  40
```

<210> SEQ ID NO: 58
<211> LENGTH: 17
<212> TYPE: PRT
<213> ORGANISM: Arabidopsis sp.

<400> SEQUENCE: 58

```
Gln Tyr Ser Asn Lys Asn Phe Ile Arg Arg Ser Ile Thr Phe Leu Leu
 1               5                  10                  15
```

Ile

<210> SEQ ID NO: 59
<211> LENGTH: 15
<212> TYPE: PRT
<213> ORGANISM: Arabidopsis sp.

<400> SEQUENCE: 59

Phe Leu Leu Phe Phe Val Val Arg Asn Val Leu Asn Phe Gln Ile
 1               5                  10                  15

<210> SEQ ID NO: 60
<211> LENGTH: 21
<212> TYPE: PRT
<213> ORGANISM: Arabidopsis sp.

<400> SEQUENCE: 60

Cys Arg Lys Asp Thr Met Asn Ser Ser Leu Arg Met Met Glu Leu Leu
 1               5                  10                  15

Val Arg Leu Leu Ile
            20

<210> SEQ ID NO: 61
<211> LENGTH: 4
<212> TYPE: PRT
<213> ORGANISM: Arabidopsis sp.

<400> SEQUENCE: 61

His Pro Arg Gln
 1

<210> SEQ ID NO: 62
<211> LENGTH: 17
<212> TYPE: PRT
<213> ORGANISM: Arabidopsis sp.

<400> SEQUENCE: 62

Leu Leu Leu Ser Arg Ile Leu Leu Ile Asp Val Ile Ala Val Val Ala
 1               5                  10                  15

Trp

<210> SEQ ID NO: 63
<211> LENGTH: 4
<212> TYPE: PRT
<213> ORGANISM: Arabidopsis sp.

<400> SEQUENCE: 63

Ile Phe Leu Phe
 1

<210> SEQ ID NO: 64
<211> LENGTH: 7
<212> TYPE: PRT
<213> ORGANISM: Arabidopsis sp.

<400> SEQUENCE: 64

Phe Ser His Lys Lys Gly Arg
 1               5

<210> SEQ ID NO: 65
<211> LENGTH: 20
<212> TYPE: PRT
<213> ORGANISM: Arabidopsis sp.

```
<400> SEQUENCE: 65

Ser Tyr Met Phe Leu Phe Tyr Phe Ile Ile Cys Phe Thr Asp Ile Arg
 1               5                  10                  15

Leu Ser Tyr Ala
            20

<210> SEQ ID NO: 66
<211> LENGTH: 4
<212> TYPE: PRT
<213> ORGANISM: Arabidopsis sp.

<400> SEQUENCE: 66

Ile Arg Lys His
 1

<210> SEQ ID NO: 67
<211> LENGTH: 17
<212> TYPE: PRT
<213> ORGANISM: Arabidopsis sp.

<400> SEQUENCE: 67

Ile His Leu Asn Tyr Phe Val Ser Phe Thr Thr Leu Ile Tyr Lys Val
 1               5                  10                  15

Lys

<210> SEQ ID NO: 68
<211> LENGTH: 12
<212> TYPE: PRT
<213> ORGANISM: Arabidopsis sp.

<400> SEQUENCE: 68

Leu Asp Cys Phe Gly Leu Ser Glu Arg Arg Gln Ile
 1               5                  10

<210> SEQ ID NO: 69
<211> LENGTH: 4
<212> TYPE: PRT
<213> ORGANISM: Arabidopsis sp.

<400> SEQUENCE: 69

Thr Thr Met Gln
 1

<210> SEQ ID NO: 70
<211> LENGTH: 25
<212> TYPE: PRT
<213> ORGANISM: Arabidopsis sp.

<400> SEQUENCE: 70

Ala Leu Leu Pro Gln Gly Leu Tyr Leu Ser Pro Ser Leu Ser Gln Phe
 1               5                  10                  15

Phe Cys Leu Phe Leu Asn Tyr Val Tyr
            20                  25

<210> SEQ ID NO: 71
<211> LENGTH: 8
<212> TYPE: PRT
<213> ORGANISM: Arabidopsis sp.

<400> SEQUENCE: 71

Ile Gly Glu Glu Cys Asp Arg Ser
 1               5
```

<210> SEQ ID NO: 72
<211> LENGTH: 4
<212> TYPE: PRT
<213> ORGANISM: Arabidopsis sp.

<400> SEQUENCE: 72

Ser Cys Asp Gly
 1

<210> SEQ ID NO: 73
<211> LENGTH: 28
<212> TYPE: PRT
<213> ORGANISM: Arabidopsis sp.

<400> SEQUENCE: 73

Leu Tyr Ile Lys Gln Asp Cys Gly Leu Arg Ser Lys Gln His Tyr Val
 1               5                  10                  15

Asp Ala Cys Arg Glu Gly Ser Leu Leu Glu Arg Asn
             20                  25

<210> SEQ ID NO: 74
<211> LENGTH: 9
<212> TYPE: PRT
<213> ORGANISM: Arabidopsis sp.

<400> SEQUENCE: 74

Asp Ile Trp Glu Lys Gln Val Lys Lys
 1               5

<210> SEQ ID NO: 75
<211> LENGTH: 18
<212> TYPE: PRT
<213> ORGANISM: Arabidopsis sp.

<400> SEQUENCE: 75

Cys Ile Asn Ile Tyr Thr Tyr Thr Val Phe Leu Asp Tyr Ala Gly Ser
 1               5                  10                  15

Gln Leu

<210> SEQ ID NO: 76
<211> LENGTH: 9
<212> TYPE: PRT
<213> ORGANISM: Arabidopsis sp.

<400> SEQUENCE: 76

Cys Cys Ile Lys His Thr Ser Gly Ala
 1               5

<210> SEQ ID NO: 77
<211> LENGTH: 21
<212> TYPE: PRT
<213> ORGANISM: Arabidopsis sp.

<400> SEQUENCE: 77

Asp Val Pro Arg Asp Leu Gln Leu His Ala Arg Thr Arg Ser Met Tyr
 1               5                  10                  15

Tyr Val Ile Arg Pro
             20

<210> SEQ ID NO: 78
<211> LENGTH: 32
<212> TYPE: PRT

-continued

<213> ORGANISM: Arabidopsis sp.

<400> SEQUENCE: 78

Gln Asn Tyr Thr Lys Thr Gln Ser Gly Thr Leu Thr Tyr Val Val Ile
 1               5                  10                  15

Ile Leu Met Thr Cys Met Leu Lys Thr His Glu Val Ser Tyr Met Cys
                20                  25                  30

<210> SEQ ID NO: 79
<211> LENGTH: 33
<212> TYPE: PRT
<213> ORGANISM: Arabidopsis sp.

<400> SEQUENCE: 79

Trp Phe Tyr His Arg Leu Pro Lys Lys Tyr Leu Glu Lys Val Val Gly
 1               5                  10                  15

Arg Ser Ala Lys Asn Arg Asp Ser Glu Asn Met Leu Val Ile Arg Leu
                20                  25                  30

Leu

<210> SEQ ID NO: 80
<211> LENGTH: 29
<212> TYPE: PRT
<213> ORGANISM: Arabidopsis sp.

<400> SEQUENCE: 80

Arg Lys Gln Leu Val Glu Lys Leu Ser Phe Ile Ser Thr Thr His His
 1               5                  10                  15

Ala Leu Ala Ser Gln Asn Val Asp Ser Asn Ala Leu Val
                20                  25

<210> SEQ ID NO: 81
<211> LENGTH: 17
<212> TYPE: PRT
<213> ORGANISM: Arabidopsis sp.

<400> SEQUENCE: 81

Leu Thr Lys Ile Ala Ala Arg Asn Ile Ala Gly Met Ser Phe Asn Phe
 1               5                  10                  15

Ser

<210> SEQ ID NO: 82
<211> LENGTH: 62
<212> TYPE: PRT
<213> ORGANISM: Arabidopsis sp.

<400> SEQUENCE: 82

Ala Gly Arg Ser Met Arg Phe Asn Leu Asn Met Ser Leu Tyr Phe Leu
 1               5                  10                  15

Phe Arg Cys Ser Lys Asp Cys Asn Asn Arg Phe Gly Gly Cys Asn Cys
                20                  25                  30

Ala Ile Gly Gln Cys Thr Asn Arg Gln Cys Pro Cys Phe Ala Ala Asn
            35                  40                  45

Arg Glu Cys Asp Pro Asp Leu Cys Arg Ser Cys Pro Leu Arg
        50                  55                  60

<210> SEQ ID NO: 83
<211> LENGTH: 66
<212> TYPE: PRT
<213> ORGANISM: Arabidopsis sp.

```
<400> SEQUENCE: 83

His Phe His Phe Asn Ile Ser Leu Tyr Lys Phe Tyr Asn Gln Ser Asn
 1               5                  10                  15

Ser Asn Gln Lys Ser Tyr Lys Lys Asn Phe Ile Tyr Ser Cys Gly Asp
             20                  25                  30

Gly Thr Leu Gly Glu Thr Pro Val Gln Ile Gln Cys Lys Asn Met Gln
         35                  40                  45

Phe Leu Leu Gln Thr Asn Lys Lys Val Ile Asn Val Lys Ser Val Pro
     50                  55                  60

Lys Ile
 65

<210> SEQ ID NO: 84
<211> LENGTH: 20
<212> TYPE: PRT
<213> ORGANISM: Arabidopsis sp.

<400> SEQUENCE: 84

Leu Tyr Glu Arg His Leu Thr Ile Ile Ser Arg Ile Leu Leu Asp Ser
 1               5                  10                  15

His Trp Lys Val
             20

<210> SEQ ID NO: 85
<211> LENGTH: 41
<212> TYPE: PRT
<213> ORGANISM: Arabidopsis sp.

<400> SEQUENCE: 85

Cys Ser Trp Met Gly Cys Ile Tyr Met Gly Lys Gln Ser Cys Lys Tyr
 1               5                  10                  15

Lys Asn Lys Phe Asn Ser Tyr Trp Cys Ile His Asn Thr Phe Phe Phe
             20                  25                  30

Leu Ile Met Phe Tyr Thr Leu Asp His
         35                  40

<210> SEQ ID NO: 86
<211> LENGTH: 13
<212> TYPE: PRT
<213> ORGANISM: Arabidopsis sp.

<400> SEQUENCE: 86

Ile Tyr Cys Val Ile Trp Phe Asp Pro Ser Gly Leu Ser
 1               5                  10

<210> SEQ ID NO: 87
<211> LENGTH: 12
<212> TYPE: PRT
<213> ORGANISM: Arabidopsis sp.

<400> SEQUENCE: 87

Val Ser Arg Arg Ile Tyr Trp Arg Thr Asp His Ser
 1               5                  10

<210> SEQ ID NO: 88
<211> LENGTH: 17
<212> TYPE: PRT
<213> ORGANISM: Arabidopsis sp.

<400> SEQUENCE: 88

Ala Trp Glu Asn Arg Arg Ser Asp Trp Phe Phe Leu Pro Leu Tyr Leu
```

```
            1               5                  10                 15
Glu

<210> SEQ ID NO: 89
<211> LENGTH: 9
<212> TYPE: PRT
<213> ORGANISM: Arabidopsis sp.

<400> SEQUENCE: 89

Ser Gly Asn Phe Arg Ile Ile Leu Lys
  1               5

<210> SEQ ID NO: 90
<211> LENGTH: 14
<212> TYPE: PRT
<213> ORGANISM: Arabidopsis sp.

<400> SEQUENCE: 90

Arg Phe Asn His Ser Arg Val Thr His Leu Phe Glu Ser Lys
  1               5                  10

<210> SEQ ID NO: 91
<211> LENGTH: 32
<212> TYPE: PRT
<213> ORGANISM: Arabidopsis sp.

<400> SEQUENCE: 91

His Leu Phe Tyr Ser Ser Lys Ser Met Leu Ala Val Lys Glu Thr Ser
  1               5                  10                 15

Ser Asn Phe Ser Ile Thr Gln Gln Asp Leu Thr Ala Thr Pro Arg Tyr
                20                 25                  30

<210> SEQ ID NO: 92
<211> LENGTH: 19
<212> TYPE: PRT
<213> ORGANISM: Arabidopsis sp.

<400> SEQUENCE: 92

Ala Val Ile Leu Tyr Leu Glu Gln Ile Leu Thr Leu Tyr Lys Gln Lys
  1               5                  10                 15

Tyr Leu Cys

<210> SEQ ID NO: 93
<211> LENGTH: 15
<212> TYPE: PRT
<213> ORGANISM: Arabidopsis sp.

<400> SEQUENCE: 93

Leu Asn Arg Val Ser Thr Leu Val Val Asp Trp Phe Ser Tyr
  1               5                  10                 15

<210> SEQ ID NO: 94
<211> LENGTH: 50
<212> TYPE: PRT
<213> ORGANISM: Arabidopsis sp.

<400> SEQUENCE: 94

Arg Tyr Ser Lys Lys Leu Lys Leu Ile Leu Asn Asp Phe Phe Leu Ser
  1               5                  10                 15

Arg Lys Phe Arg Leu Arg Lys Phe Met Val Ser Cys Ala Val Asp Asp
                20                 25                  30

Cys Glu Arg Arg Ser Glu Asp Trp Ser Ile Cys Gly Glu Ser Asn Arg
```

```
                35                  40                  45

Arg Arg
    50

<210> SEQ ID NO: 95
<211> LENGTH: 21
<212> TYPE: PRT
<213> ORGANISM: Arabidopsis sp.

<400> SEQUENCE: 95

Gly Ala Phe Leu Arg Leu Leu Leu Trp Thr Arg Thr Cys Gly Leu Val
 1               5                  10                  15

Ala Trp Ser Arg Thr
            20

<210> SEQ ID NO: 96
<211> LENGTH: 5
<212> TYPE: PRT
<213> ORGANISM: Arabidopsis sp.

<400> SEQUENCE: 96

Lys Asp Trp Cys Phe
 1               5

<210> SEQ ID NO: 97
<211> LENGTH: 28
<212> TYPE: PRT
<213> ORGANISM: Arabidopsis sp.

<400> SEQUENCE: 97

Gly Ser Pro Ser Ser Ser Leu Val Phe Asp Leu Arg Arg Ser Ser Asn
 1               5                  10                  15

Ser Ser Ser Pro Phe Phe Met Leu Trp Tyr Ile Asn
            20                  25

<210> SEQ ID NO: 98
<211> LENGTH: 7
<212> TYPE: PRT
<213> ORGANISM: Arabidopsis sp.

<400> SEQUENCE: 98

Cys Asn Ala Ile Leu Cys Tyr
 1               5

<210> SEQ ID NO: 99
<211> LENGTH: 52
<212> TYPE: PRT
<213> ORGANISM: Arabidopsis sp.

<400> SEQUENCE: 99

Val Ser Val Leu Phe Val Leu Gly Cys Phe Val Cys Ile Ile Cys Val
 1               5                  10                  15

Leu Thr Phe Lys Val Phe Phe Leu Tyr Phe Asn Leu Lys Thr Met Phe
                20                  25                  30

Met Leu Leu Val Cys Ile Asp Leu Trp Lys Lys Lys Ala Leu His Asn
            35                  40                  45

Phe Thr Phe Ile
    50

<210> SEQ ID NO: 100
<211> LENGTH: 33
<212> TYPE: PRT
```

```
<213> ORGANISM: Arabidopsis sp.

<400> SEQUENCE: 100

Ser Ser Phe Ser Glu Lys Ser His Asn Thr Ser Leu Trp Tyr Val Met
 1               5                  10                  15

Tyr Lys Asn Val Lys Ile Met Gly Phe Ile Ile Lys Lys Lys Tyr Trp
                20                  25                  30

Leu

<210> SEQ ID NO: 101
<211> LENGTH: 4
<212> TYPE: PRT
<213> ORGANISM: Arabidopsis sp.

<400> SEQUENCE: 101

Met Lys Tyr Ser
 1

<210> SEQ ID NO: 102
<211> LENGTH: 4
<212> TYPE: PRT
<213> ORGANISM: Arabidopsis sp.

<400> SEQUENCE: 102

Asn Phe Arg Tyr
 1

<210> SEQ ID NO: 103
<211> LENGTH: 4
<212> TYPE: PRT
<213> ORGANISM: Arabidopsis sp.

<400> SEQUENCE: 103

Leu Val Trp Phe
 1

<210> SEQ ID NO: 104
<211> LENGTH: 8
<212> TYPE: PRT
<213> ORGANISM: Arabidopsis sp.

<400> SEQUENCE: 104

Asn Val Phe Arg Asp Leu Ile Leu
 1               5

<210> SEQ ID NO: 105
<211> LENGTH: 10
<212> TYPE: PRT
<213> ORGANISM: Arabidopsis sp.

<400> SEQUENCE: 105

Tyr Met Glu Glu Ser Ser Thr Lys Trp Leu
 1               5                  10

<210> SEQ ID NO: 106
<211> LENGTH: 8
<212> TYPE: PRT
<213> ORGANISM: Arabidopsis sp.

<400> SEQUENCE: 106

Leu Thr Lys Gly Phe Thr Leu Met
 1               5
```

```
<210> SEQ ID NO: 107
<211> LENGTH: 16
<212> TYPE: PRT
<213> ORGANISM: Arabidopsis sp.

<400> SEQUENCE: 107

His Leu Val Ser Lys Gln Ile Lys Thr Lys Lys Lys Lys Lys Ala Leu
 1               5                  10                  15

<210> SEQ ID NO: 108
<211> LENGTH: 12
<212> TYPE: PRT
<213> ORGANISM: Arabidopsis sp.

<400> SEQUENCE: 108

Asn Pro Lys Val Thr Ile Phe Lys Lys Ser Lys Leu
 1               5                  10

<210> SEQ ID NO: 109
<211> LENGTH: 9
<212> TYPE: PRT
<213> ORGANISM: Arabidopsis sp.

<400> SEQUENCE: 109

Met Phe Gly Ile Ala Asn Asp Tyr Cys
 1               5

<210> SEQ ID NO: 110
<211> LENGTH: 17
<212> TYPE: PRT
<213> ORGANISM: Arabidopsis sp.

<400> SEQUENCE: 110

Met Leu Asn Ile His Glu Asp Val Lys Asn Met Leu Asp Leu Trp Asn
 1               5                  10                  15

Arg

<210> SEQ ID NO: 111
<211> LENGTH: 7
<212> TYPE: PRT
<213> ORGANISM: Arabidopsis sp.

<400> SEQUENCE: 111

Pro Arg Leu Asn Gly Gly Ile
 1               5

<210> SEQ ID NO: 112
<211> LENGTH: 38
<212> TYPE: PRT
<213> ORGANISM: Arabidopsis sp.

<400> SEQUENCE: 112

Asp Pro Leu Phe Leu Lys Ile Lys Phe Phe His Ile Tyr Tyr Leu Phe
 1               5                  10                  15

Gln Arg Lys Lys Lys His Thr Thr Ile Ile His Leu Pro Ala Val Phe
                20                  25                  30

Ile Gly Lys Pro Ile Phe
                35

<210> SEQ ID NO: 113
<211> LENGTH: 16
<212> TYPE: PRT
<213> ORGANISM: Arabidopsis sp.
```

-continued

```
<400> SEQUENCE: 113

Asn Trp Trp Ala Phe His Tyr His Lys Phe Gly His Val Phe Ile Ile
 1               5                  10                  15

<210> SEQ ID NO: 114
<211> LENGTH: 33
<212> TYPE: PRT
<213> ORGANISM: Arabidopsis sp.

<400> SEQUENCE: 114

Arg Asn Lys Lys Gly Asn Leu Cys Gly Asp Cys Asn Lys Thr Glu Ile
 1               5                  10                  15

Ile Ile Leu Asn His Ser Lys Arg Arg Lys Asp Gln Thr Phe Val Ala
                20                  25                  30

Arg

<210> SEQ ID NO: 115
<211> LENGTH: 59
<212> TYPE: PRT
<213> ORGANISM: Arabidopsis sp.

<400> SEQUENCE: 115

Thr Trp Leu Pro Ile Thr Val Leu Met Leu Leu Tyr Arg Ser Phe Leu
 1               5                  10                  15

His Pro Leu Phe Leu His Ile Gln Glu Thr Val Ser Ser His Phe Leu
                20                  25                  30

Ser Ser Ser Gln Cys Phe Asn Leu Cys Glu Leu Arg Trp Asn Met Lys
            35                  40                  45

Lys His Lys Arg Thr Gln Glu Thr Ala Gly Pro
        50                  55

<210> SEQ ID NO: 116
<211> LENGTH: 5
<212> TYPE: PRT
<213> ORGANISM: Arabidopsis sp.

<400> SEQUENCE: 116

Phe Asp His Phe Lys
 1               5

<210> SEQ ID NO: 117
<211> LENGTH: 57
<212> TYPE: PRT
<213> ORGANISM: Arabidopsis sp.

<400> SEQUENCE: 117

Ser Pro Leu Ala Phe Leu Ala Ser Ser Leu Tyr Leu Ser Ser Phe
 1               5                  10                  15

Phe His Val Ser Leu Ser Ile Pro Pro Gln Leu Arg Ser Pro Ser Pro
                20                  25                  30

Ala Phe Pro Leu Leu Phe Thr Arg Gln Met Ser Glu Ser Tyr Thr Arg
            35                  40                  45

Ser Cys Phe Ser Ser Ser Ser Ser Leu
        50                  55

<210> SEQ ID NO: 118
<211> LENGTH: 37
<212> TYPE: PRT
<213> ORGANISM: Arabidopsis sp.

<400> SEQUENCE: 118
```

Ser Thr Val Ser Gln Glu Asn Gln Asn Ala Leu Phe Ser Ile Pro Ile
1               5                   10                  15

Ser Thr Ser Ala Gly Ser Phe Ser Ser Pro Lys Leu Val Pro Leu
            20                  25                  30

Gly Ser Lys Glu Pro
            35

<210> SEQ ID NO: 119
<211> LENGTH: 5
<212> TYPE: PRT
<213> ORGANISM: Arabidopsis sp.

<400> SEQUENCE: 119

Ala Arg Pro Cys Leu
1               5

<210> SEQ ID NO: 120
<211> LENGTH: 27
<212> TYPE: PRT
<213> ORGANISM: Arabidopsis sp.

<400> SEQUENCE: 120

Ile Gln Thr Lys Thr Cys Phe Leu Arg His Met Lys Asp Gly Cys Trp
1               5                   10                  15

Leu Gly Phe Cys Ser Phe Trp Gly Tyr Thr Lys
            20                  25

<210> SEQ ID NO: 121
<211> LENGTH: 31
<212> TYPE: PRT
<213> ORGANISM: Arabidopsis sp.

<400> SEQUENCE: 121

Cys Gly Leu Glu Ser Trp Leu Ser Leu Trp Leu Thr Thr Leu Tyr Met
1               5                   10                  15

Gly Ser Thr Trp Arg Arg Gly Gly Pro Arg Glu Pro Leu Trp Gln
            20                  25                  30

<210> SEQ ID NO: 122
<211> LENGTH: 5
<212> TYPE: PRT
<213> ORGANISM: Arabidopsis sp.

<400> SEQUENCE: 122

Cys Gly Gly Gly Gly
1               5

<210> SEQ ID NO: 123
<211> LENGTH: 23
<212> TYPE: PRT
<213> ORGANISM: Arabidopsis sp.

<400> SEQUENCE: 123

Lys Val Leu Trp Trp Trp Leu Arg Arg Ile Asp Leu Thr Ser Pro Phe
1               5                   10                  15

Val Trp Arg Val Ser Ile Leu
            20

<210> SEQ ID NO: 124
<211> LENGTH: 12
<212> TYPE: PRT
<213> ORGANISM: Arabidopsis sp.

<400> SEQUENCE: 124

Thr Gly Val Cys Ile Thr Ser Val Leu Glu Leu Val
 1               5                  10

<210> SEQ ID NO: 125
<211> LENGTH: 9
<212> TYPE: PRT
<213> ORGANISM: Arabidopsis sp.

<400> SEQUENCE: 125

Arg Ser Ser Lys Gly Phe Trp Ile Leu
 1               5

<210> SEQ ID NO: 126
<211> LENGTH: 36
<212> TYPE: PRT
<213> ORGANISM: Arabidopsis sp.

<400> SEQUENCE: 126

Ala Leu Arg Gly Arg Glu Lys Ala Val Asn His Val Phe Leu Met Ile
 1               5                  10                  15

Cys Val Met Met Ile Met Cys Lys Ile Phe Asp Ile Leu Tyr Ser Ser
                20                  25                  30

Leu Glu Cys Phe
            35

<210> SEQ ID NO: 127
<211> LENGTH: 13
<212> TYPE: PRT
<213> ORGANISM: Arabidopsis sp.

<400> SEQUENCE: 127

Asp Phe Phe Ile Phe Ile Phe Tyr Phe Leu Leu Gly Ile
 1               5                  10

<210> SEQ ID NO: 128
<211> LENGTH: 7
<212> TYPE: PRT
<213> ORGANISM: Arabidopsis sp.

<400> SEQUENCE: 128

Pro Val Tyr Met Ser Gln Lys
 1               5

<210> SEQ ID NO: 129
<211> LENGTH: 9
<212> TYPE: PRT
<213> ORGANISM: Arabidopsis sp.

<400> SEQUENCE: 129

Asn Ile Arg Lys Gln Lys Tyr Phe Ile
 1               5

<210> SEQ ID NO: 130
<211> LENGTH: 14
<212> TYPE: PRT
<213> ORGANISM: Arabidopsis sp.

<400> SEQUENCE: 130

Pro Leu Asn Ile Asn Leu Ser Leu Phe Ile Ile Ile Phe Leu
 1               5                  10

<210> SEQ ID NO: 131
<211> LENGTH: 10
<212> TYPE: PRT
<213> ORGANISM: Arabidopsis sp.

<400> SEQUENCE: 131

His Thr Leu Phe Lys Lys Asn Leu Glu Ile
 1               5                  10

<210> SEQ ID NO: 132
<211> LENGTH: 8
<212> TYPE: PRT
<213> ORGANISM: Arabidopsis sp.

<400> SEQUENCE: 132

Ile Val Lys Asn Ile Gly Phe Thr
 1               5

<210> SEQ ID NO: 133
<211> LENGTH: 8
<212> TYPE: PRT
<213> ORGANISM: Arabidopsis sp.

<400> SEQUENCE: 133

Met Arg Ile Ile Lys Phe Thr Asn
 1               5

<210> SEQ ID NO: 134
<211> LENGTH: 5
<212> TYPE: PRT
<213> ORGANISM: Arabidopsis sp.

<400> SEQUENCE: 134

Pro Tyr Ile Tyr Phe
 1               5

<210> SEQ ID NO: 135
<211> LENGTH: 14
<212> TYPE: PRT
<213> ORGANISM: Arabidopsis sp.

<400> SEQUENCE: 135

Arg Phe Lys Leu Ile Leu Phe Leu Pro Tyr Met His Asn Ile
 1               5                  10

<210> SEQ ID NO: 136
<211> LENGTH: 39
<212> TYPE: PRT
<213> ORGANISM: Arabidopsis sp.

<400> SEQUENCE: 136

Leu Gly Met Asn Thr Asn Ile Tyr Asn Asp Ile Asn Ile Ser Leu Thr
 1               5                  10                  15

Gly His Ser Lys Met Tyr Ile Leu Ile Tyr Gln His Phe Phe Ile Gly
                20                  25                  30

Leu Leu Asn Gln Val Val Thr
            35

<210> SEQ ID NO: 137
<211> LENGTH: 35
<212> TYPE: PRT
<213> ORGANISM: Arabidopsis sp.

<400> SEQUENCE: 137

-continued

Val Asn Ala Phe Phe Phe Ile Ile Leu Tyr Met Asn Leu Asn Leu Ser
1               5                   10                  15

Cys Gln Thr Ser Ser Lys Pro Asn Ile Tyr Ile His Ile Val Leu Tyr
                20                  25                  30

Phe Glu Asn
        35

<210> SEQ ID NO: 138
<211> LENGTH: 11
<212> TYPE: PRT
<213> ORGANISM: Arabidopsis sp.

<400> SEQUENCE: 138

Asn Phe Leu Lys Phe Pro Ile Leu Phe Ser Phe
1               5                   10

<210> SEQ ID NO: 139
<211> LENGTH: 55
<212> TYPE: PRT
<213> ORGANISM: Arabidopsis sp.

<400> SEQUENCE: 139

Ser Lys Gln Val Gln Ile Arg Phe Phe Gln Ile Ile Ile Phe Leu Asn
1               5                   10                  15

Lys Val Phe Tyr Lys Lys Lys Ser Thr Ser Tyr Leu Lys Asn Pro Leu
                20                  25                  30

His Tyr Pro Phe His Gln His Gln Arg Arg Arg Glu Lys Lys Lys Arg
            35                  40                  45

Arg Val Val Asn Gly Glu Gly
        50                  55

<210> SEQ ID NO: 140
<211> LENGTH: 6
<212> TYPE: PRT
<213> ORGANISM: Arabidopsis sp.

<400> SEQUENCE: 140

Phe His Ser Lys His Ile
1               5

<210> SEQ ID NO: 141
<211> LENGTH: 15
<212> TYPE: PRT
<213> ORGANISM: Arabidopsis sp.

<400> SEQUENCE: 141

Val Met Lys Ser Ile Tyr Phe Asn Cys Val Phe Met Ile Asp Gln
1               5                   10                  15

<210> SEQ ID NO: 142
<211> LENGTH: 19
<212> TYPE: PRT
<213> ORGANISM: Arabidopsis sp.

<400> SEQUENCE: 142

His Leu Gly Leu Asn Phe Leu Val Ile Tyr Tyr Val Ile Arg Pro Met
1               5                   10                  15

His Asp Pro

<210> SEQ ID NO: 143
<211> LENGTH: 4
<212> TYPE: PRT

<213> ORGANISM: Arabidopsis sp.

<400> SEQUENCE: 143

Asn Phe Tyr Phe
 1

<210> SEQ ID NO: 144
<211> LENGTH: 6
<212> TYPE: PRT
<213> ORGANISM: Arabidopsis sp.

<400> SEQUENCE: 144

Ile Cys Leu Gly Lys Pro
 1               5

<210> SEQ ID NO: 145
<211> LENGTH: 107
<212> TYPE: PRT
<213> ORGANISM: Arabidopsis sp.

<400> SEQUENCE: 145

Gly Phe Ala Thr Arg Thr Lys Ser Asp Lys Arg Ala Asn Arg Lys Gly
 1               5                  10                  15

Glu Ile Ser Ala Tyr Gln Gly Lys Arg His Leu Val Ala Leu Ile Phe
             20                  25                  30

Tyr Ser Leu Leu Tyr Val Phe Leu Lys Ile Lys Glu Arg Arg Gly Leu
         35                  40                  45

Asn Leu Ile Thr Ile Arg Phe Gln Arg Asp Val Lys Ile His Leu Ile
     50                  55                  60

Asn Ser Tyr Thr Leu Val Ile Ile Phe Lys Thr Lys Lys Arg Asn Phe
 65                  70                  75                  80

Gln Thr Phe Lys Leu Lys Thr Glu Phe Arg Lys Cys Gln Arg Ile Asp
                 85                  90                  95

Asn Asp Ile Gln Ile Cys Arg Val Ser Lys Thr
            100                 105

<210> SEQ ID NO: 146
<211> LENGTH: 10
<212> TYPE: PRT
<213> ORGANISM: Arabidopsis sp.

<400> SEQUENCE: 146

Asn Lys Lys Ile Ile Asn Ile Phe Ile Ile
 1               5                  10

<210> SEQ ID NO: 147
<211> LENGTH: 30
<212> TYPE: PRT
<213> ORGANISM: Arabidopsis sp.

<400> SEQUENCE: 147

Ser Trp Asn Leu Gly Tyr Lys Ile Lys Leu Lys Ile Ile Val Asp Phe
 1               5                  10                  15

Phe Val Phe Val Lys Gln Asn Ser Asn Thr Ile Cys Phe Phe
             20                  25                  30

<210> SEQ ID NO: 148
<211> LENGTH: 5
<212> TYPE: PRT
<213> ORGANISM: Arabidopsis sp.

<400> SEQUENCE: 148

Tyr Lys Glu Thr Lys
 1               5

<210> SEQ ID NO: 149
<211> LENGTH: 15
<212> TYPE: PRT
<213> ORGANISM: Arabidopsis sp.

<400> SEQUENCE: 149

Val Gln Ile Val Phe Phe Leu Thr Phe Ser Gln Lys Ser Gln Asp
 1               5                  10                  15

<210> SEQ ID NO: 150
<211> LENGTH: 38
<212> TYPE: PRT
<213> ORGANISM: Arabidopsis sp.

<400> SEQUENCE: 150

Cys Ile Tyr Gln Glu Ile Glu Ile Lys Thr Phe Val Phe Lys Tyr Ser
 1               5                  10                  15

Ser Phe Thr Ile Tyr Arg Val Gln Phe Leu Lys Phe Lys Ser Phe
            20                  25                  30

Thr Tyr Ile Leu Leu Asp
        35

<210> SEQ ID NO: 151
<211> LENGTH: 147
<212> TYPE: PRT
<213> ORGANISM: Arabidopsis sp.

<400> SEQUENCE: 151

Gln Arg Lys Phe Glu Leu Arg Tyr Ile Pro Ser Val Ala Thr His Ala
 1               5                  10                  15

Ser His His Gln Ser Phe Asp Leu Asn Gln Pro Ala Ala Glu Asp Asp
            20                  25                  30

Asn Gly Gly Asp Asn Lys Ser Leu Leu Ser Arg Met Gln Asn Pro Leu
        35                  40                  45

Arg His Phe Ser Ala Ser Ser Asp Tyr Asn Ser Tyr Glu Asp Gln Gly
    50                  55                  60

Tyr Val Leu Asp Glu Asp Gln Asp Tyr Ala Leu Glu Glu Asp Val Pro
65                  70                  75                  80

Leu Phe Leu Asp Glu Asp Val Pro Leu Leu Pro Ser Val Lys Leu Pro
                85                  90                  95

Ile Val Glu Lys Leu Pro Arg Ser Ile Thr Trp Val Phe Thr Lys Arg
            100                 105                 110

His Val Cys Phe Leu Phe Arg Thr Ser Phe Lys Ile Leu Ile Ile Tyr
        115                 120                 125

Tyr Ile Val Ile Thr His Ser Ala Tyr Ile His Phe Phe Asn Ile Ala
    130                 135                 140

Val Ala Ser
145

<210> SEQ ID NO: 152
<211> LENGTH: 6
<212> TYPE: PRT
<213> ORGANISM: Arabidopsis sp.

<400> SEQUENCE: 152

Trp Leu Lys Val Ile Leu

<210> SEQ ID NO: 153
<211> LENGTH: 8
<212> TYPE: PRT
<213> ORGANISM: Arabidopsis sp.

<400> SEQUENCE: 153

Leu Val Arg Asp Lys Ser Ile Ile
1               5

<210> SEQ ID NO: 154
<211> LENGTH: 4
<212> TYPE: PRT
<213> ORGANISM: Arabidopsis sp.

<400> SEQUENCE: 154

Met Val Arg His
1

<210> SEQ ID NO: 155
<211> LENGTH: 26
<212> TYPE: PRT
<213> ORGANISM: Arabidopsis sp.

<400> SEQUENCE: 155

Ala Val Lys Lys Met Arg Lys Met Lys Lys Met Arg Lys Lys Ser
1               5                  10                  15

Arg Lys Lys Asn Ala Asn Phe Leu Lys Met
            20                  25

<210> SEQ ID NO: 156
<211> LENGTH: 5
<212> TYPE: PRT
<213> ORGANISM: Arabidopsis sp.

<400> SEQUENCE: 156

Thr Asp Leu Tyr Gly
1               5

<210> SEQ ID NO: 157
<211> LENGTH: 7
<212> TYPE: PRT
<213> ORGANISM: Arabidopsis sp.

<400> SEQUENCE: 157

Phe Leu His Tyr Ile Cys Ser
1               5

<210> SEQ ID NO: 158
<211> LENGTH: 25
<212> TYPE: PRT
<213> ORGANISM: Arabidopsis sp.

<400> SEQUENCE: 158

Leu Leu Ile Cys Ser Pro Tyr Leu Ile Asn Cys Ser Arg Asn Phe Gln
1               5                  10                  15

Asp Gly Trp Ala Gly Leu Trp Phe Gly
            20                  25

<210> SEQ ID NO: 159
<211> LENGTH: 32
<212> TYPE: PRT
<213> ORGANISM: Arabidopsis sp.

<400> SEQUENCE: 159

Ser Gly Arg Ala Ala Cys Ser Arg Gln Val Pro Arg Ser Gly Cys Phe
1               5                   10                  15

Gly His Ile Gly Asn Asn Ile Arg Ile Lys Thr Ser Tyr Val Asp Gln
            20                  25                  30

<210> SEQ ID NO: 160
<211> LENGTH: 12
<212> TYPE: PRT
<213> ORGANISM: Arabidopsis sp.

<400> SEQUENCE: 160

Leu Ser Cys Leu Phe Asn Phe Cys Cys Phe Ser Ser
1               5                   10

<210> SEQ ID NO: 161
<211> LENGTH: 10
<212> TYPE: PRT
<213> ORGANISM: Arabidopsis sp.

<400> SEQUENCE: 161

Ile Phe Lys Ser Asn Val Gly Lys Ile Gln
1               5                   10

<210> SEQ ID NO: 162
<211> LENGTH: 4
<212> TYPE: PRT
<213> ORGANISM: Arabidopsis sp.

<400> SEQUENCE: 162

Trp Asn Cys Trp
1

<210> SEQ ID NO: 163
<211> LENGTH: 14
<212> TYPE: PRT
<213> ORGANISM: Arabidopsis sp.

<400> SEQUENCE: 163

Phe Asp Ile Gln Asp Asn Asn Tyr Cys Phe Pro Gly Phe Cys
1               5                   10

<210> SEQ ID NO: 164
<211> LENGTH: 59
<212> TYPE: PRT
<213> ORGANISM: Arabidopsis sp.

<400> SEQUENCE: 164

Thr Ser Leu Pro Ser Leu His Gly Asn Phe Glu Ser Phe Phe Phe Asn
1               5                   10                  15

Leu Ala Thr Lys Lys Gly Asp Asp His Thr Cys Phe Tyr Phe Ile Leu
            20                  25                  30

Ser Phe Val Leu Gln Ile Phe Asp Cys His Met His Glu Lys Tyr Glu
                35                  40                  45

Pro Glu Ser Arg Ser Val Ser Ile Lys Phe Ile
        50                  55

<210> SEQ ID NO: 165
<211> LENGTH: 15
<212> TYPE: PRT
<213> ORGANISM: Arabidopsis sp.

-continued

```
<400> SEQUENCE: 165

Ile Ile Leu Leu Val Ser Gln Pro Leu Tyr Ile Arg Leu Ser Asp
 1               5                  10                  15

<210> SEQ ID NO: 166
<211> LENGTH: 56
<212> TYPE: PRT
<213> ORGANISM: Arabidopsis sp.

<400> SEQUENCE: 166

Ile Ala Leu Ala Cys Gln Ser Glu Asp Lys Ser Ser Leu Phe Glu Asp
 1               5                  10                  15

Glu Asp Arg Gln Pro Cys Ser Glu His Cys Tyr Leu Lys Val Ser Ile
            20                  25                  30

Ser Leu Pro Leu Ser Leu Asn Phe Phe Val Tyr Ser Leu Ile Thr Phe
        35                  40                  45

Ile Ser Tyr Trp Phe Asn Ile Lys
    50                  55

<210> SEQ ID NO: 167
<211> LENGTH: 50
<212> TYPE: PRT
<213> ORGANISM: Arabidopsis sp.

<400> SEQUENCE: 167

Val Arg Ser Val Thr Glu Ala Asp His Val Met Asp Asn Asp Asn Ser
 1               5                  10                  15

Ile Ser Asn Lys Ile Val Val Ser Asp Pro Asn Asn Thr Met Trp Thr
            20                  25                  30

Pro Val Glu Lys Asp Leu Tyr Leu Lys Gly Ile Glu Ile Phe Gly Arg
        35                  40                  45

Asn Arg
    50

<210> SEQ ID NO: 168
<211> LENGTH: 68
<212> TYPE: PRT
<213> ORGANISM: Arabidopsis sp.

<400> SEQUENCE: 168

Lys Asn Lys Asn Arg Phe Asn Ala Leu Ile Tyr Ile Leu Thr Leu Tyr
 1               5                  10                  15

Ser Leu Ile Met Leu Val Arg Ser Cys Asp Val Ala Leu Asn Ile Leu
            20                  25                  30

Arg Gly Leu Lys Thr Cys Leu Glu Ile Tyr Asn Tyr Met Arg Glu Gln
        35                  40                  45

Asp Gln Cys Thr Met Ser Leu Asp Leu Asn Lys Thr Thr Gln Arg His
    50                  55                  60

Asn Gln Val His
65

<210> SEQ ID NO: 169
<211> LENGTH: 23
<212> TYPE: PRT
<213> ORGANISM: Arabidopsis sp.

<400> SEQUENCE: 169

Lys His Met Lys Phe Pro Ile Cys Val Asp Gly Phe Ile Thr Gly Tyr
 1               5                  10                  15
```

-continued

Gln Lys Ser Ile Ser Lys Lys
            20

<210> SEQ ID NO: 170
<211> LENGTH: 22
<212> TYPE: PRT
<213> ORGANISM: Arabidopsis sp.

<400> SEQUENCE: 170

Val Gly Pro Gln Lys Ile Glu Thr Pro Lys Ile Cys Ser Leu Ser Ala
1               5                   10                  15

Cys Phe Lys Glu Asn Asn
            20

<210> SEQ ID NO: 171
<211> LENGTH: 41
<212> TYPE: PRT
<213> ORGANISM: Arabidopsis sp.

<400> SEQUENCE: 171

Ala Leu His Thr Met His Leu Gln Val Lys Met Trp Thr Ala Met Pro
1               5                   10                  15

Leu Phe Asn Ser Arg Lys Leu Leu Arg Glu Ile Leu Arg Val Cys His
            20                  25                  30

Ser Ile Phe Pro Lys Pro Glu Asp Pro
            35                  40

<210> SEQ ID NO: 172
<211> LENGTH: 108
<212> TYPE: PRT
<213> ORGANISM: Arabidopsis sp.

<400> SEQUENCE: 172

Val Cys Ile Phe Cys Ser Gly Ala Gln Arg Ile Ala Thr Ile Ala Leu
1               5                   10                  15

Glu Asp Val Ile Val Gln Leu Ala Asn Ala Gln Ile Asp Asn Val Leu
            20                  25                  30

Val Leu Leu Leu Ile Val Asn Ala Ile Gln Ile Phe Val Gly Val Val
            35                  40                  45

Leu Leu Gly Asn Thr Phe Thr Ser Ile Ser Leu Tyr Thr Asn Ser Ile
        50                  55                  60

Ile Lys Val Ile Gln Thr Lys Ser Leu Ile Lys Lys Thr Leu Tyr Ile
65                  70                  75                  80

Ala Val Glu Met Ala Leu Leu Val Arg His Gln Cys Lys Ser Asn Ala
                85                  90                  95

Arg Thr Cys Asn Ser Ser Phe Lys Pro Ile Lys Arg
            100                 105

<210> SEQ ID NO: 173
<211> LENGTH: 17
<212> TYPE: PRT
<213> ORGANISM: Arabidopsis sp.

<400> SEQUENCE: 173

Ser Thr Ser Asn Pro Tyr Arg Lys Phe Lys Thr Asn Tyr Thr Lys Asp
1               5                   10                  15

Ile

<210> SEQ ID NO: 174
<211> LENGTH: 7

```
<212> TYPE: PRT
<213> ORGANISM: Arabidopsis sp.

<400> SEQUENCE: 174

Leu Ser Phe Pro Val Phe Tyr
 1               5

<210> SEQ ID NO: 175
<211> LENGTH: 39
<212> TYPE: PRT
<213> ORGANISM: Arabidopsis sp.

<400> SEQUENCE: 175

Ile Leu Ile Gly Lys Ser Asp Val His Gly Trp Gly Ala Phe Thr Trp
 1               5                  10                  15

Val Ser Asn His Val Asn Ile Arg Ile Ser Leu Ile Val Ile Gly Ala
                20                  25                  30

Phe Ile Thr Leu Phe Phe Phe
            35

<210> SEQ ID NO: 176
<211> LENGTH: 4
<212> TYPE: PRT
<213> ORGANISM: Arabidopsis sp.

<400> SEQUENCE: 176

Cys Phe Ile Leu
 1

<210> SEQ ID NO: 177
<211> LENGTH: 6
<212> TYPE: PRT
<213> ORGANISM: Arabidopsis sp.

<400> SEQUENCE: 177

Thr Ile Lys Tyr Ile Val
 1               5

<210> SEQ ID NO: 178
<211> LENGTH: 53
<212> TYPE: PRT
<213> ORGANISM: Arabidopsis sp.

<400> SEQUENCE: 178

Tyr Gly Leu Thr Arg Gln Asp Ser Leu Lys Lys Asn Glu Tyr Leu Gly
 1               5                  10                  15

Glu Tyr Thr Gly Glu Leu Ile Thr His Asp Glu Ala Asn Glu Arg Gly
                20                  25                  30

Arg Ile Glu Asp Arg Ile Gly Ser Ser Tyr Leu Phe Thr Leu Asn Asp
            35                  40                  45

Gln Val Thr Ser Glu
        50

<210> SEQ ID NO: 179
<211> LENGTH: 28
<212> TYPE: PRT
<213> ORGANISM: Arabidopsis sp.

<400> SEQUENCE: 179

Ser Asn Val Leu Ile Ile Arg Gly Leu His Ile Tyr Ser Asn Gln Ser
 1               5                  10                  15

Asn Ile Tyr Phe Thr Ala Arg Asn Arg Cys Ser Pro
```

```
                        20                  25
```

<210> SEQ ID NO: 180
<211> LENGTH: 13
<212> TYPE: PRT
<213> ORGANISM: Arabidopsis sp.

<400> SEQUENCE: 180

```
Arg Lys Arg Val Gln Ile Ser Gln Ser Leu Ser Lys Thr
 1               5                  10
```

<210> SEQ ID NO: 181
<211> LENGTH: 16
<212> TYPE: PRT
<213> ORGANISM: Arabidopsis sp.

<400> SEQUENCE: 181

```
Leu Leu Arg Gln Gly Thr Lys Pro Leu Tyr Phe Ile Leu Asn Lys Tyr
 1               5                  10                  15
```

<210> SEQ ID NO: 182
<211> LENGTH: 13
<212> TYPE: PRT
<213> ORGANISM: Arabidopsis sp.

<400> SEQUENCE: 182

```
His Tyr Thr Asn Lys Asn Thr Tyr Val Ser Phe Phe Ser
 1               5                  10
```

<210> SEQ ID NO: 183
<211> LENGTH: 24
<212> TYPE: PRT
<213> ORGANISM: Arabidopsis sp.

<400> SEQUENCE: 183

```
Ile Val Tyr Gln Leu Tyr Ser Ser Leu Ile Gly Phe His Ile Glu Asp
 1               5                  10                  15

Ile Pro Arg Asn Ser Asn Ser Phe
                20
```

<210> SEQ ID NO: 184
<211> LENGTH: 78
<212> TYPE: PRT
<213> ORGANISM: Arabidopsis sp.

<400> SEQUENCE: 184

```
Met Ile Phe Ser Cys Arg Glu Asn Leu Gly Tyr Glu Asn Leu Trp Phe
 1               5                  10                  15

Arg Val Gln Leu Met Ile Val Arg Gly Asp Gln Arg Ile Gly Leu Phe
                20                  25                  30

Ala Glu Arg Ala Ile Glu Glu Gly Glu Leu Phe Phe Asp Tyr Cys
            35                  40                  45

Tyr Gly Pro Glu His Ala Asp Trp Ser Arg Gly Arg Glu Pro Arg Lys
        50                  55                  60

Thr Gly Ala Ser Lys Arg Ser Lys Glu Ala Arg Pro Ala Arg
 65                  70                  75
```

<210> SEQ ID NO: 185
<211> LENGTH: 37
<212> TYPE: PRT
<213> ORGANISM: Arabidopsis sp.

<400> SEQUENCE: 185

-continued

Gly Glu Ala Ala Ile Gln Ala Val Leu Phe Leu Cys Tyr Gly Ile Ser
1               5                   10                  15

Ile Asn Asn Val Met Leu Phe Cys Val Thr Lys Pro Lys Leu Lys Phe
                20                  25                  30

Leu Phe Tyr Leu Phe
            35

<210> SEQ ID NO: 186
<211> LENGTH: 9
<212> TYPE: PRT
<213> ORGANISM: Arabidopsis sp.

<400> SEQUENCE: 186

Gly Val Leu Phe Val Ser Tyr Val Ser
1               5

<210> SEQ ID NO: 187
<211> LENGTH: 10
<212> TYPE: PRT
<213> ORGANISM: Arabidopsis sp.

<400> SEQUENCE: 187

Leu Ser Lys Phe Ser Phe Cys Ile Ser Ile
1               5                   10

<210> SEQ ID NO: 188
<211> LENGTH: 6
<212> TYPE: PRT
<213> ORGANISM: Arabidopsis sp.

<400> SEQUENCE: 188

Lys Gln Cys Leu Cys Cys
1               5

<210> SEQ ID NO: 189
<211> LENGTH: 29
<212> TYPE: PRT
<213> ORGANISM: Arabidopsis sp.

<400> SEQUENCE: 189

Thr Phe Gly Lys Lys Leu Cys Thr Thr Leu His Leu Phe Ser Leu
1               5                   10                  15

His Leu Ala Lys Asn His Ile Thr Gln Val Cys Gly Thr
                20                  25

<210> SEQ ID NO: 190
<211> LENGTH: 6
<212> TYPE: PRT
<213> ORGANISM: Arabidopsis sp.

<400> SEQUENCE: 190

Cys Thr Lys Met Ser Lys
1               5

<210> SEQ ID NO: 191
<211> LENGTH: 12
<212> TYPE: PRT
<213> ORGANISM: Arabidopsis sp.

<400> SEQUENCE: 191

Trp Val Leu Ser Leu Lys Lys Asn Ile Gly Tyr Glu
1               5                   10

```
<210> SEQ ID NO: 192
<211> LENGTH: 19
<212> TYPE: PRT
<213> ORGANISM: Arabidopsis sp.

<400> SEQUENCE: 192

Ser Ile Val Arg Ile Leu Gly Ile Ser Ser Phe Gly Phe Lys Thr Phe
 1               5                  10                  15

Phe Glu Ile

<210> SEQ ID NO: 193
<211> LENGTH: 24
<212> TYPE: PRT
<213> ORGANISM: Arabidopsis sp.

<400> SEQUENCE: 193

Phe Cys Ser Leu Leu Ser Asn Thr Trp Lys Asn His Gln Gln Ser Gly
 1               5                  10                  15

Cys Ser Leu Arg Lys Val Leu Leu
            20

<210> SEQ ID NO: 194
<211> LENGTH: 10
<212> TYPE: PRT
<213> ORGANISM: Arabidopsis sp.

<400> SEQUENCE: 194

Cys Lys Tyr Val Phe Asp Ala Ser Asn Ile
 1               5                  10

<210> SEQ ID NO: 195
<211> LENGTH: 4
<212> TYPE: PRT
<213> ORGANISM: Arabidopsis sp.

<400> SEQUENCE: 195

Tyr Leu Asn Lys
 1

<210> SEQ ID NO: 196
<211> LENGTH: 13
<212> TYPE: PRT
<213> ORGANISM: Arabidopsis sp.

<400> SEQUENCE: 196

Lys Gln Lys Lys Arg Lys Lys Leu Phe Lys Ile Arg Lys
 1               5                  10

<210> SEQ ID NO: 197
<211> LENGTH: 24
<212> TYPE: PRT
<213> ORGANISM: Arabidopsis sp.

<400> SEQUENCE: 197

Leu Phe Ser Lys Asn Leu Asn Tyr Lys Leu Lys Cys Leu Glu Ser Arg
 1               5                  10                  15

Thr Thr Ile Ala Lys Tyr Lys Cys
            20

<210> SEQ ID NO: 198
<211> LENGTH: 5
<212> TYPE: PRT
<213> ORGANISM: Arabidopsis sp.
```

```
<400> SEQUENCE: 198

Ile Tyr Met Lys Met
 1               5

<210> SEQ ID NO: 199
<211> LENGTH: 13
<212> TYPE: PRT
<213> ORGANISM: Arabidopsis sp.

<400> SEQUENCE: 199

Lys Thr Cys Trp Ile Cys Gly Ile Val Asn Asp His Gly
 1               5                  10

<210> SEQ ID NO: 200
<211> LENGTH: 4
<212> TYPE: PRT
<213> ORGANISM: Arabidopsis sp.

<400> SEQUENCE: 200

Met Ala Gly Ser
 1

<210> SEQ ID NO: 201
<211> LENGTH: 4
<212> TYPE: PRT
<213> ORGANISM: Arabidopsis sp.

<400> SEQUENCE: 201

Ile His Tyr Phe
 1

<210> SEQ ID NO: 202
<211> LENGTH: 48
<212> TYPE: PRT
<213> ORGANISM: Arabidopsis sp.

<400> SEQUENCE: 202

Lys Ser Asn Phe Phe Ile Ser Ile Ile Cys Phe Lys Glu Lys Lys Asn
 1               5                  10                  15

Thr Arg Arg Leu Ser Ile Cys Arg Leu Cys Ser Ser Val Asn Leu Tyr
             20                  25                  30

Phe Lys Thr Gly Gly Leu Phe Ile Thr Ile Ser Leu Asp Met Phe Leu
         35                  40                  45

<210> SEQ ID NO: 203
<211> LENGTH: 24
<212> TYPE: PRT
<213> ORGANISM: Arabidopsis sp.

<400> SEQUENCE: 203

Cys Arg Pro Lys Asn Arg Glu Ile Arg Lys Gly Thr Phe Val Val Ile
 1               5                  10                  15

Val Thr Lys Gln Lys Ser Leu Tyr
             20

<210> SEQ ID NO: 204
<211> LENGTH: 11
<212> TYPE: PRT
<213> ORGANISM: Arabidopsis sp.

<400> SEQUENCE: 204

Ile Ile Arg Lys Asp Glu Lys Ile Lys Pro Leu
```

<210> SEQ ID NO: 205
<211> LENGTH: 12
<212> TYPE: PRT
<213> ORGANISM: Arabidopsis sp.

<400> SEQUENCE: 205

Leu Asp Asp His Arg Arg Gly Cys Gln Leu Gln Ser
 1               5                  10

<210> SEQ ID NO: 206
<211> LENGTH: 34
<212> TYPE: PRT
<213> ORGANISM: Arabidopsis sp.

<400> SEQUENCE: 206

Cys Phe Tyr Ile Asp Leu Ser Tyr Ile Leu Cys Ser Phe Thr Phe Lys
 1               5                  10                  15

Lys Gln Tyr His Pro Ile Phe Phe Leu Leu Ser Val Ser Ile Phe
            20                  25                  30

Ala Asn

<210> SEQ ID NO: 207
<211> LENGTH: 21
<212> TYPE: PRT
<213> ORGANISM: Arabidopsis sp.

<400> SEQUENCE: 207

Arg Asn Thr Lys Glu His Lys Lys Gln Leu Val Pro Asp Ser Thr Ile
 1               5                  10                  15

Ser Asn Asp Leu His
            20

<210> SEQ ID NO: 208
<211> LENGTH: 106
<212> TYPE: PRT
<213> ORGANISM: Arabidopsis sp.

<400> SEQUENCE: 208

Pro Pro Pro Pro Ser Ile Phe Pro Leu Ser Phe Thr Ser Leu Ser Leu
 1               5                  10                  15

Tyr Leu Leu Asn Ser Gly His Arg Leu Arg Arg Phe Leu Cys Tyr Ser
            20                  25                  30

Pro Gly Arg Cys Arg Ser Leu Ile His Asp Leu Val Ser His His Arg
        35                  40                  45

Leu His Phe Asn Pro Gln Ser Leu Arg Lys Thr Arg Met Leu Cys Ser
    50                  55                  60

Pro Phe Pro Ser Leu His Leu Leu Asp Arg Ser Leu His Arg Pro Ser
65                  70                  75                  80

Leu Cys Leu Trp Asp Gln Lys Asn His Glu His Asp His Val Tyr Lys
                85                  90                  95

Ser Arg Gln Lys Leu Val Ser Cys Asp Thr
            100                 105

<210> SEQ ID NO: 209
<211> LENGTH: 5
<212> TYPE: PRT
<213> ORGANISM: Arabidopsis sp.

<400> SEQUENCE: 209

Lys Met Asp Val Gly
1               5

<210> SEQ ID NO: 210
<211> LENGTH: 15
<212> TYPE: PRT
<213> ORGANISM: Arabidopsis sp.

<400> SEQUENCE: 210

Gly Phe Val Leu Phe Gly Ala Thr Arg Ser Asp Ala Asp Val Val
1               5                   10                  15

<210> SEQ ID NO: 211
<211> LENGTH: 32
<212> TYPE: PRT
<213> ORGANISM: Arabidopsis sp.

<400> SEQUENCE: 211

Gln His Tyr Ile Trp Gly Leu Arg Gly Gly Glu Val Val Arg Glu Ser
1               5                   10                  15

Arg Cys Gly Ser Asp Leu Trp Tyr Asn Val Val Glu Ala Lys Arg
            20                  25                  30

<210> SEQ ID NO: 212
<211> LENGTH: 11
<212> TYPE: PRT
<213> ORGANISM: Arabidopsis sp.

<400> SEQUENCE: 212

Gly Arg Lys Ser Cys Gly Gly Gly Tyr Gly Gly
1               5                   10

<210> SEQ ID NO: 213
<211> LENGTH: 42
<212> TYPE: PRT
<213> ORGANISM: Arabidopsis sp.

<400> SEQUENCE: 213

Pro Pro His Ser Phe Gly Gly Ser Gln Phe Cys Glu Leu Val Tyr Val
1               5                   10                  15

Leu His Leu Cys Trp Asn Trp Phe Asn Glu Asp Leu Gln Arg Val Phe
            20                  25                  30

Gly Phe Cys Glu Tyr Val Asp Phe Glu His
            35                  40

<210> SEQ ID NO: 214
<211> LENGTH: 6
<212> TYPE: PRT
<213> ORGANISM: Arabidopsis sp.

<400> SEQUENCE: 214

Glu Val Glu Lys Arg Leu
1               5

<210> SEQ ID NO: 215
<211> LENGTH: 4
<212> TYPE: PRT
<213> ORGANISM: Arabidopsis sp.

<400> SEQUENCE: 215

Ile Met Cys Phe
1

<210> SEQ ID NO: 216
<211> LENGTH: 27
<212> TYPE: PRT
<213> ORGANISM: Arabidopsis sp.

<400> SEQUENCE: 216

Ser Cys Val Arg Tyr Leu Thr Tyr Thr His Leu Leu Asn Val Phe
 1               5                  10                  15

Glu Ile Phe Leu Phe Leu Phe Ser Ile Ser Cys
            20                  25

<210> SEQ ID NO: 217
<211> LENGTH: 25
<212> TYPE: PRT
<213> ORGANISM: Arabidopsis sp.

<400> SEQUENCE: 217

Glu Phe Asn Pro Tyr Ile Cys His Lys Asn Ser Arg Ile Ser Glu Ser
 1               5                  10                  15

Lys Asn Ile Leu Ser Lys Asn Asn His
            20                  25

<210> SEQ ID NO: 218
<211> LENGTH: 16
<212> TYPE: PRT
<213> ORGANISM: Arabidopsis sp.

<400> SEQUENCE: 218

Leu Tyr Phe Tyr Asn Thr Pro Phe Leu Arg Lys Thr Trp Arg Phe Asn
 1               5                  10                  15

<210> SEQ ID NO: 219
<211> LENGTH: 12
<212> TYPE: PRT
<213> ORGANISM: Arabidopsis sp.

<400> SEQUENCE: 219

Lys Ile Ser Asp Leu Arg Arg Ser Phe Lys Cys Val
 1               5                  10

<210> SEQ ID NO: 220
<211> LENGTH: 6
<212> TYPE: PRT
<213> ORGANISM: Arabidopsis sp.

<400> SEQUENCE: 220

Leu Asn Leu Arg Ile Glu
 1               5

<210> SEQ ID NO: 221
<211> LENGTH: 25
<212> TYPE: PRT
<213> ORGANISM: Arabidopsis sp.

<400> SEQUENCE: 221

Tyr Ser His Ile Tyr Ile Phe Glu Asp Leu Asn Ser Phe Cys Phe Phe
 1               5                  10                  15

His Ile Cys Ile Ile Tyr Lys Leu Lys
            20                  25

<210> SEQ ID NO: 222
<211> LENGTH: 9
<212> TYPE: PRT

<213> ORGANISM: Arabidopsis sp.

<400> SEQUENCE: 222

Ile Leu Ile Tyr Ile Met Thr Leu Ile
 1               5

<210> SEQ ID NO: 223
<211> LENGTH: 10
<212> TYPE: PRT
<213> ORGANISM: Arabidopsis sp.

<400> SEQUENCE: 223

Val Leu Pro Asp Thr Pro Lys Cys Ile Tyr
 1               5                  10

<210> SEQ ID NO: 224
<211> LENGTH: 9
<212> TYPE: PRT
<213> ORGANISM: Arabidopsis sp.

<400> SEQUENCE: 224

Ser Ile Asn Ile Phe Ser Leu Val Tyr
 1               5

<210> SEQ ID NO: 225
<211> LENGTH: 14
<212> TYPE: PRT
<213> ORGANISM: Arabidopsis sp.

<400> SEQUENCE: 225

Thr Lys Leu Ser His Lys Tyr Glu Leu Thr Pro Phe Phe Leu
 1               5                  10

<210> SEQ ID NO: 226
<211> LENGTH: 13
<212> TYPE: PRT
<213> ORGANISM: Arabidopsis sp.

<400> SEQUENCE: 226

Ala Val Lys Arg Gln Ala Asn Pro Thr Ser Thr Tyr Ile
 1               5                  10

<210> SEQ ID NO: 227
<211> LENGTH: 30
<212> TYPE: PRT
<213> ORGANISM: Arabidopsis sp.

<400> SEQUENCE: 227

Tyr Tyr Ile Leu Lys Ile Lys Ile Phe Leu Asn Phe Pro Tyr Tyr Phe
 1               5                  10                  15
Pro Phe Lys Ala Ser Lys Ser Lys Tyr Val Ser Ser Arg Leu
                20                  25                  30

<210> SEQ ID NO: 228
<211> LENGTH: 15
<212> TYPE: PRT
<213> ORGANISM: Arabidopsis sp.

<400> SEQUENCE: 228

Phe Ser Leu Ile Arg Phe Ser Thr Lys Lys Asn Gln Leu Leu Ile
 1               5                  10                  15

<210> SEQ ID NO: 229
<211> LENGTH: 39

```
<212> TYPE: PRT
<213> ORGANISM: Arabidopsis sp.

<400> SEQUENCE: 229

Lys Thr Leu Cys Ile Ile Leu Phe Thr Asn Ile Arg Glu Asp Glu Lys
 1               5                  10                  15

Lys Arg Arg Gly Glu Trp Leu Met Glu Lys Val Ser Phe Thr Pro Asn
                20                  25                  30

Ile Tyr Glu Leu Thr Arg Leu
            35

<210> SEQ ID NO: 230
<211> LENGTH: 9
<212> TYPE: PRT
<213> ORGANISM: Arabidopsis sp.

<400> SEQUENCE: 230

Asn Pro Tyr Ile Leu Ile Val Cys Leu
 1               5

<210> SEQ ID NO: 231
<211> LENGTH: 4
<212> TYPE: PRT
<213> ORGANISM: Arabidopsis sp.

<400> SEQUENCE: 231

Ile Asn Asn Ile
 1

<210> SEQ ID NO: 232
<211> LENGTH: 19
<212> TYPE: PRT
<213> ORGANISM: Arabidopsis sp.

<400> SEQUENCE: 232

Ser Ile Met Leu Phe Val Pro Cys Met Ile His Lys Thr Phe Ile Phe
 1               5                  10                  15

Glu Phe Val

<210> SEQ ID NO: 233
<211> LENGTH: 37
<212> TYPE: PRT
<213> ORGANISM: Arabidopsis sp.

<400> SEQUENCE: 233

Glu Asn His Glu Asp Asp Gly Glu Gly Leu Pro Pro Glu Leu Asn Gln
 1               5                  10                  15

Ile Lys Glu Gln Ile Glu Lys Glu Arg Phe Leu His Ile Lys Val Arg
                20                  25                  30

Asp Ile Trp Leu Leu
            35

<210> SEQ ID NO: 234
<211> LENGTH: 9
<212> TYPE: PRT
<213> ORGANISM: Arabidopsis sp.

<400> SEQUENCE: 234

Tyr Phe Ile Leu Phe Cys Met Phe Phe
 1               5

<210> SEQ ID NO: 235
```

```
<211> LENGTH: 10
<212> TYPE: PRT
<213> ORGANISM: Arabidopsis sp.

<400> SEQUENCE: 235

Lys Leu Arg Arg Gly Glu Asp Leu Ile Ser
 1               5                  10

<210> SEQ ID NO: 236
<211> LENGTH: 11
<212> TYPE: PRT
<213> ORGANISM: Arabidopsis sp.

<400> SEQUENCE: 236

Leu Tyr Asp Ser Lys Glu Met Leu Arg Tyr Ile
 1               5                  10

<210> SEQ ID NO: 237
<211> LENGTH: 4
<212> TYPE: PRT
<213> ORGANISM: Arabidopsis sp.

<400> SEQUENCE: 237

Thr Val Ile His
 1

<210> SEQ ID NO: 238
<211> LENGTH: 13
<212> TYPE: PRT
<213> ORGANISM: Arabidopsis sp.

<400> SEQUENCE: 238

Ser Leu Lys Leu Lys Arg Glu Ile Ser Lys Leu Leu Asn
 1               5                  10

<210> SEQ ID NO: 239
<211> LENGTH: 26
<212> TYPE: PRT
<213> ORGANISM: Arabidopsis sp.

<400> SEQUENCE: 239

Lys Gln Asn Leu Glu Asn Ala Ser Glu Ser Ile Thr Thr Ser Arg Ser
 1               5                  10                  15

Val Gly Tyr Pro Lys Leu Arg Ile Lys Lys
                20                  25

<210> SEQ ID NO: 240
<211> LENGTH: 4
<212> TYPE: PRT
<213> ORGANISM: Arabidopsis sp.

<400> SEQUENCE: 240

Leu Ile Tyr Leu
 1

<210> SEQ ID NO: 241
<211> LENGTH: 5
<212> TYPE: PRT
<213> ORGANISM: Arabidopsis sp.

<400> SEQUENCE: 241

Tyr Lys Ala Gly Thr
 1               5
```

-continued

<210> SEQ ID NO: 242
<211> LENGTH: 29
<212> TYPE: PRT
<213> ORGANISM: Arabidopsis sp.

<400> SEQUENCE: 242

Ile Phe Leu Phe Leu Ser Asn Lys Ile Val Ile Gln Phe Val Phe Phe
1               5                   10                  15

Ser Thr Lys Lys Leu Asn Arg Ser Lys Leu Phe Phe Phe
            20                  25

<210> SEQ ID NO: 243
<211> LENGTH: 34
<212> TYPE: PRT
<213> ORGANISM: Arabidopsis sp.

<400> SEQUENCE: 243

His Ser Ala Lys Lys Ala Lys Ile Asp Ala Tyr Ile Lys Lys Ser Lys
1               5                   10                  15

Ser Lys Leu Leu Tyr Ser Ser Ile Leu Val Ser Leu Tyr Ile Glu Ser
            20                  25                  30

Ser Phe

<210> SEQ ID NO: 244
<211> LENGTH: 18
<212> TYPE: PRT
<213> ORGANISM: Arabidopsis sp.

<400> SEQUENCE: 244

Asn Leu Lys Asn His Leu Pro Ile Tyr Tyr Leu Ile Asn Arg Glu Asn
1               5                   10                  15

Ser Ser

<210> SEQ ID NO: 245
<211> LENGTH: 17
<212> TYPE: PRT
<213> ORGANISM: Arabidopsis sp.

<400> SEQUENCE: 245

Asp Thr Phe Gln Val Trp Leu Leu Met Leu His Thr Ile Asn Arg Leu
1               5                   10                  15

Thr

<210> SEQ ID NO: 246
<211> LENGTH: 100
<212> TYPE: PRT
<213> ORGANISM: Arabidopsis sp.

<400> SEQUENCE: 246

Thr Ser Pro Leu Gln Arg Met Ile Met Glu Glu Thr Thr Asn His Phe
1               5                   10                  15

Cys Arg Glu Cys Lys Thr His Phe Val Ile Ser Val Pro His Leu Ile
            20                  25                  30

Ile Ile Leu Thr Lys Ile Lys Val Met Phe Leu Met Arg Ile Lys Ile
        35                  40                  45

Met Leu Leu Lys Lys Met Tyr His Tyr Phe Leu Met Lys Met Tyr His
    50                  55                  60

Tyr Tyr Gln Val Ser Ser Phe Gln Leu Leu Arg Ser Tyr His Asp Pro
65                  70                  75                  80

Leu His Gly Ser Ser Pro Lys Gly Met Cys Val Phe Cys Phe Val Leu

```
                    85                  90                  95
Val Ser Lys Tyr
            100

<210> SEQ ID NO: 247
<211> LENGTH: 4
<212> TYPE: PRT
<213> ORGANISM: Arabidopsis sp.

<400> SEQUENCE: 247

Ser Tyr Thr Ile
  1

<210> SEQ ID NO: 248
<211> LENGTH: 13
<212> TYPE: PRT
<213> ORGANISM: Arabidopsis sp.

<400> SEQUENCE: 248

Ser Leu Ile Val His Ile Tyr Ile Ser Leu Thr Leu Gln
  1               5                  10

<210> SEQ ID NO: 249
<211> LENGTH: 4
<212> TYPE: PRT
<213> ORGANISM: Arabidopsis sp.

<400> SEQUENCE: 249

Pro Ala Asp Gly
  1

<210> SEQ ID NO: 250
<211> LENGTH: 4
<212> TYPE: PRT
<213> ORGANISM: Arabidopsis sp.

<400> SEQUENCE: 250

Phe Cys Asp Trp
  1

<210> SEQ ID NO: 251
<211> LENGTH: 8
<212> TYPE: PRT
<213> ORGANISM: Arabidopsis sp.

<400> SEQUENCE: 251

Glu Thr Asn Leu Leu Phe Glu Trp
  1               5

<210> SEQ ID NO: 252
<211> LENGTH: 6
<212> TYPE: PRT
<213> ORGANISM: Arabidopsis sp.

<400> SEQUENCE: 252

Gly Thr Arg Ile Glu Gln
  1               5

<210> SEQ ID NO: 253
<211> LENGTH: 11
<212> TYPE: PRT
<213> ORGANISM: Arabidopsis sp.

<400> SEQUENCE: 253
```

Gly Arg Asn Gln Glu Arg Lys Met Arg Ile Phe
1               5                   10

<210> SEQ ID NO: 254
<211> LENGTH: 18
<212> TYPE: PRT
<213> ORGANISM: Arabidopsis sp.

<400> SEQUENCE: 254

Arg Cys Arg Pro Ile Tyr Met Val Ser Phe Cys Ile Thr Tyr Val Leu
1               5                   10                  15

Asp Tyr

<210> SEQ ID NO: 255
<211> LENGTH: 5
<212> TYPE: PRT
<213> ORGANISM: Arabidopsis sp.

<400> SEQUENCE: 255

Phe Val Val His Ile
1               5

<210> SEQ ID NO: 256
<211> LENGTH: 41
<212> TYPE: PRT
<213> ORGANISM: Arabidopsis sp.

<400> SEQUENCE: 256

Thr Ala Gln Glu Ile Phe Arg Thr Val Gly Gln Asp Tyr Gly Leu Asp
1               5                   10                  15

Asp Leu Val Val Arg Arg Ala Leu Ala Lys Tyr Leu Glu Val Asp Val
                20                  25                  30

Ser Asp Ile Leu Val Thr Ile Phe Glu
            35                  40

<210> SEQ ID NO: 257
<211> LENGTH: 30
<212> TYPE: PRT
<213> ORGANISM: Arabidopsis sp.

<400> SEQUENCE: 257

Lys Leu His Thr Ser Ile Asn Asn Phe Pro Ala Tyr Leu Ile Phe Val
1               5                   10                  15

Val Phe Arg Glu Lys Cys Phe Lys Phe Ser Asn Leu Met
                20                  25                  30

<210> SEQ ID NO: 258
<211> LENGTH: 51
<212> TYPE: PRT
<213> ORGANISM: Arabidopsis sp.

<400> SEQUENCE: 258

Glu Arg Tyr Asn Glu Leu Lys Leu Lys Asn Asp Gly Thr Ala Gly Glu
1               5                   10                  15

Ala Ser Asp Leu Thr Ser Lys Thr Ile Thr Thr Ala Phe Gln Asp Phe
                20                  25                  30

Ala Asp Arg Arg His Cys Arg Arg Cys Met Val Thr Leu Asn Leu Ser
            35                  40                  45

Phe Leu Ile
        50

-continued

```
<210> SEQ ID NO: 259
<211> LENGTH: 36
<212> TYPE: PRT
<213> ORGANISM: Arabidopsis sp.

<400> SEQUENCE: 259

Pro Gln Lys Arg Glu Met Ile Ile His Val Phe Ile Leu Phe Tyr His
 1               5                  10                  15

Leu Phe Tyr Arg Tyr Ser Ile Val Ile Cys Met Arg Ser Met Ser Pro
            20                  25                  30

Ser Leu Asp Pro
        35

<210> SEQ ID NO: 260
<211> LENGTH: 9
<212> TYPE: PRT
<213> ORGANISM: Arabidopsis sp.

<400> SEQUENCE: 260

Ala Leu Asn Ser Phe Lys Leu Phe Cys
 1               5

<210> SEQ ID NO: 261
<211> LENGTH: 6
<212> TYPE: PRT
<213> ORGANISM: Arabidopsis sp.

<400> SEQUENCE: 261

Phe His Asn Pro Tyr Ile
 1               5

<210> SEQ ID NO: 262
<211> LENGTH: 50
<212> TYPE: PRT
<213> ORGANISM: Arabidopsis sp.

<400> SEQUENCE: 262

Val Ile Asn Leu Ile Arg Leu Leu Trp Leu Val Arg Ala Lys Thr Asn
 1               5                  10                  15

Leu Val Cys Leu Arg Met Lys Ile Asp Asn His Ala Val Ser Ile Val
            20                  25                  30

Thr Ser Arg Ser Leu Ser Leu Ser Leu Ser Leu Ser Ile Phe Leu Ser
        35                  40                  45

Ile Pro
    50

<210> SEQ ID NO: 263
<211> LENGTH: 12
<212> TYPE: PRT
<213> ORGANISM: Arabidopsis sp.

<400> SEQUENCE: 263

Leu Arg Leu Leu Val Thr Gly Leu Ile Leu Asn Arg
 1               5                  10

<210> SEQ ID NO: 264
<211> LENGTH: 5
<212> TYPE: PRT
<213> ORGANISM: Arabidopsis sp.

<400> SEQUENCE: 264

Gln Lys Leu Ile Met
 1               5
```

<210> SEQ ID NO: 265
<211> LENGTH: 23
<212> TYPE: PRT
<213> ORGANISM: Arabidopsis sp.

<400> SEQUENCE: 265

Trp Ile Met Ile Thr Leu Tyr Gln Thr Arg Leu Trp Ser Gln Ile Gln
 1               5                  10                  15

Thr Thr Leu Cys Gly Arg Leu
            20

<210> SEQ ID NO: 266
<211> LENGTH: 5
<212> TYPE: PRT
<213> ORGANISM: Arabidopsis sp.

<400> SEQUENCE: 266

Arg Arg Ile Phe Thr
 1               5

<210> SEQ ID NO: 267
<211> LENGTH: 19
<212> TYPE: PRT
<213> ORGANISM: Arabidopsis sp.

<400> SEQUENCE: 267

Lys Glu Leu Arg Tyr Leu Gly Glu Thr Gly Lys Lys Ile Lys Ile Asp
 1               5                  10                  15

Leu Met His

<210> SEQ ID NO: 268
<211> LENGTH: 8
<212> TYPE: PRT
<213> ORGANISM: Arabidopsis sp.

<400> SEQUENCE: 268

Tyr Ile Tyr Leu His Cys Ile Pro
 1               5

<210> SEQ ID NO: 269
<211> LENGTH: 10
<212> TYPE: PRT
<213> ORGANISM: Arabidopsis sp.

<400> SEQUENCE: 269

Leu Cys Trp Phe Ala Val Val Met Leu His
 1               5                  10

<210> SEQ ID NO: 270
<211> LENGTH: 9
<212> TYPE: PRT
<213> ORGANISM: Arabidopsis sp.

<400> SEQUENCE: 270

Thr Tyr Phe Gly Gly Leu Arg Arg Ala
 1               5

<210> SEQ ID NO: 271
<211> LENGTH: 15
<212> TYPE: PRT
<213> ORGANISM: Arabidopsis sp.

<400> SEQUENCE: 271

```
Arg Phe Thr Ile Thr Cys Ala Asn Lys Ile Asn Val Leu Cys His
  1               5                  10                  15
```

<210> SEQ ID NO: 272
<211> LENGTH: 28
<212> TYPE: PRT
<213> ORGANISM: Arabidopsis sp.

<400> SEQUENCE: 272

```
Thr Leu Thr Lys Leu His Lys Asp Thr Ile Arg Tyr Thr Asn Leu Cys
  1               5                  10                  15

Arg Asn Tyr Ser His Asp Met Tyr Val Lys Asn Thr
             20                  25
```

<210> SEQ ID NO: 273
<211> LENGTH: 95
<212> TYPE: PRT
<213> ORGANISM: Arabidopsis sp.

<400> SEQUENCE: 273

```
Ser Phe Leu Tyr Val Leu Met Val Leu Ser Gln Val Thr Lys Lys Val
  1               5                  10                  15

Ser Arg Lys Ser Ser Arg Ser Val Arg Lys Lys Ser Arg Leu Arg Lys
             20                  25                  30

Tyr Ala Arg Tyr Pro Pro Ala Leu Lys Lys Thr Thr Ser Gly Glu Ala
         35                  40                  45

Lys Phe Tyr Lys His Tyr Thr Pro Cys Thr Cys Lys Ser Lys Cys Gly
     50                  55                  60

Gln Gln Cys Pro Cys Leu Thr His Glu Asn Cys Cys Glu Lys Tyr Cys
 65                  70                  75                  80

Gly Tyr Val Ile Gln Phe Phe Leu Ser Arg Lys Ile His Glu Ile
                 85                  90                  95
```

<210> SEQ ID NO: 274
<211> LENGTH: 22
<212> TYPE: PRT
<213> ORGANISM: Arabidopsis sp.

<400> SEQUENCE: 274

```
Phe Glu His Glu Phe Val Phe Val Gln Val Leu Lys Gly Leu Gln
  1               5                  10                  15

Gln Ser Leu Trp Arg Met
             20
```

<210> SEQ ID NO: 275
<211> LENGTH: 16
<212> TYPE: PRT
<213> ORGANISM: Arabidopsis sp.

<400> SEQUENCE: 275

```
Leu Cys Asn Trp Pro Met His Lys Ser Thr Met Ser Leu Phe Cys Cys
  1               5                  10                  15
```

<210> SEQ ID NO: 276
<211> LENGTH: 11
<212> TYPE: PRT
<213> ORGANISM: Arabidopsis sp.

<400> SEQUENCE: 276

```
Met Arg Ser Arg Ser Leu Ser Glu Leu Ser Ser
  1               5                  10
```

```
<210> SEQ ID NO: 277
<211> LENGTH: 13
<212> TYPE: PRT
<213> ORGANISM: Arabidopsis sp.

<400> SEQUENCE: 277

Val Thr Leu Ser Leu Gln Tyr Leu Phe Ile Gln Ile Leu
  1               5                  10

<210> SEQ ID NO: 278
<211> LENGTH: 6
<212> TYPE: PRT
<213> ORGANISM: Arabidopsis sp.

<400> SEQUENCE: 278

Phe Lys Pro Lys Val Leu
  1               5

<210> SEQ ID NO: 279
<211> LENGTH: 5
<212> TYPE: PRT
<213> ORGANISM: Arabidopsis sp.

<400> SEQUENCE: 279

Lys Lys Leu Tyr Ile
  1               5

<210> SEQ ID NO: 280
<211> LENGTH: 7
<212> TYPE: PRT
<213> ORGANISM: Arabidopsis sp.

<400> SEQUENCE: 280

Leu Trp Arg Trp His Ser Trp
  1               5

<210> SEQ ID NO: 281
<211> LENGTH: 17
<212> TYPE: PRT
<213> ORGANISM: Arabidopsis sp.

<400> SEQUENCE: 281

Asp Thr Ser Ala Asn Pro Met Gln Glu His Ala Ile Pro Pro Ser Asn
  1               5                  10                  15

Gln

<210> SEQ ID NO: 282
<211> LENGTH: 45
<212> TYPE: PRT
<213> ORGANISM: Arabidopsis sp.

<400> SEQUENCE: 282

Lys Gly Asn Gln Arg Gln Ile Arg Thr Glu Asn Leu Lys Leu Ile Ile
  1               5                  10                  15

Arg Lys Thr Phe Asn Tyr His Phe Pro Tyr Phe Thr Arg Phe Ser Leu
                 20                  25                  30

Glu Ser Leu Met Phe Met Asp Gly Val His Leu His Gly
             35                  40                  45

<210> SEQ ID NO: 283
<211> LENGTH: 5
<212> TYPE: PRT
```

<213> ORGANISM: Arabidopsis sp.

<400> SEQUENCE: 283

Leu Leu Val His Ser
 1               5

<210> SEQ ID NO: 284
<211> LENGTH: 21
<212> TYPE: PRT
<213> ORGANISM: Arabidopsis sp.

<400> SEQUENCE: 284

His Phe Phe Phe Phe Asn Asn Val Leu Tyr Phe Arg Pro Leu Asn Ile
 1               5                  10                  15

Leu Cys Asp Met Val
            20

<210> SEQ ID NO: 285
<211> LENGTH: 18
<212> TYPE: PRT
<213> ORGANISM: Arabidopsis sp.

<400> SEQUENCE: 285

Pro Val Arg Thr Leu Leu Lys Arg Met Ser Ile Ser Glu Asn Ile Leu
 1               5                  10                  15

Glu Asn

<210> SEQ ID NO: 286
<211> LENGTH: 11
<212> TYPE: PRT
<213> ORGANISM: Arabidopsis sp.

<400> SEQUENCE: 286

Ser Leu Met Met Lys Leu Met Ser Val Gly Glu
 1               5                  10

<210> SEQ ID NO: 287
<211> LENGTH: 11
<212> TYPE: PRT
<213> ORGANISM: Arabidopsis sp.

<400> SEQUENCE: 287

Lys Ile Gly Leu Val Leu Pro Thr Ser Leu Pro
 1               5                  10

<210> SEQ ID NO: 288
<211> LENGTH: 9
<212> TYPE: PRT
<213> ORGANISM: Arabidopsis sp.

<400> SEQUENCE: 288

Leu Gln Asn Asn Phe Glu Val Thr Phe
 1               5

<210> SEQ ID NO: 289
<211> LENGTH: 51
<212> TYPE: PRT
<213> ORGANISM: Arabidopsis sp.

<400> SEQUENCE: 289

Ser Phe Ala Gly Tyr Thr Ser Ile Arg Ile Lys Val Thr Phe Ile Leu
 1               5                  10                  15

Gln Leu Glu Ile Asp Ala Arg Arg Lys Gly Asn Glu Phe Lys Phe Leu

```
                     20                  25                  30

Asn His Ser Ala Arg Pro Asn Cys Tyr Ala Lys Val Leu Ser Arg Tyr
         35                  40                  45

Thr Leu Ser
     50

<210> SEQ ID NO: 290
<211> LENGTH: 26
<212> TYPE: PRT
<213> ORGANISM: Arabidopsis sp.

<400> SEQUENCE: 290

Thr Asn Thr Asn Ile Ile Gln Thr Lys Ile Leu Met Leu Val Ser Leu
 1               5                  10                  15

Val Lys Ser Cys Ile Asn Phe Thr Arg Arg
             20                  25

<210> SEQ ID NO: 291
<211> LENGTH: 16
<212> TYPE: PRT
<213> ORGANISM: Arabidopsis sp.

<400> SEQUENCE: 291

Leu Val Phe Ile Leu Lys Ile Phe Gln Glu Thr Gln Thr His Phe Lys
 1               5                  10                  15

<210> SEQ ID NO: 292
<211> LENGTH: 7
<212> TYPE: PRT
<213> ORGANISM: Arabidopsis sp.

<400> SEQUENCE: 292

Phe Phe Leu Val Glu Lys Ile
 1               5

<210> SEQ ID NO: 293
<211> LENGTH: 10
<212> TYPE: PRT
<213> ORGANISM: Arabidopsis sp.

<400> SEQUENCE: 293

Val Thr Lys Ile Tyr Gly Phe Val Cys Ser
 1               5                  10

<210> SEQ ID NO: 294
<211> LENGTH: 57
<212> TYPE: PRT
<213> ORGANISM: Arabidopsis sp.

<400> SEQUENCE: 294

Glu Glu Ile Arg Gly Leu Val Tyr Leu Arg Arg Glu Gln Ser Lys Lys
 1               5                  10                  15

Val Arg Ser Phe Ser Ser Thr Thr Ala Met Asp Gln Asn Met Arg Ile
             20                  25                  30

Gly Arg Val Val Glu Asn Leu Glu Arg Leu Val Leu Leu Lys Gly Leu
         35                  40                  45

Arg Lys Pro Val Gln Leu Val Ser Phe
     50                  55

<210> SEQ ID NO: 295
<211> LENGTH: 21
<212> TYPE: PRT
```

<213> ORGANISM: Arabidopsis sp.

<400> SEQUENCE: 295

Ser Glu Glu Lys Gln Gln Phe Lys Gln Ser Phe Phe Tyr Val Met Val
1               5                   10                  15

Tyr Gln Leu Ile Met
            20

<210> SEQ ID NO: 296
<211> LENGTH: 66
<212> TYPE: PRT
<213> ORGANISM: Arabidopsis sp.

<400> SEQUENCE: 296

Cys Tyr Phe Val Leu Leu Asn Gln Asn Leu Ser Phe Cys Phe Ile Cys
1               5                   10                  15

Phe Arg Val Phe Cys Leu Tyr His Met Cys Leu Asn Phe Gln Ser Phe
            20                  25                  30

Leu Phe Val Phe Gln Phe Lys Asn Asn Val Tyr Val Val Ser Leu His
        35                  40                  45

Arg Pro Leu Glu Lys Lys Ser Phe Ala Gln Leu Tyr Ile Tyr Leu Val
    50                  55                  60

Phe Ile
65

<210> SEQ ID NO: 297
<211> LENGTH: 4
<212> TYPE: PRT
<213> ORGANISM: Arabidopsis sp.

<400> SEQUENCE: 297

Arg Lys Ile Thr
1

<210> SEQ ID NO: 298
<211> LENGTH: 18
<212> TYPE: PRT
<213> ORGANISM: Arabidopsis sp.

<400> SEQUENCE: 298

His Lys Ser Val Val Arg Asn Val Gln Lys Cys Gln Asn Asn Gly Phe
1               5                   10                  15

Tyr His

<210> SEQ ID NO: 299
<211> LENGTH: 9
<212> TYPE: PRT
<213> ORGANISM: Arabidopsis sp.

<400> SEQUENCE: 299

Lys Lys Ile Leu Val Met Asn Glu Val
1               5

<210> SEQ ID NO: 300
<211> LENGTH: 18
<212> TYPE: PRT
<213> ORGANISM: Arabidopsis sp.

<400> SEQUENCE: 300

Val Leu Ala Arg Leu Val Leu Lys Arg Phe Ser Arg Phe Asn Phe Val
1               5                   10                  15

-continued

Val Tyr

<210> SEQ ID NO: 301
<211> LENGTH: 32
<212> TYPE: PRT
<213> ORGANISM: Arabidopsis sp.

<400> SEQUENCE: 301

Val Ile His Gly Arg Ile Ile Asn Lys Val Ala Val Ala Tyr Glu Arg
 1               5                  10                  15

Phe Tyr Phe Asn Val Asn Met Tyr Leu Met His Leu Thr Phe Ser Ile
            20                  25                  30

<210> SEQ ID NO: 302
<211> LENGTH: 22
<212> TYPE: PRT
<213> ORGANISM: Arabidopsis sp.

<400> SEQUENCE: 302

Thr Asn Lys Asn Lys Lys Lys Glu Lys Ser Ser Leu Lys Ser Glu Ser
 1               5                  10                  15

Asn Tyr Phe Gln Lys Ile
            20

<210> SEQ ID NO: 303
<211> LENGTH: 21
<212> TYPE: PRT
<213> ORGANISM: Arabidopsis sp.

<400> SEQUENCE: 303

Ile Ile Asn Leu Asn Val Trp Asn Arg Glu Arg Leu Leu Leu Asn Ile
 1               5                  10                  15

Asn Ala Lys Tyr Thr
            20

<210> SEQ ID NO: 304
<211> LENGTH: 20
<212> TYPE: PRT
<213> ORGANISM: Arabidopsis sp.

<400> SEQUENCE: 304

Arg Cys Glu Lys His Val Gly Phe Val Glu Ser Leu Met Thr Thr Val
 1               5                  10                  15

Lys Trp Arg Asp
            20

<210> SEQ ID NO: 305
<211> LENGTH: 23
<212> TYPE: DNA
<213> ORGANISM: Artificial Sequence
<220> FEATURE:
<223> OTHER INFORMATION: Description of Artificial Sequence:primer Nir
      Cla-73

<400> SEQUENCE: 305
ggcggacatc aaacctactt agc                                          23

<210> SEQ ID NO: 306
<211> LENGTH: 24
<212> TYPE: DNA
<213> ORGANISM: Artificial Sequence
<220> FEATURE:
<223> OTHER INFORMATION: Description of Artificial Sequence:primer
      cer1n2

```
<400> SEQUENCE: 306 gtaacatta aggcctttcc tttt                                         24

<210> SEQ ID NO: 307
<211> LENGTH: 23
<212> TYPE: DNA
<213> ORGANISM: Artificial Sequence
<220> FEATURE:
<223> OTHER INFORMATION: Description of Artificial Sequence:primer
      Nir-C-2-S-N

<400> SEQUENCE: 307
cggtcatcaa gtgagttatg aag                                         23

<210> SEQ ID NO: 308
<211> LENGTH: 19
<212> TYPE: DNA
<213> ORGANISM: Artificial Sequence
<220> FEATURE:
<223> OTHER INFORMATION: Description of Artificial Sequence:primer
      cer1s659

<400> SEQUENCE: 308
ggtccaatcg gcaatgagt                                              19

<210> SEQ ID NO: 309
<211> LENGTH: 22
<212> TYPE: DNA
<213> ORGANISM: Artificial Sequence
<220> FEATURE:
<223> OTHER INFORMATION: Description of Artificial Sequence:primer
      cer1ns10596n

<400> SEQUENCE: 309
gtccaatcgg caatgagtag ag                                          22

<210> SEQ ID NO: 310
<211> LENGTH: 22
<212> TYPE: DNA
<213> ORGANISM: Artificial Sequence
<220> FEATURE:
<223> OTHER INFORMATION: Description of Artificial Sequence:primer Nir
      La-4Cla-S-S

<400> SEQUENCE: 310
gtgtgcctaa cagtttccgc ac                                          22

<210> SEQ ID NO: 311
<211> LENGTH: 24
<212> TYPE: DNA
<213> ORGANISM: Artificial Sequence
<220> FEATURE:
<223> OTHER INFORMATION: Description of Artificial Sequence:primer
      cer1ns10265n

<400> SEQUENCE: 311
tctcggagat ggtgccatat cagc                                        24

<210> SEQ ID NO: 312
<211> LENGTH: 40
<212> TYPE: DNA
<213> ORGANISM: Artificial Sequence
<220> FEATURE:
<223> OTHER INFORMATION: Description of Artificial Sequence:primer
      fie3cds5'.seq

<400> SEQUENCE: 312
```

```
atgtcctctg gagagcagaa ggaagagtcg tttttacacgg                              40
```

<210> SEQ ID NO: 313
<211> LENGTH: 24
<212> TYPE: DNA
<213> ORGANISM: Artificial Sequence
<220> FEATURE:
<223> OTHER INFORMATION: Description of Artificial Sequence:primer
      cer1ns10129n

<400> SEQUENCE: 313

```
tctggagagc agaaggaaga gtcg                                               24
```

<210> SEQ ID NO: 314
<211> LENGTH: 22
<212> TYPE: DNA
<213> ORGANISM: Artificial Sequence
<220> FEATURE:
<223> OTHER INFORMATION: Description of Artificial Sequence:primer
      cer1ns10030n

<400> SEQUENCE: 314

```
cgagtcattg acgtcaacag tg                                                 22
```

<210> SEQ ID NO: 315
<211> LENGTH: 24
<212> TYPE: DNA
<213> ORGANISM: Artificial Sequence
<220> FEATURE:
<223> OTHER INFORMATION: Description of Artificial Sequence:primer
      cer1ns9922n

<400> SEQUENCE: 315

```
ctcgcaaatg tgcagagtct tgtg                                               24
```

<210> SEQ ID NO: 316
<211> LENGTH: 20
<212> TYPE: DNA
<213> ORGANISM: Artificial Sequence
<220> FEATURE:
<223> OTHER INFORMATION: Description of Artificial Sequence:primer
      cer1n1570

<400> SEQUENCE: 316

```
aggtcatcgc tatgaagttc                                                    20
```

<210> SEQ ID NO: 317
<211> LENGTH: 20
<212> TYPE: DNA
<213> ORGANISM: Artificial Sequence
<220> FEATURE:
<223> OTHER INFORMATION: Description of Artificial Sequence:primer
      cer1ns98f9511n

<400> SEQUENCE: 317

```
gctagttgtg gtatggacac                                                    20
```

<210> SEQ ID NO: 318
<211> LENGTH: 21
<212> TYPE: DNA
<213> ORGANISM: Artificial Sequence
<220> FEATURE:
<223> OTHER INFORMATION: Description of Artificial Sequence:primer
      cer1ns98f9311s

<400> SEQUENCE: 318
cacatggact gatgatccat c                                              21

<210> SEQ ID NO: 319
<211> LENGTH: 20
<212> TYPE: DNA
<213> ORGANISM: Artificial Sequence
<220> FEATURE:
<223> OTHER INFORMATION: Description of Artificial Sequence:primer
      cer1s2099

<400> SEQUENCE: 319
gtaaccgttg gtttggtgat                                                20

<210> SEQ ID NO: 320
<211> LENGTH: 25
<212> TYPE: DNA
<213> ORGANISM: Artificial Sequence
<220> FEATURE:
<223> OTHER INFORMATION: Description of Artificial Sequence:primer Nir
      E-4-N-N

<400> SEQUENCE: 320
ggttagtaag tcaatgatgg ttaag                                          25

<210> SEQ ID NO: 321
<211> LENGTH: 19
<212> TYPE: DNA
<213> ORGANISM: Artificial Sequence
<220> FEATURE:
<223> OTHER INFORMATION: Description of Artificial Sequence:primer
      cer1ns8795n

<400> SEQUENCE: 321
gcgataggta atcagagag                                                 19

<210> SEQ ID NO: 322
<211> LENGTH: 20
<212> TYPE: DNA
<213> ORGANISM: Artificial Sequence
<220> FEATURE:
<223> OTHER INFORMATION: Description of Artificial Sequence:primer
      cer1ns8517n

<400> SEQUENCE: 322
ctgtaatcag gcaaacagcc                                                20

<210> SEQ ID NO: 323
<211> LENGTH: 20
<212> TYPE: DNA
<213> ORGANISM: Artificial Sequence
<220> FEATURE:
<223> OTHER INFORMATION: Description of Artificial Sequence:primer
      cer1ns98f8483s -continued

```
<400> SEQUENCE: 323
cagccatgtc tgtcgatgga                                                    20

<210> SEQ ID NO: 324
<211> LENGTH: 40
<212> TYPE: DNA
<213> ORGANISM: Artificial Sequence
<220> FEATURE:
<223> OTHER INFORMATION: Description of Artificial Sequence:primer
      fie3cds3'.seq

<400> SEQUENCE: 324
atccatcttc tctctcacca atgcagtgaa aatttcttaa                              40
```

NUCLEIC ACIDS THAT CONTROL ENDOSPERM DEVELOPMENT IN PLANTS

CROSS REFERENCE TO RELATED APPLICATIONS

This is a continuation-in-part of U.S. Ser. No. 09/071,838 (pending), filed May 1, 1998, which is incorporated herein by reference.

This invention was made with Government support under Award No. 95-37304-2329, awarded by the United States Department of Agriculture and Award Nos. 97-34339-4954 and Award No. 96-00242/1, awarded by the United States-Israel Binational Agricultural Research and Development Fund. The Government has certain rights in this invention.

FIELD OF THE INVENTION

The present invention is directed to plant genetic engineering. In particular, it relates to modulation of expression of genes controlling endosperm development in plants.

BACKGROUND OF THE INVENTION

A fundamental problem in biology is to understand how fertilization initiates reproductive development. In higher plants, the ovule generates the female gametophyte which is composed of egg, central, synergid and antipodal cells (Reiser, et al., *Plant Cell,* 1291–1301 (1993)). All are haploid except the central cell which contains two daughter nuclei that fuse prior to fertilization. One sperm nucleus fertilizes the egg to form the zygote, whereas another sperm nucleus fuses with the diploid central cell nucleus to form the triploid endosperm nucleus (van Went, et al., *Embryology of Angiosperms,* pp. 273–318 (1984)). The two fertilization products undergo distinct patterns of development. In Arabidopsis, the embryo passes through a series of stages that have been defined morphologically as preglobular, globular, heart, cotyledon and maturation (Goldberg, R. B., et al., *Science* (1994) 266: 605–614; Mansfield, S. G., et al., *Arabidopsis: An Atlas of Morphology and Development,* pp. 367–383 (1994)). The primary endosperm nucleus undergoes a series of mitotic divisions to produce nuclei that migrate into the expanding central cell (Mansfield, S. G., et al., *Arab Inf Serv* 27: 53–64 (1990); Webb, M. C., et al., *Planta* 184: 187–195 (1991)). Cytokinesis sequesters endosperm cytoplasm and nuclei into discrete cells (Mansfield, S. G., et al., *Arab Inf Serv* 27: 65–72 (1990)) that produce storage proteins, starch, and lipids which support embryo growth (Lopes, M. A. et al., *Plant Cell* 5: 1383–1399 (1993)). Fertilization also activates development of the integument cell layers of the ovule that become the seed coat, and induces the ovary to grow and form the fruit, or silique, in Arabidopsis.

Control of the expression of genes that control egg and central cell differentiation, or those that activate reproductive development in response to fertilization is useful in the production of plants with a range of desired traits. These and other advantages are provided by the present application.

SUMMARY OF THE INVENTION

The present invention provides methods of modulating fruit and seed development and other traits in plants. The methods involve providing a plant comprising a recombinant expression cassette containing an FIE nucleic acid linked to a plant promoter.

In some embodiments, transcription of the FIE nucleic acid inhibits expression of an endogenous FIE gene or activity the encoded protein. This embodiment is particularly useful, for instance, making embryo-less seed and parthenocarpic fruit. Alternatively, expression of the FIE nucleic acid may enhance expression of an endogenous FIE gene or FIE activity In the expression cassettes, the plant promoter may be a constitutive promoter, for example, the CaMV 35S promoter. Alternatively, the promoter may be a tissue-specific promoter. Examples of tissue specific expression useful in the invention include ovule-specific or embryo-specific expression. For instance, the promoter sequence from the FIE genes disclosed here can be used to direct expression in relevant plant tissues.

The invention also provides seed or fruit produced by the methods described above. The seed or fruit of the invention comprise a recombinant expression cassette containing an FIE nucleic acid.

Definitions

The phrase "nucleic acid sequence" refers to a single or double-stranded polymer of deoxyribonucleotide or ribonucleotide bases read from the 5' to the 3' end. It includes chromosomal DNA, self-replicating plasmids, infectious polymers of DNA or RNA and DNA or RNA that performs a primarily structural role.

A "promoter" is defined as an array of nucleic acid control sequences that direct transcription of an operably linked nucleic acid. As used herein, a "plant promoter" is a promoter that functions in plants. Promoters include necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter. or array of transcription factor binding sites) and a second nucleic acid sequence, wherein the expression control sequence directs transcription of the nucleic acid corresponding to the second sequence.

The term "plant" includes whole plants, plant organs (e.g., leaves, stems, flowers, roots, etc.), seeds and plant cells and progeny of same. The class of plants which can be used in the method of the invention is generally as broad as the class of higher plants amenable to transformation techniques, including angiosperms (monocotyledonous and dicotyledonous plants), as well as gymnosperms. It includes plants of a variety of ploidy levels, including polyploid, diploid, haploid and hemizygous.

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is different from any naturally occurring allelic variants.

A polynucleotide "exogenous to" an individual plant is a polynucleotide which is introduced into the plant by any means other than by a sexual cross. Examples of means by which this can be accomplished are described below, and include Agrobacterium-mediated transformation, biolistic methods, electroporation, and the like. Such a plant containing the exogenous nucleic acid is referred to here as an R₁ generation transgenic plant. Transgenic plants which arise from sexual cross or by selfing are descendants of such a plant.

A "FIE nucleic acid" or "FIE polynucleotide sequence" of the invention is a subsequence or full length polynucleotide sequence of a gene which encodes a polypeptide involved in control of reproductive development and which, when mutated, allows for aspects of fertilization independent reproductive development. In some embodiments, the polypeptides of the invention have substantial sequence identity (as defined below) to a polycomb group gene of Drosophila. An exemplary nucleic acid of the invention is the Arabidopsis FIE1 and FIE3 sequences disclosed below. FIE polynucleotides are defined by their ability to hybridize under defined conditions to the exemplified nucleic acids or PCR products derived from them. An FIE polynucleotide is typically at least about 30–40 nucleotides to about 3000, usually less than about 5000 nucleotides in length. The nucleic acids contain coding sequence of from about 100 to about 2000 nucleotides, often from about 500 to about 1700 nucleotides in length.

FIE nucleic acids are a new class of plant regulatory genes that encode polypeptides with sequence identity to members of the polycomb group genes first identified in Drosophila. Polycomb group gene products and their homologues in other species are responsible for repression of homeotic genes. The proteins are a heterogenous group that interact with each other to form large complexes that bind DNA and thereby control gene expression. For a review of the current understanding of polycomb complex genes see, Pirrotta *Cur. Op. Genet. Dev.* 7:249–258 (1997). Nine groups of polycomb genes have been identified. FIE1 (SEQ ID NO:1) is related to the group of polycomb genes encoding protein comprising a SET domain (see, e.g., Jenuwein et al. *Cell. Mol. Life Sci.* 54:80–93 (1998). FIE3 (SEQ ID NO:3) is related to the group encoding proteins comprising WD40 repeats (see, Gutjahr et al. *EMBO J.* 14:4296–4306 (1995).

In the case of both expression of transgenes and inhibition of endogenous genes (e.g., by antisense, or sense suppression) one of skill will recognize that the inserted polynucleotide sequence need not be identical, but may be only "substantially identical" to a sequence of the gene from which it was derived. As explained below, these substantially identical variants are specifically covered by the term FIE nucleic acid.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the terms "FIE nucleic acid". In addition, the term specifically includes those sequences substantially identical (determined as described below) with an FIE polynucleotide sequence disclosed here and that encode polypeptides that are either mutants of wild type FIE polypeptides or retain the function of the FIE polypeptide (e.g., resulting from conservative substitutions of amino acids in the FIE polypeptide). In addition, variants can be those that encode dominant negative mutants as described below.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11–17 (1988) e.g., as implemented in the program PC/GENE (Intelligenetics, Mountain View, Calif., USA).

The phrase "substantially identical," in the context of two nucleic acids or polypeptides, refers to sequences or subsequences that have at least 60%, preferably 80%, most preferably 90–95% nucleotide or amino acid residue identity when aligned for maximum correspondence over a comparison window as measured using one of the following sequence comparison algorithms or by manual alignment and visual inspection. This definition also refers to the complement of a test sequence, which has substantial sequence or subsequence complementarity when the test sequence has substantial identity to a reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l, Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W). (see, e.g., Creighton, *Proteins* (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes,* "Overview of principles of hybridization and the strategy of nucleic acid assays" (1993). Generally, highly stringent conditions are selected to be about 5–10° C. lower than the thermal melting point ($T_m$) for the specific sequence at a defined ionic strength pH. Low stringency conditions are generally selected to be about 15–30° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0M sodium ion, typically about 0.01 to 1.0M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 time background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cased, the nucleic acids typically hybridize under moderately stringent hybridization conditions.

In the present invention, genomic DNA or cDNA comprising FIE nucleic acids of the invention can be identified in standard Southern blots under stringent conditions using the nucleic acid sequences disclosed here. For the purposes of this disclosure, suitable stringent conditions for such hybridizations are those which include a hybridization in a buffer of 40% formamide, 1M NaCl, 1% SDS at 37° C., and at least one wash in 0.2X SSC at a temperature of at least about 50° C., usually about 55 ° C. to about 60° C., for 20 minutes, or equivalent conditions. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., a northern or Southern blot.

BRIEF DESCRIPTION OF THE DRAWINGS

FIGS. 1A and 1B show the genetic map used to clone the FIE3 gene.

DESCRIPTION OF THE PREFERRED EMBODIMENTS

Figure 2:
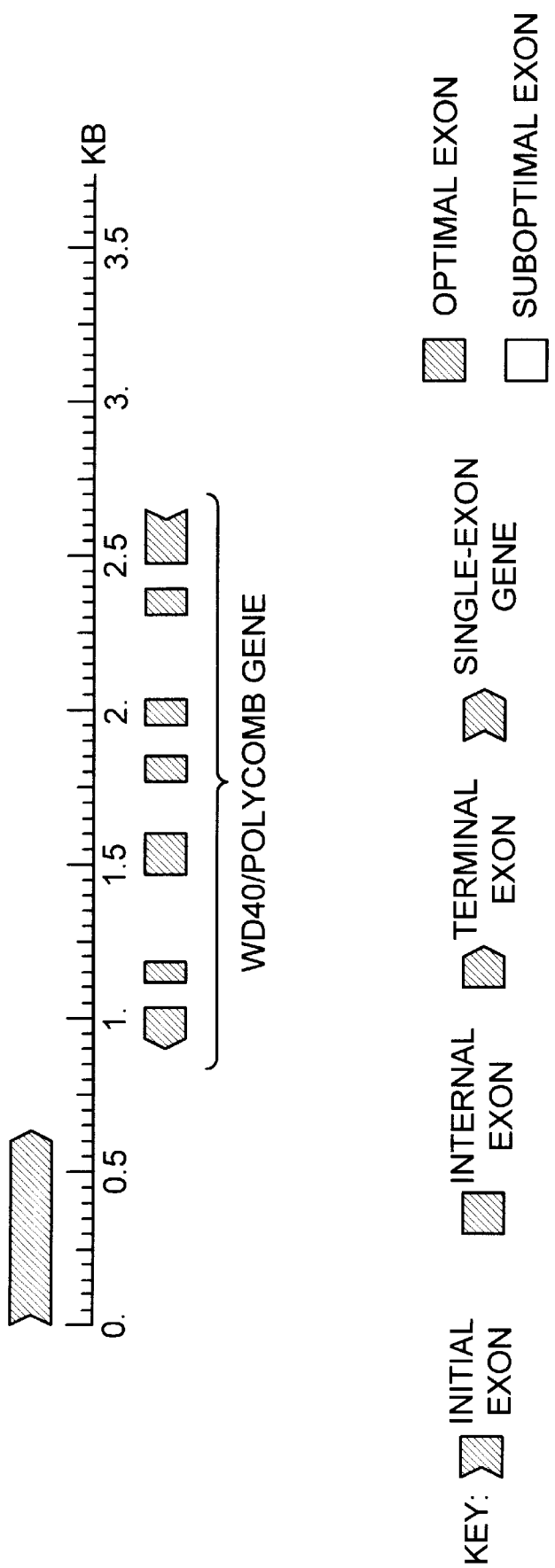
FIG. 2 shows the analysis of the sequence in the DNA shown in FIG. 1 using the GENSCANW program.

This invention provides molecular strategies for controlling seed and fruit development.

Reproduction in higher plants is unique because it is initiated by two fertilization events in the haploid female gametophyte. One sperm nucleus fertilizes the egg to form the embryo. A second sperm nucleus fertilizes the central cell to form the endosperm, a unique tissue that supports the growth of the embryo. Fertilization also activates maternal tissue differentiation, the ovule integuments form the seed coat and the ovary forms the fruit.

The present invention is based, at least in part, on the discovery of a set of female-gametophytic mutations, termed fie (fertilization-independent endosperm), and the subsequent cloning of the genes involved. Three mutants are disclosed here fie1, fie2, and fie3, which have been mapped to chromosomes 1, 2, and 3 of Arabidopsis, respectively. The fie mutations affect the central cell, allowing for replication of the central cell nucleus and endosperm development without fertilization. FIE/fie seed coat and fruit undergo fertilization-independent differentiation, showing that the fie female gametophyte is the source of signals that activates sporophytic fruit and seed coat development. Generally, the mutant fie alleles are not transmitted by the female gametophyte. Inheritance of a mutant fie allele (e.g., fie3) by the female gametophyte usually results in embryo abortion, even when the pollen bears the wild-type FIE allele. In the case of fie1 and fie2, however, transmission of the trait occurs in about 1% of the progeny from the female gametophyte. In contrast, the fie1, fie2, and fie3 mutant alleles are passed through the male gametophyte (i.e., pollen) in normal fashion.

The isolated sequences prepared as described herein, can be used in a number of techniques, for example, to suppress or enhance endogenous FIE gene expression. Modulation of FIE gene expression or FIE activity in plants is particularly useful, for example, in producing embryo-less seed, parthenocarpic fruit, or as part of a system to generate apomictic seed.

Isolation of FIE Nucleic Acids

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual,* Cold Spring Harbor Laboratory, Cold Spring Harbor, N.Y., (1989).

The isolation of FIE nucleic acids may be accomplished by a number of techniques. For instance, oligonucleotide probes based on the sequences disclosed here can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as ovules, and a cDNA library which contains the FIE gene transcript is prepared from the mRNA. Alternatively, cDNA may be prepared from mRNA extracted from other tissues in which FIE genes or homologs are expressed.

The cDNA or genomic library can then be screened using a probe based upon the sequence of a cloned FIE gene disclosed here. Probes may be used to hybridize with genomic DNA or cDNA sequences to isolate homologous genes in the same or different plant species. Alternatively, antibodies raised against an FIE polypeptide can be used to screen an mRNA expression library.

Alternatively, the nucleic acids of interest can be amplified from nucleic acid samples using amplification techniques. For instance, polymerase chain reaction (PCR) technology can be used to amplify the sequences of the FIE genes directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. For a general overview of PCR see *PCR Protocols: A Guide to Methods and Applications.* (Innis, M, Gelfand, D., Sninsky, J. and White, T., eds.), *Academic Press,* San Diego (1990).

Appropriate primers and probes for identifying FIE sequences from plant tissues are generated from comparisons of the sequences provided here with other polycomb group genes. For instance, FIE1 can be compared to the other polycomb genes containing the SET domain, such as the Arabidopsis curly leaf gene (Goodrich et al. *Nature* 386:44–51 (1997)) or the Drosophila enhancer of zeste (E(z)) gene. FIE3 can be compared to genes containing WD40 repeats, such as the extra sex combs (esc) gene from Drosophila. Using these techniques, one of skill can identify conserved regions in the nucleic acids disclosed here to prepare the appropriate primer and probe sequences. Primers that specifically hybridize to conserved regions in FIE1 or FIE3 genes can be used to amplify sequences from widely divergent plant species.

Standard nucleic acid hybridization techniques using the conditions disclosed above can then be used to identify full length cDNA or genomic clones.

Control of FIE Activity or Gene Expression

Since FIE genes are involved in controlling seed, in particular endosperm, development, inhibition of endogenous Fie activity or gene expression is useful in a number of contexts. For instance, inhibition of expression is useful in the development of parthenocarpic fruit (i.e., fruit formed in the absence of fertilization).

In addition, inhibition of FIE activity can be used for production of fruit with small and/or degraded seed (referred to here as "seedless fruit") after fertilization. In many plants, particularly dicots, the endosperm is not persistent and eventually is degraded. Thus, in plants of the invention in which Fie activity is inhibited, embryo-less seed do not persist and seedless fruit are produced.

Alternatively, plants of the invention can be used to prevent pre-harvest sprouting in seeds, especially those derived from cereals. In these plants, the endosperm persists and is the major component of the mature seed. Premature growth of embryos in stored grain causes release of degradative enzymes which digest starch and other components of the endosperm. Plants of the present invention are useful in addressing this problem because the seeds lack an embryo and thus will not germinate.

In yet another use, nucleic acids of the invention can be used in the development of apomictic plant lines (i.e., plants in which asexual reproductive processes occur in the ovule, see, Koltunow, A. *Plant Cell* 5: 1425–1437 (1993) for a discussion of apomixis). Apomixis provides a novel means to select and fix complex heterozygous genotypes that cannot be easily maintained by traditional breeding. Thus, for instance, new hybrid lines with desired traits (e.g., hybrid vigor) can be obtained and readily maintained.

In still another use, nucleic acids of the invention can be used to control endosperm production in transgenic plants. In particular, inhibition of FIE activity can be used to produce larger seeds with increased endosperm. This trait is particularly useful in species in which the endosperm persists in the seed (e.g., monocots, particularly grains).

One of skill will recognize that a number of methods can be used to modulate FIE activity or gene expression. FIE activity can be modulated in the plant cell at the gene, transcriptional, posttranscriptional, translational, or posttranslational, levels. Techniques for modulating FIE activity at each of these levels are generally well known to one of skill and are discussed briefly below.

Methods for introducing genetic mutations into plant genes are well known. For instance, seeds or other plant material can be treated with a mutagenic chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as, for example, X-rays or gamma rays can be used.

Alternatively, homologous recombination can be used to induce targeted gene disruptions by specifically deleting or altering the FIE gene in vivo (see, generally, Grewal and Klar, *Genetics* 146: 1221–1238 (1997) and Xu et al., *Genes Dev.* 10: 2411–2422 (1996)). Homologous recombination has been demonstrated in plants (Puchta et al., *Experientia* 50: 277–284 (1994), Swoboda et al., *EMBO J.* 13: 484–489 (1994); Offringa et al., *Proc. Natl. Acad. Sci. USA* 90: 7346–7350 (1993); and Kempin et al. *Nature* 389:802–803 (1997)).

In applying homologous recombination technology to the genes of the invention, mutations in selected portions of an FIE gene sequences (including 5' upstream, 3' downstream, and intragenic regions) such as those disclosed here are made in vitro and then introduced into the desired plant using standard techniques. Since the efficiency of homologous recombination is known to be dependent on the vectors used, use of dicistronic gene targeting vectors as described by Mountford et al. *Proc. Natl. Acad. Sci. USA* 91: 4303–4307 (1994); and Vaulont et al. *Transgenic Res.* 4: 247–255 (1995) are conveniently used to increase the efficiency of selecting for altered FIE gene expression in transgenic plants. The mutated gene will interact with the target wild-type gene in such a way that homologous recombination and targeted replacement of the wild-type gene will occur in transgenic plant cells, resulting in suppression of FIE activity.

Alternatively, oligonucleotides composed of a contiguous stretch of RNA and DNA residues in a duplex conformation with double hairpin caps on the ends can be used. The RNA/DNA sequence is designed to align with the sequence of the target FIE gene and to contain the desired nucleotide change. Introduction of the chimeric oligonucleotide on an extrachromosomal T-DNA plasmid results in efficient and specific FIE gene conversion directed by chimeric molecules in a small number of transformed plant cells. This method is described in Cole-Strauss et al. *Science* 273:1386–1389 (1996) and Yoon et al. *Proc. Natl. Acad. Sci. USA* 93: 2071–2076 (1996).

Gene expression can be inactivated using recombinant DNA techniques by transforming plant cells with constructs comprising transposons or T-DNA sequences. FIE mutants prepared by these methods are identified according to standard techniques. For instance, mutants can be detected by PCR or by detecting the presence or absence of FIE mRNA, e.g., by Northern blots. Mutants can also be selected by assaying for development of endosperm in the absence of fertilization.

The isolated nucleic acid sequences prepared as described herein, can also be used in a number of techniques to control endogenous FIE gene expression at various levels. Subsequences from the sequences disclosed here can be used to control, transcription, RNA accumulation, translation, and the like.

A number of methods can be used to inhibit gene expression in plants. For instance, antisense technology can be conveniently used. To accomplish this, a nucleic acid segment from the desired gene is cloned and operably linked to a promoter such that the antisense strand of RNA will be transcribed. The construct is then transformed into plants and the antisense strand of RNA is produced. In plant cells, it has been suggested that antisense suppression can act at all levels of gene regulation including suppression of RNA, translation (see, Bourque *Plant Sci.* (*Limerick*) 105: 125–149 (1995); Pantopoulos In Progress in Nucleic Acid Research and Molecular Biology, Vol. 48. Cohn, W. E. and K. Moldave (Ed.). Academic Press, Inc.: San Diego, Calif., USA; London, England, UK. p. 181–238; Heiser et al. *Plant Sci.* (*Shannon*) 127: 61–69 (1997)) and by preventing the accumulation of mRNA which encodes the protein of interest, (see, Baulcombe *Plant Mol. Bio.* 32:79–88 (1996); Prins and Goldbach *Arch. Virol.* 141: 2259–2276 (1996); Metzlaff et al. *Cell* 88: 845–854 (1997), Sheehy et al., *Proc. Nat. Acad. Sci. USA,* 85:8805–8809 (1988), and Hiatt et al., U.S. Pat. No. 4,801,340).

The nucleic acid segment to be introduced generally will be substantially identical to at least a portion of the endogenous FIE gene or genes to be repressed. The sequence, however, need not be perfectly identical to inhibit expression. The vectors of the present invention can be designed such that the inhibitory effect applies to other genes within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of about 500 to about 1700 nucleotides is especially preferred.

A number of gene regions can be targeted to suppress FIE gene expression. The targets can include, for instance, the coding regions, introns, sequences from exon/intron junctions, 5' or 3' untranslated regions, and the like. In some embodiments, the constructs can be designed to eliminate the ability of regulatory proteins to bind to FIE gene sequences that are required for its cell- and/or tissue-specific expression. Such transcriptional regulatory sequences can be located either 5'-, 3'-, or within the coding region of the gene and can be either promote (positive regulatory element) or repress (negative regulatory element) gene transcription. These sequences can be identified using standard deletion analysis, well known to those of skill in the art. Once the sequences are identified, an antisense construct targeting these sequences is introduced into plants to control gene transcription in particular tissue, for instance, in developing ovules and/or seed.

Oligonucleotide-based triple-helix formation can be used to disrupt FIE gene expression. Triplex DNA can inhibit DNA transcription and replication, generate site-specific mutations, cleave DNA, and induce homologous recombination (see, e.g., Havre and Glazer *J. Virology* 67:7324–7331 (1993); Scanlon et al. *FASEB J.* 9:1288–1296 (1995); Giovannangeli et al. *Biochemistry* 35:10539–10548 (1996); Chan and Glazer *J. Mol. Medicine* (*Berlin*) 75: 267–282 (1997)). Triple helix DNAs can be used to target the same sequences identified for antisense regulation.

Catalytic RNA molecules or ribozymes can also be used to inhibit expression of FIE genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. Thus, ribozymes can be used to target the same sequences identified for antisense regulation.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Zhao and Pick *Nature* 365:448–451 (1993); Eastham and Ahlering *J. Urology* 156:1186–1188 (1996); Sokol and Murray *Transgenic Res.* 5:363–371 (1996); Sun et al. *Mol. Biotechnology* 7:241–251 (1997); and Haseloff et al. *Nature,* 334:585–591 (1988).

Another method of suppression is sense cosuppression. Introduction of nucleic acid configured in the sense orientation has been recently shown to be an effective means by which to block the transcription of target genes. For an example of the use of this method to modulate expression of endogenous genes (see, Assaad et al. *Plant Mol. Bio.* 22: 1067–1085 (1993); Flavell *Proc. Natl. Acad. Sci. USA* 91: 3490–3496 (1994); Stam et al. *Annals Bot.* 79: 3–12 (1997); Napoli et al., *The Plant Cell* 2:279–289 (1990); and U.S. Pat. Nos. 5,034,323, 5,231,020, and 5,283,184).

The suppressive effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For sense suppression, the introduced sequence, needing less than absolute identity, also need not be full length, relative to either the primary transcription product or fully processed mRNA. This may be preferred to avoid concurrent production of some plants which are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used. In addition, the same gene regions noted for antisense regulation can be targetted using cosuppression technologies.

Alternatively, FIE activity may be modulated by eliminating the proteins that are required for FIE cell-specific gene expression. Thus, expression of regulatory proteins and/or the sequences that control FIE gene expression can be modulated using the methods described here.

Another method is use of engineered tRNA suppression of FIE mRNA translation. This method involves the use of suppressor tRNAs to transactivate target genes containing premature stop codons (see, Betzner et al. *Plant J.*11:587–595 (1997); and Choisne et al. *Plant J.*11: 597–604 (1997). A plant line containing a constitutively expressed FIE gene that contains an amber stop codon is first created. Multiple lines of plants, each containing tRNA suppressor gene constructs under the direction of cell-type specific promoters are also generated. The tRNA gene construct is then crossed into the FIE line to activate FIE activity in a targeted manner. These tRNA suppressor lines could also be used to target the expression of any type of gene to the same cell or tissue types.

As noted above, FIE proteins as products of polycomb group genes are believed to form large complexes in vivo. Thus, production of dominant-negative forms of FIE polypeptides that are defective in their abilities to bind to other polycomb group proteins is a convenient means to inhibit endogenous FIE activity. This approach involves transformation of plants with constructs encoding mutant FIE polypeptides that form defective complexes with endogenous polycomb group proteins and thereby prevent the complex from forming properly. The mutant polypeptide may vary from the naturally occurring sequence at the primary structure level by amino acid substitutions, additions, deletions, and the like. These modifications can be used in a number of combinations to produce the final modified protein chain. Use of dominant negative mutants to inactivate target genes is described in Mizukami et al. *Plant Cell* 8:831–845 (1996).

Another strategy to affect the ability of an FIE protein to interact with itself or with other proteins involves the use of antibodies specific to FIE. In this method cell-specific expression of FIE-specific Abs is used inactivate functional domains through antibody:antigen recognition (see, Hupp et al. *Cell* 83:237–245 (1995)).

Use of Nucleic Acids of the Invention to Enhance FIE Gene Expression

Isolated sequences prepared as described herein can also be used to introduce expression of a particular FIE nucleic acid to enhance or increase endogenous gene expression. For instance, polycomb genes are known to control cell cycling. Enhanced expression can therefore be used to control plant morphology by controlling whether or not cell division takes place in desired tissues or cells. Enhanced expression can also be used, for instance, to increase vegetative growth by preventing the plant from setting seed. Where overexpression of a gene is desired, the desired gene from a different species may be used to decrease potential sense suppression effects.

One of skill will recognize that the polypeptides encoded by the genes of the invention, like other proteins, have different domains which perform different functions. Thus, the gene sequences need not be full length, so long as the desired functional domain of the protein is expressed.

Modified protein chains can also be readily designed utilizing various recombinant DNA techniques well known to those skilled in the art and described in detail, below. For example, the chains can vary from the naturally occurring sequence at the primary structure level by amino acid substitutions, additions, deletions, and the like. These modifications can be used in a number of combinations to produce the final modified protein chain.

Preparation of Recombinant Vectors

To use isolated sequences in the above techniques, recombinant DNA vectors suitable for transformation of plant cells are prepared. Techniques for transforming a wide variety of higher plant species are well known and described in the technical and scientific literature. See, for example, Weising et al. *Ann. Rev. Genet.* 22:421–477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region. the 1'- or 2'- promoter derived from T-DNA of *Agrobacterium tumafaciens,* and other transcription initiation regions from various plant genes known to those of skill. Such genes include for example, ACT11 from Arabidopsis (Huang et al. *Plant Mol. Biol.* 33:125–139 (1996)), Cat3 from Arabidopsis (GenBank No. U43147, Zhong et al., *Mol. Gen. Genet.* 251:196–203 (1996)), the gene encoding stearoyl-acyl carrier protein desaturase from *Brassica napus (Genbank No. X74782, Solocombe et al. Plant Physiol.* 104:1167–1176 (1994)), GPc1 from maize (GenBank No. X15596, Martinez et al. *J. Mol. Biol* 208:551–565 (1989)), and Gpc2 from maize (GenBank No. U45855, Manjunath et al., *Plant Mol. Biol.* 33:97–112 (1997)).

Alternatively, the plant promoter may direct expression of the FIE nucleic acid in a specific tissue or may be otherwise under more precise environmental or developmental control. Examples of environmental conditions that may effect transcription by inducible promoters include anaerobic conditions, elevated temperature, or the presence of light. Such promoters are referred to here as "inducible" or "tissue-specific" promoters. One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

Examples of promoters under developmental control include promoters that initiate transcription only (or primarily only) in certain tissues, such as fruit, seeds, or flowers. Promoters that direct expression of nucleic acids in ovules, flowers or seeds are particularly useful in the present invention. As used herein a seed-specific promoter is one which directs expression in seed tissues, such promoters may be, for example, ovule-specific (which includes promoters which direct expression in maternal tissues or the female gametophyte, such as egg cells or the central cell), embryo-specific, endosperm-specific, integument-specific, seed coat-specific, or some combination thereof. Examples include a promoter from the ovule-specific BEL1 gene described in Reiser et al. *Cell* 83:735–742 (1995) (GenBank No. U39944). Other suitable seed specific promoters are derived from the following genes: MAC1 from maize (Sheridan et al. *Genetics* 142:1009–1020 (1996), Cat3 from maize (GenBank No. L05934, Abler et al. *Plant Mol. Biol.* 22:10131–1038 (1993), the gene encoding oleosin 18kD from maize (GenBank No. J05212, Lee et al. *Plant Mol. Biol.* 26:1981–1987 (1994)), vivparous-1 from Arabidopsis (Genbank No. U93215), the gene encoding oleosin from Arabidopsis (Genbank No. Z17657), Atmyc1 from Arabidopsis (Urao et al. *Plant Mol. Biol.* 32:571–576 (1996), the 2s seed storage protein gene family from Arabidopsis (Conceicao et al. *Plant* 5:493–505 (1994)) the gene encoding oleosin 20kD from *Brassica napus* (GenBank No. M63985), napA from *Brassica napus* (GenBank No. J02798, Josefsson et al. JBL 26:12196–1301 (1987), the napin gene family from *Brassica napus* (Sjodahl et al. *Planta* 197:264–271 (1995), the gene encoding the 2S storage protein from *Brassica napus* (Dasgupta et al. *Gene* 133:301–302 (1993)), the genes encoding oleosin A (Genbank No. U09118) and oleosin B (Genbank No. U09119) from soybean and the gene encoding low molecular weight sulphur rich protein from soybean (Choi et al. *Mol Gen, Genet.* 246:266–268 (1995)).

In addition, the promoter sequences from the FIE genes disclosed here can be used to drive expression of the FIE polynucleotides of the invention or heterologous sequences. The sequences of the promoters are identified below.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulfuron or Basta.

Production of Transgenic Plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment.

Microinjection techniques are known in the art and well described in the scientific and patent literature. The introduction of DNA constructs using polyethylene glycol precipitation is described in Paszkowski et al. *Embo J.* 3:2717–2722 (1984). Electroporation techniques are described in Fromm et al. *Proc. Natl. Acad. Sci. USA* 82:5824 (1985). Ballistic transformation techniques are described in Klein et al. *Nature* 327:70–73 (1987).

Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, for example Horsch et al. *Science* 233:496–498 (1984), and Fraley et al. *Proc. Natl. Acad. Sci. USA* 80:4803 (1983).

Transformed plant cells which are derived by any of the above transformation techniques can be cultured to regenerate a whole plant which possesses the transformed genotype and thus the desired phenotype such as increased seed mass. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., *Protoplasts Isolation and Culture, Handbook of Plant Cell Culture*, pp. 124–176, MacMillilan Publishing Company, New York, 1983; and Binding, *Regeneration of Plants, Plant Protoplasts*, pp. 21–73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467–486 (1987).

The nucleic acids of the invention can be used to confer desired traits on essentially any plant. Thus, the invention has use over a broad range of plants, including species from the genera Anacardium, Arachis, Asparagus, Atropa, Avena, Brassica, Citrus. Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannesetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna, and Zea.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Seed obtained from plants of the present invention can be analyzed according to well known procedures to identify plants with the desired trait. If antisense or other techniques are used to control Fie gene expression, Northern blot analysis can be used to screen for desired plants. In addition, the presence of fertilization independent reproductive development can be detected. Plants can be screened, for instance, for the ability to form embryo-less seed, form seed that abort after fertilization, or set fruit in the absence of fertilization. These procedures will depend, part on the particular plant species being used, but will be carried out according to methods well known to those of skill.

The following Examples are offered by way of illustration, not limitation.

EXAMPLE 1

The following example describes methods used to identify the fie mutants. The methods described here are generally as described in Ohad et al., *Proc. Natl. Acad. Sci. USA* 93:5319–5324 (1996).

Materials and Methods

Growth and Phenotype of Plants

Plants were grown under low humidity conditions (less than 50%) in glass houses under 16 hr light/8 hr dark photoperiods generated by supplemental lighting. Plants were grown at high humidity (greater than 80%) in a lighted incubator (Percival, Boone, Iowa).

To test for fertilization-independent development, flower buds from plants that had not yet begun to shed pollen (stage 12; (Smyth, D. R., et al., *Plant Cell* 2: 755–761 (1990))) were opened, immature anthers were removed, and the flower bud was covered with a plastic bag. Seven days later, the silique was measured, dissected, and the number of seed-like structures and degenerating ovules were counted. To determine the frequency of seed abortion following fertilization, siliques were harvested 10 days after self-pollination, dissected, and wild-type and aborted seeds were counted.

Genetic Mapping

Heterozygous FIE/fie (Landsberg erecta ecotype) plants were crossed as males with female plants (Columbia ecotype). Because the mutant fie allele is only transmitted through the male gametophyte, FIE/fie progeny were crossed as males a second time to female gl1/gl1 (Columbia ecotype) plants. Approximately fifty-five progeny were scored for the segregation of the wild-type FIE and mutant fie alleles and for alleles of molecular markers as described previously (Bell, C., et al., *Genomics* 19: 137–144 (1994)). This analysis indicated that fie3 is located at approximately position 30 on chromosome three, fie2 is located at approximately position 65 on chromosome two, and fie1 is located at approximately position 2 on chromosome one. Genetic recombination frequencies and map distances were calculated according to Koornneef and Stam (Koornneef, M., et al., *Methods in Arabidopsis Research*, pp. 83–99 (1992)) and Kosambi (Kosambi, *Ann. Eugen.*, 12: 172–175 (1944)).

Light Microscopy

Nomarski photographs of whole-mount embryos and endosperm were obtained by fixing longitudinally slit siliques in an ethanol:acetic acid (9:1) solution overnight, followed by two washes in 90% and 70% ethanol, respectively. Siliques were cleared with a chloral hydrate:glycerol:water solution (8:1:2, w:v:v) (Berleth, T., et al., *Devel* 118: 575–587 (1993)). Whole mount preparations were fixed and stained with hematoxylin (Beeckman, T., et al., *Plant Mol Biol Rep* 12: 37–42 (1994)). Embryo and endosperm were photographed with a Zeiss Axioskop microscope (Carl Zeiss, Inc., Oberkochen, Germany) using Nomarski optics that permits visualization of optical sections within the seed.

GUS Histochemical Assays

GUS activity was detected histochemically as described previously by (Beeckman, T., et al., *Plant Mol Biol Rep* 12: 37–42 (1994)).

Image Processing

Photographs were scanned using a Microtek scanner. Pictures were processed for publication using Adobe Photoshop 3.0 and printed on a Tektronix Phaser 400 color printer.

Results

Isolation of Mutant Lines

To begin to understand mechanisms that initiate reproductive development, we generated mutant Arabidopsis plants that undergo several reproductive processes in the absence of fertilization. Arabidopsis plants homozygous for the conditional male sterile pop1 mutation (Preuss, D., et al., *Genes and Devel* 7: 974–985 (1993)) were used as the parental strain (Landsberg erecta ecotype). Fertility in pop1 plants is sensitive to humidity because pop1 pollen do not hydrate properly due to a defect in wax biosynthesis. When grown at permissive condition, high relative humidity (>80%), popI plants were male fertile and produced long siliques with many viable seeds. By contrast, when grown at non-permissive condition, low relative humidity (<50%), pop1 plants were male sterile and produced short siliques with no seeds. Thus, silique elongation is a marker for reproductive events. To isolate mutations, homozygous pop1 seeds were mutagenized with ethylmethansulfonate (EMS) and approximately 50,000 M1 plants were screened for silique elongation at non-permissive conditions. Rare M1 plants were identified that displayed heterozygous sectors with elongated siliques. These plants were transferred to permissive conditions to insure the production of viable M2 seed. Plants from M2 and M3 families grown at non-permissive conditions were rechecked for non-sectored silique elongation. To eliminate any effects of the pop1 mutation, or other EMS-induced lesions on the mutant phenotype, mutant plants were backrossed twice, as males, to wild-type plants. After removing the pop1 mutation, fertilization-independent phenotypes were confirmed after manual removal of anthers from immature flowers before pollen was shed. A total of twelve lines were identified that displayed elongated siliques in the absence of fertilization.

Fertilization-Independent Endosperm, Seed Coat and Silique Development

In a representative line chosen for further study, heterozygous plants produced by back crosses to wild-type plants generated elongated siliques after anther removal with numerous seed-like, structures. These results indicated that heterozygous mutant plants were capable of silique, elongation and seed-like structure development in the absence of fertilization. We compared the development of the mutant seed-like structures to that of wild-type seeds. After fertilization, the endosperm nucleus replicated and daughter nuclei migrated into the expanding central cell. Ultimately, a syncytium of endosperm nuclei was produced. Nuclear divisions of the endosperm preceded the zygotic divisions that formed the globular stage embryo. Embryo, endosperm or seed coat development did not occur in wild-type plants in the absence of fertilization. Development of the ovule and female gametophyte in heterozygous mutant plants was normal. Just prior to flower opening, female gametophytes in these plants contained a single, prominent central cell nucleus. Subsequently, in the absence of fertilization, central cells with two large nuclei were detected. Further divisions resulted in the production of additional nuclei that migrated into the expanded central cell. Later in development, a nuclear syncytium was formed with abundant endosperm nuclei. These results indicated that the central cell in mutant female gametophytes initiated endosperm development in the absence of fertilization. We have named this mutation fie for fertilization-independent endosperm. By contrast, replication of other nuclei in fie female gametophytes (egg, synergid, or antipodal) was not detected. Thus, the fie mutation specifically affects replication of the central cell nucleus.

We analyzed the frequency of multinucleate central cell formation in fie female gametophytes by comparing the percentage of multinucleate central cells at three, five, and six days after emasculation of heterozygous FIE/fie and control wild-type flowers. At each time point, only 3% to 5% of wild-type central cells had more than one nucleus. Because none had more than two nuclei, most likely, these represented central cells with haploid nuclei that had not fused during female gametophyte development. By contrast, the percentage of central cells in female gametophytes from FIE/fie siliques with two or more nuclei increased from 21% to 47% over the same time period. These results indicated that the fie mutation caused a significant increase in formation of multinucleate central cells in the absence of fertilization. The fact that close to 50% of the female gametophytes in heterozygous plants had multinucleate central cells suggested that fie is a gametophytic mutation because a 1:1 segregation of wild-type and mutant fie alleles occurs during meiosis.

We compared the fertilization-independent development of the maternal seed coat in FIE/fie seed-like structures to that of fertilized wild-type seeds. The seed coat in wild-type Arabidopsis is generated by the integuments of the ovule and surrounds the developing embryo and endosperm. Similarly, FIE/fie ovule integuments formed a seed coat that surrounded the developing mutant endosperm. These results indicated that the fie mutation activated both endosperm development and maternal sporophytic seed coat and silique differentiation that support reproduction. No other effects on sporophytic growth and development were detected in FIE/fie plants.

The fie3 Mutant Allele is not Transmitted by the Female Gametophyte to the Next Generation To understand the mode of inheritance of the fie mutation, we analyzed the progeny of reciprocal crosses. FIE3/fie3 females, crossed to wild-type males, produced siliques with approximately equal numbers of viable seeds with normal green embryos and nonviable white seeds with embryos aborted at the heart stage (344:375, 1:1, c2=1.3, P>0.2). Viable seeds from this cross were germinated and all 120 F1 progeny generated were wild-type. That is, none of the F1 progeny had significant levels of F2 aborted seeds in their siliques after self-pollination. Nor did the F1 progeny demonstrate fertilization-independent development. This indicated that presence of the fie mutant allele in the female gametophyte, even when the male provided a wild-type allele, resulted in embryo abortion Thus, the fie mutation is not transmitted by the female gametophyte to the next generation. To study transmission of fie through the male gametophyte, we pollinated female wild-type plants with pollen from male FIE3/fie3 plants. Siliques from these crosses contained no aborted F1 seed. F1 plants were examined and a 1:1 segregation of wild-type and FIE3/fie3 genotype was observed (62:58, c2=0.13, P>0.5). This indicated that wild-type and mutant fie3 alleles were transmitted by the male gametophyte with equal efficiency. That is, fie does not affect male gametophyte, or pollen grain, function. Results from reciprocal crosses were verified by analyzing the progeny from self-pollinated FIE3/fie3 plants. Self-pollinated siliques displayed 1:1 segregation of normal and aborted seeds (282:286, c2=0.03, P>0.8). Viable seed from self-pollinated siliques were germinated and a 1:1 (71:64, c2=0.36, P>0.5) segregation of wild-type and FIE3/fie3 progeny was observed. These results confirmed that inheritance of a fie mutant allele by the female gametophyte resulted in embryo abortion, and that inheritance of a fie mutant allele by the male gametophyte did not affect pollen function. Thus, the wild-type FIE3 allele probably carries out a function unique to the female gametophyte and does not appear to be needed for male fertility.

In contrast, fie1 and fie2 mutant alleles were transmitted at low frequencies (about 1% of normal) through the female gametophyte. In this way, fie1 homozygous mutants and fie2 homozygous mutants were obtained that appeared to display normal vegetative growth and development.

Discussion

In wild-type plants, fertilization initiates embryogenesis and endosperm formation, and activates maternal seed coat and silique development. The results presented here indicate that specific aspects of plant reproductive development can occur in FIE/fie plants in the absence of fertilization. These include silique elongation, seed coat formation, and endosperm development. Morphological analysis shows that early aspects of fertilization-independent fie endosperm development closely resemble fertilized wild-type endosperm development. First, the fie central cell nucleus is stimulated to undergo replication. Second, nuclei that are produced migrate from the micropylar end of the central cell and take up new positions in the central cell. Third, the developing fie central cell expands to form an endosperm cavity. Thus, the requirement for fertilization to initiate these early events in endosperm formation has been eliminated by the fie mutation. This suggests that FIE plays a role in a signal transduction pathway that links fertilization with the onset of central cell nuclear replication and early endosperm development.

Mechanisms for Regulation of Endosperm Development by FIE

One can envision two possible mechanisms for how FIE regulates replication of the central cell nucleus in response to fertilization. The protein encoded by the FIE gene may be involved in a positive regulatory interaction. In this model, FIE is required for the central cell to initiate endosperm development. Normally, fertilization is needed for the presence of active FIE protein. The fie mutation results in the presence of active protein in the absence of fertilization. Alternatively, FIE may by involved in a negative regulatory interaction. In this model, the function of FIE protein is to prevent the central cell from initiating endosperm development, and fertilization results in the inactivation of FIE protein. The fie mutation results in the production of inactive protein, so that fertilization is no longer required to initiate endosperm development. However, complementation experiments using transgenic plants indicate that FIE1 and FIE3 alleles are dominant over their respective mutant alleles. This indicates that the wild-type allele is involved in a negative regulatory interaction. Recently, it has been shown that cyclin-dependent kinase complexes, related to those that function in mammals, control the induction of DNA synthesis and mitosis in maize endosperm (Grafi, G.et al., *Science* 269:1262–1264 (1995)). Because fie stimulates replication of the central cell, fie may, either directly or indirectly, impinge upon cell cycle control of the central cell nucleus, allowing replication to take place in the absence of fertilization.

Communication between the fie Female Gametophyte and the Sporophytic Ovule and Carpels The analysis of FIE/fie mutant plants has provided clues about interactions between endosperm and maternal sporophytic tissues. FIE/fie ovule integuments surrounding a mutant fie female gametophyte initiate seed coat development, whereas FIE/fie integuments in contact with a quiescent wild-type female gametophyte do not develop. This suggests that the FIE/fie ovule integuments initiate seed coat differentiation in response to a signal produced by the fie female gametophyte. We propose that the source of the signal is the mutant fie central cell that has initiated endosperm development, although we cannot rule out the participation of other cells in the fie female gametophyte. In wild-type plants, most likely, fertilization of the central cell produces an endosperm that activates seed coat development. This is consistent with experiments showing that the maize endosperm interacts with nearby maternal cells (Miller, M. E., et al., *Plant Cell* 4: 297–305 (1992)). FIE/fie plants also display fertilization-independent elongation of the ovary to form the silique. We propose that a signal is produced by the developing seed-like structures to initiate silique elongation. This is in agreement with experiments suggesting that seeds are the source of hormones, auxins and gibberellins, that activate fruit development (Lee, T. D. *Plant Reproductive Ecology,* pp. 179–202 (1988)). Taken together, these results suggest that the fertilized female gametophyte activates maternal developmental programs.

Relationship between Fie and Apomixis

Certain plant species display aspects of fertilization-independent reproductive development, including apomictic generation of embryo and endosperm, and development of the maternal seed coat and fruit (reviewed in (Koltunow, a. *Plant Cell* 5: 1425–1437 (1993)). The fie mutation reveals that Arabidopsis, a sexually reproducing plant, has the genetic potential for aspects of fertilization-independent reproductive development. It is not known whether the mechanism of fertilization-independent endosperm development conferred by the fie mutation is the same as autonomous endosperm formation observed in certain apomictic plant species. However, the fact that the fie phenotype is caused by a single genetic locus substantiates the view that the number of genetic differences between sexually and asexually reproducing plants is small (Koltunow, a. M., et al., *Plant Physiol* 108:1345–1352 (1995)).

EXAMPLE 2

This example describes cloning of two Fie genes, Fie1 and Fie3

Figure 3:
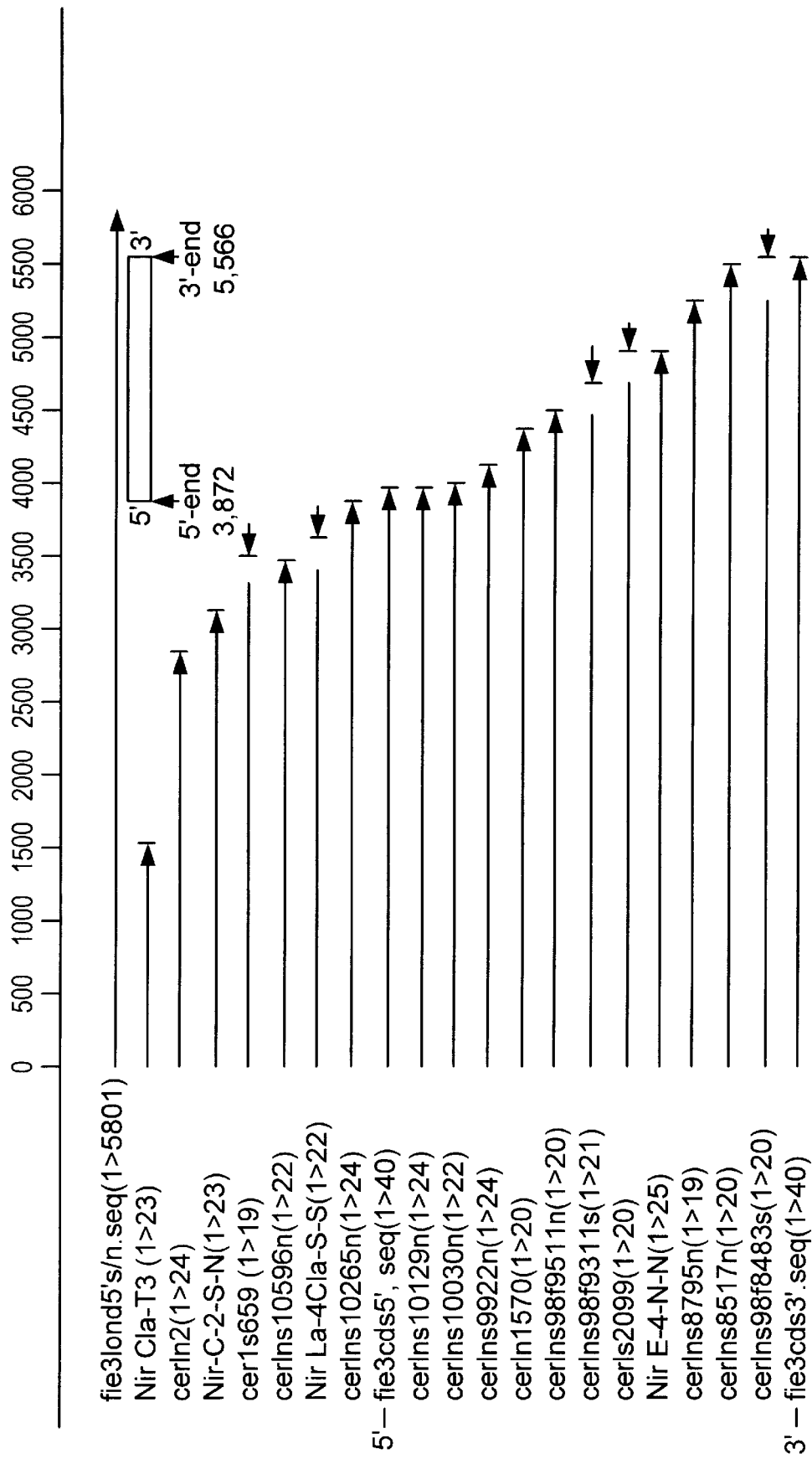
FIG. 3 shows the position of primers used to PCR amplify sequences from the FIE3 gene region.

Cloning the FIE3 Gene a. Mapping the position of the fie3 gene genetically. The fie3 mutation was initially mapped to position 30 on chromosome 3, between AXR2 (auxin resistant dwarf) and EMB29 (embryo lethal). Next, two sets of F2 plants with recombination breakpoints in the fie3 gene region were obtained. One set was between emb29 and fie3 and the other set was between axr2 and fie3. As shown in FIG. 1A, these recombinants were used to map the fie3 gene relative to molecular markers (NDR, CH18, CH18S, BO20, AG20, KN1 and E13F12) that were obtained from overlapping YAC (yUP13F12), BAC (T1B4 and T4N1) and cosmid clones (FIG. 1A). YAC and BAC clones were obtained from the Arabidopsis Stock Center (Ohio State University, USA). Cosmid subclones were generated in my laboratory. As shown in FIGS. 1A and 1B, this genetic analysis indicates that the fie3 gene resides within the 25 Kb region between the BO20 and AG20 markers.

b. Mapping the position of the fie3 gene by complementation experiments. To more precisely localize the fie3 gene, we analyzed a series of overlapping cosmid clones (BO20, GM15, AG20 and EI12) that span the fie3 gene region. Each cosmid clone was tested for its ability to complement the fie3 mutation in transgenic plants. Only cosmid GM15 complemented the fie3 mutation (FIG. 1A). These results indicate that an essential portion of the fie3 gene is in the 10 Kb region that is unique to cosmid GM15. As shown in FIG. 1B, we have cloned DNA that spans this essential portion of the fie3 gene and have determined its DNA sequence. As shown in FIG. 2, analysis of the sequence using the GENSCANW program revealed a gene with an open reading frame. The predicted cDNA sequence and predicted amino acid sequence are shown in SEQ ID NO:3 and SEQ ID NO:4, respectively. Comparing the predicted amino acid sequence to those in public data bases revealed significant homology to the WD40 family of Polycomb Group genes, and in particular, the "extra sex combs" gene in Drosophila. FIG. 3 shows the position of primers used to PCR amplify this region. SEQ ID NO:5 provides the genomic DNA sequence of the WD40/Polycomb gene, plus approximately 3.8 Kb of 5'-flanking sequences and 0.3 Kb of 3'-flanking sequences, plus the sequence of primers (SEQ ID NOS:305–324) used to PCR amplify this region. The transcription start site in SEQ ID NO:5 is at position 3,872. Thus, the promoter sequence for FIE3 is located between position 1 and 3,872. The 5'-flanking and 3'-flanking regions contain regulatory DNA sequences that control the expression of this gene.

Figure 4:
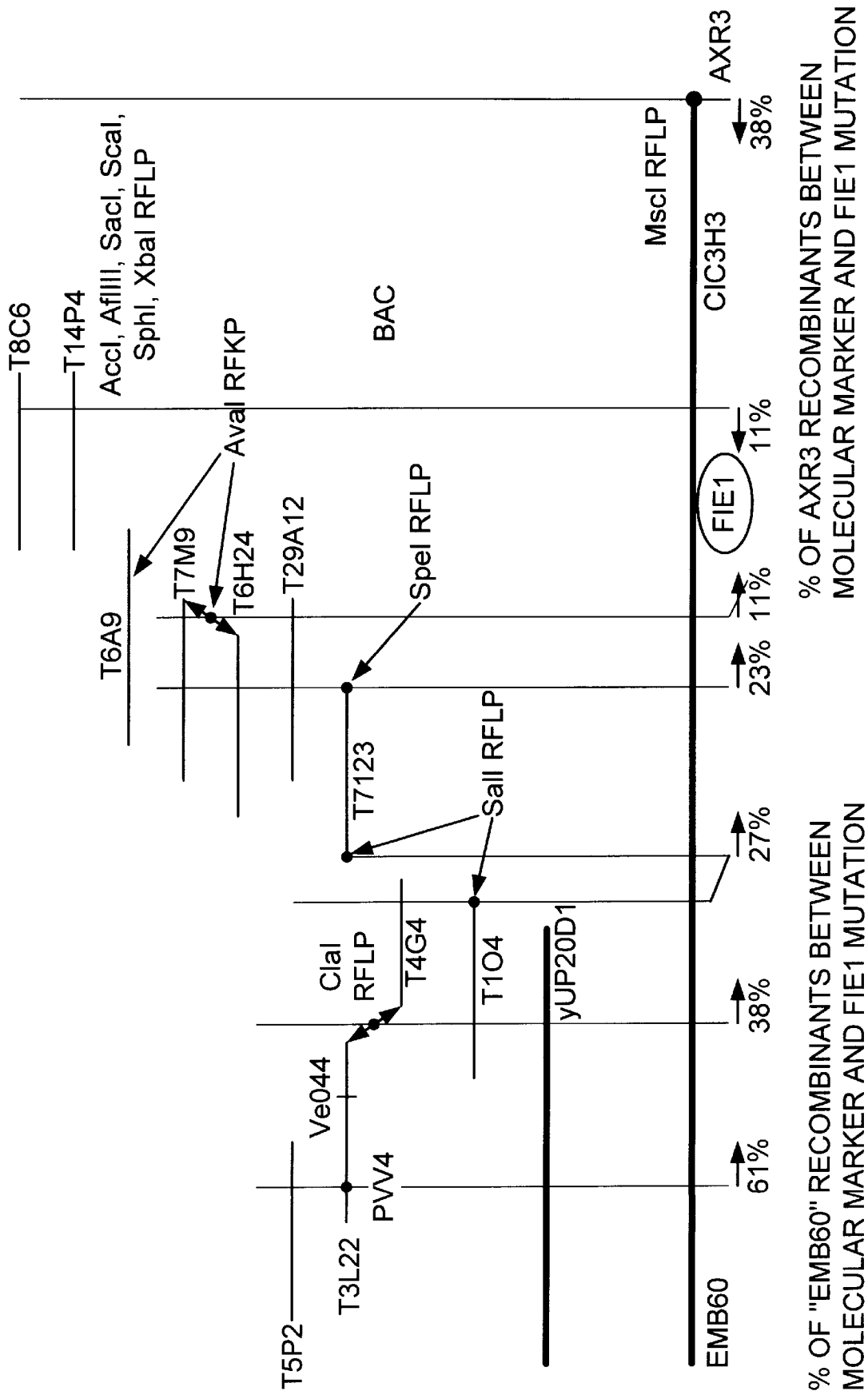
FIG. 4 shows the genetic map used to clone the FIE1 gene.
Figure 5:
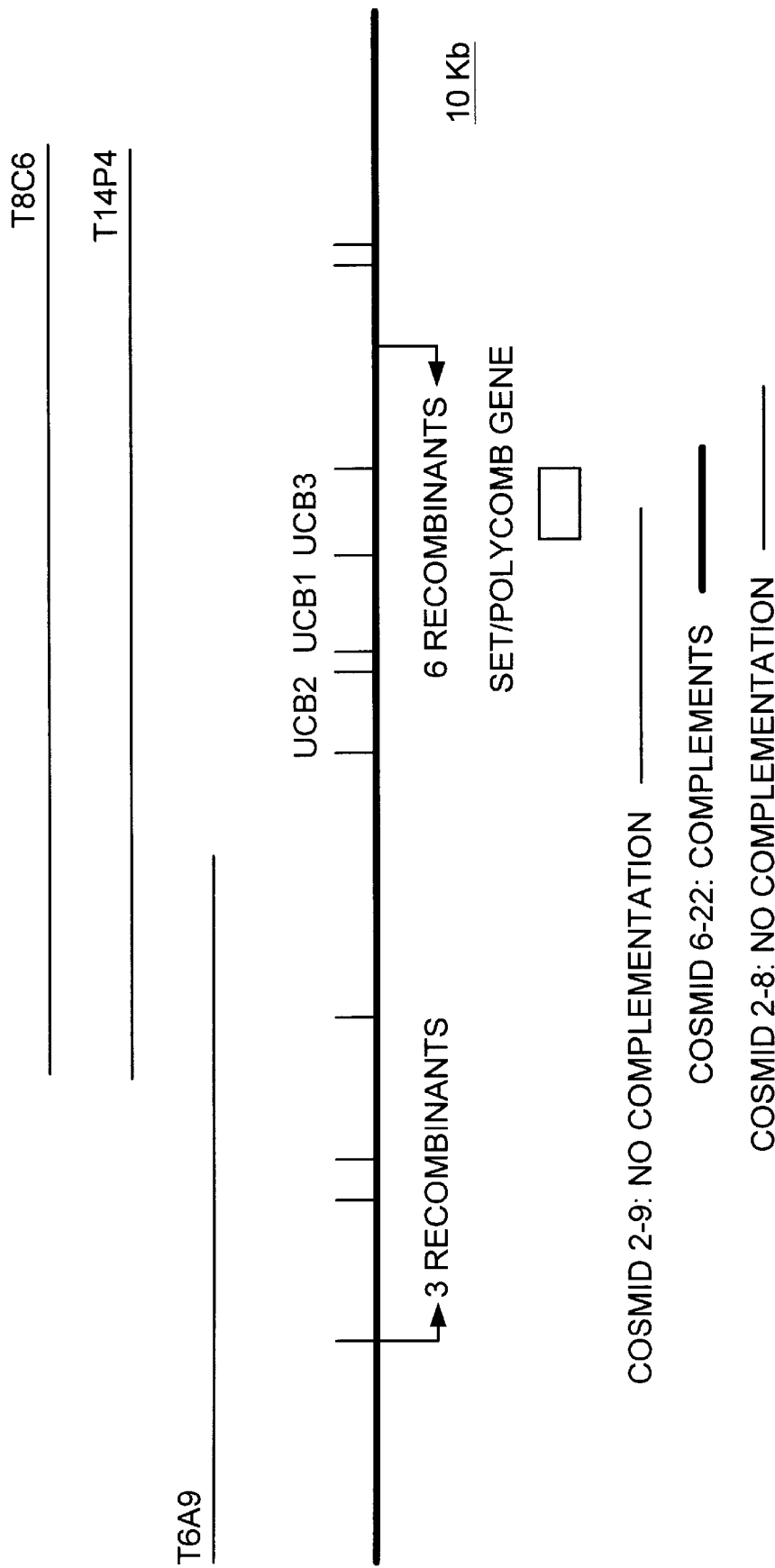
FIG. 5 shows the results of complementation tests establishing that a single gene (FIE1) was present on the complementing cosmid (6–22) that was not fully encoded on either of the non-complementing cosmids (2–9 and 2–8).

Cloning the FIE1 Gene a. Mapping the position of the FIE1 gene genetically. The fie1 mutation was initially mapped to position 3 on chromosome 1, between AXR3 (auxin resistant dwarf) and EMB60 (embryo lethal). Next, two sets of F2 plants with recombination breakpoints in the FIE1 gene region were obtained. One set was between emb60 and fie3 and the other set was between axr3 and fie3. These recombinants were used to map the fie3 gene relative to molecular markers (FIG. 4) that were obtained from an overlapping series of YAC and BAC clones from the Arabidopsis Stock Center (Ohio State University, USA).

b. Mapping the position of the FIE1 gene by complementation experiments. To more precisely localize the FIE1 gene, a series of overlapping cosmid clones (2–9, 6–22, 2–8) that span the FIE1 gene region were analyzed (FIG. 4). Each cosmid clone was tested for its ability to complement the fie1 mutation in transgenic plants. Only cosmid 6–22 complemented the fie1 mutation. The cosmids were analyzed for genes with open reading frames. FIG. 5 shows that a single gene was present on the complementing cosmid (6–22) that was not fully encoded on either of the non-complementing cosmids (2–9 and 2–8). By RTPCR and 5'-race, the cDNA sequence of this gene and predicted amino acid of its protein were obtained (SEQ ID NO:1 and SEQ ID NO:2, respectively). Comparison of the predicted amino acid sequence to those in public data bases revealed significant homology to the SET family of Polycomb Group Genes (e.g., Enhancer of Zeste in Drosophila and Curly Leaf in Arabiopsis). We compared the wild-type and fie1 mutant sequence in 6–22. The only difference is a single base pair change that creates a premature translation stop codon in the 5'-end of the set/polycomb group gene. The base pair change is at position 823 (C-→T) on the cDNA sequence shown in SEQ ID NO:1.

SEQ ID NO:6 shows the genomic sequence of the FIE1 SET/polycomb gene, plus approximately 2 Kb of 5'-flanking sequences and approximately 0.7 Kb of 3'-flanking sequences. The translation start site is located at position 2036 of SEQ ID NO:6. Thus, the promoter sequence is located between position 1 and position 2036. Peptides encoded by reading frame 1=SEQ ID NOS:7–111; reading frame 2=SEQ ID NOS:112–200; reading frame 3=SEQ ID NOS:201–304.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. An isolated double stranded nucleic acid molecule comprising a polynucleotide that:
   a. specifically hybridizes to SEQ ID NO:3 in a buffer of 40% formamide, 1M NaCl, 1% SDS at 37° C., followed by one wash for 20 minutes in 0.2×SSC at a temperature of about 50° C.; and
   b. enhances endosperm development in the absence of fertilization when the polynucleotide is operably linked to a plant promoter to inhibit gene expression and introduced into a plant.

2. The isolated double stranded nucleic acid molecule of claim 1, wherein the polynucleotide is at least 100 nucleotides in length.

3. The isolated double stranded nucleic acid molecule of claim 1, wherein the polynucleotide comprises SEQ ID NO:3.

4. The isolated double stranded nucleic acid molecule of claim 1, wherein the polynucleotide encodes a FIE polypeptide.

5. The isolated double stranded nucleic acid molecule of claim 4, wherein the FIE polypeptide comprises SEQ ID NO:4.

6. The isolated double stranded nucleic acid molecule of claim 1, wherein the polynucleotide is operably linked to a plant promoter.

7. The isolated double stranded nucleic acid molecule of claim 6, wherein the plant promoter is tissue-specific.

8. The isolated double stranded nucleic acid molecule of claim 7, wherein the plant promoter is ovule- or embryo-specific.

9. The isolated double stranded nucleic acid molecule of claim 6, wherein the plant promoter is from a FIE3 gene.

10. The isolated double stranded nucleic acid molecule of claim 6, wherein the polynucleotide is operably linked to the plant promoter in an antisense orientation.

11. The isolated double stranded nucleic acid molecule of claim 6, wherein the polynucleotide is operably linked to the plant promoter in a sense orientation.

12. A transgenic plant comprising an expression cassette comprising a plant promoter operably linked to the polynucleotide of claim 1.

13. The transgenic plant of claim 12, wherein the polynucleotide is at least 100 nucleotides in length.

14. The transgenic plant of claim 12, wherein the polynucleotide comprises SEQ ID NO:3.

15. The transgenic plant of claim 12, wherein the polynucleotide encodes a FIE polypeptide.

16. The transgenic plant of claim 15, wherein the FIE polypeptide comprises SEQ ID NO:4.

17. The transgenic plant of claim 12, wherein the polynucleotide is operably linked to a plant promoter.

18. The transgenic plant of claim 17, wherein the plant promoter is tissue-specific.

19. The transgenic plant of claim 17, wherein the plant promoter is ovule- or embryo-specific.

20. The transgenic plant of claim 17, wherein the plant promoter is from a FIE3 gene.

21. The transgenic plant of claim 17, wherein the polynucleotide is operably linked to the plant promoter in an antisense orientation.

22. The transgenic plant of claim 17, wherein the polynucleotide is operably linked to the plant promoter in a sense orientation.

* * * * *